(12) United States Patent
Tran et al.

(10) Patent No.: US 10,046,229 B2
(45) Date of Patent: *Aug. 14, 2018

(54) SMART DEVICE

(71) Applicant: Bao Tran, Saratoga, CA (US)

(72) Inventors: Bao Tran, Saratoga, CA (US); Ha Tran, Saratoga, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/626,099

(22) Filed: Jun. 17, 2017

(65) Prior Publication Data

US 2017/0312614 A1    Nov. 2, 2017

Related U.S. Application Data

(63) Continuation-in-part of application No. 15/407,248, filed on Jan. 16, 2017, now Pat. No. 9,717,949, which
(Continued)

(51) Int. Cl.
*B60Q 1/00* (2006.01)
*A63B 71/14* (2006.01)
(Continued)

(52) U.S. Cl.
CPC .......... *A63B 71/145* (2013.01); *A42B 3/0433* (2013.01); *A61B 5/11* (2013.01); *A61B 5/6804* (2013.01); *A63B 43/004* (2013.01); *A63B 60/46* (2015.10); *A63B 69/36* (2013.01); *A63B 69/38* (2013.01); *A63B 71/06* (2013.01); *B33Y 10/00* (2014.12); *G01L 5/0052* (2013.01); *G06F 1/163* (2013.01); *G06F 3/00* (2013.01); *G06F 3/017* (2013.01); *G06K 9/00342* (2013.01); *G09B 19/0038* (2013.01); *G16H 50/20* (2018.01); *H04N 5/2257* (2013.01);

*H04W 84/18* (2013.01); *A63B 21/072* (2013.01); *A63B 21/0724* (2013.01); *A63B 21/0726* (2013.01); *A63B 69/0002* (2013.01); *A63B 69/0026* (2013.01); *A63B 69/0028* (2013.01); *A63B 69/0048* (2013.01); *A63B 69/0071* (2013.01); *A63B 69/02* (2013.01); *A63B 69/06* (2013.01); *A63B 69/16* (2013.01); *A63B 69/3632* (2013.01); *A63B 71/085* (2013.01); *A63B 71/10* (2013.01); *A63B 71/1216* (2013.01); *A63B 71/1291* (2013.01); *A63B 71/141* (2013.01); *A63B 2071/125* (2013.01); *A63B 2071/1233* (2013.01); *A63B 2071/1283* (2013.01); *A63B 2207/02* (2013.01); *A63B 2220/12* (2013.01); *A63B 2220/13* (2013.01); *A63B 2220/16* (2013.01); *A63B 2220/20* (2013.01); *A63B 2220/24* (2013.01); *A63B 2220/30* (2013.01); *A63B 2220/40* (2013.01); *A63B 2220/51* (2013.01); *A63B 2220/53* (2013.01); *A63B 2220/56* (2013.01); *A63B 2220/72* (2013.01);
(Continued)

(58) Field of Classification Search
USPC ...................................................... 463/16–42
See application file for complete search history.

(56) References Cited

U.S. PATENT DOCUMENTS 6,155,490 A    12/2000  Ackley
6,452,088 B1   9/2002   Schmidt
(Continued)

*Primary Examiner* — Masud Ahmed
(74) *Attorney, Agent, or Firm* — Tran & Associates

(57) ABSTRACT

An Internet of Thing (IoT) device includes a body with a processor, a camera and a wireless transceiver coupled to the processor.

20 Claims, 14 Drawing Sheets

Related U.S. Application Data is a continuation of application No. 15/144,773, filed on May 2, 2016, now Pat. No. 9,610,476.

(51) Int. Cl.

| | | |
|---|---|---|
| *G06F 1/16* | (2006.01) | |
| *G01L 5/00* | (2006.01) | |
| *H04W 84/18* | (2009.01) | |
| *A63B 69/36* | (2006.01) | |
| *A61B 5/11* | (2006.01) | |
| *A61B 5/00* | (2006.01) | |
| *G06F 3/00* | (2006.01) | |
| *G06K 9/00* | (2006.01) | |
| *G09B 19/00* | (2006.01) | |
| *B33Y 10/00* | (2015.01) | |
| *A42B 3/04* | (2006.01) | |
| *A63B 69/38* | (2006.01) | |
| *A63B 71/06* | (2006.01) | |
| *A63B 43/00* | (2006.01) | |
| *G06F 3/01* | (2006.01) | |
| *H04N 5/225* | (2006.01) | |
| *A63B 60/46* | (2015.01) | |
| *G16H 50/20* | (2018.01) | |
| *A63B 71/12* | (2006.01) | |
| *A63B 69/00* | (2006.01) | |
| *A63B 69/02* | (2006.01) | |
| *A63B 69/06* | (2006.01) | |
| *A63B 69/16* | (2006.01) | |
| *A63B 71/08* | (2006.01) | |
| *A63B 71/10* | (2006.01) | |
| *A63B 21/072* | (2006.01) | |
| *H04B 1/04* | (2006.01) | |
| *H04N 7/18* | (2006.01) | |
| *H04W 88/02* | (2009.01) | |
| *H04L 29/08* | (2006.01) | |

(52) U.S. Cl.
CPC ....... *A63B 2220/74* (2013.01); *A63B 2220/75* (2013.01); *A63B 2220/76* (2013.01); *A63B 2220/803* (2013.01); *A63B 2220/806* (2013.01); *A63B 2220/807* (2013.01); *A63B 2220/833* (2013.01); *A63B 2220/836* (2013.01); *A63B 2225/30* (2013.01); *A63B 2225/50* (2013.01); *A63B 2225/54* (2013.01); *A63B 2230/06* (2013.01); *A63B 2230/60* (2013.01); *A63B 2230/70* (2013.01); *A63B 2243/007* (2013.01); *A63B 2243/0025* (2013.01); *A63B 2243/0037* (2013.01); *A63B 2243/0054* (2013.01); *A63B 2243/0066* (2013.01); *A63B 2243/0095* (2013.01); *A63B 2244/102* (2013.01); *A63B 2244/18* (2013.01); *A63B 2244/19* (2013.01); *A63B 2244/20* (2013.01); *A63B 2244/203* (2013.01); *H04B 1/04* (2013.01); *H04L 67/10* (2013.01); *H04N 7/18* (2013.01); *H04W 88/02* (2013.01)

(56) References Cited

U.S. PATENT DOCUMENTS

| | | | |
|---|---|---|---|
| 6,720,984 B1* | 4/2004 | Jorgensen | G06F 3/015 600/300 |
| 7,762,945 B2 | 7/2010 | Blumenthal | |
| 8,096,654 B2 | 1/2012 | Amirparviz | |
| 8,265,949 B2 | 9/2012 | Haddad | |
| D701,206 S | 3/2014 | Luckey | |
| 8,711,495 B2 | 4/2014 | Topliss | |
| 8,747,336 B2* | 6/2014 | Tran | G06F 19/3418 600/300 |
| 8,947,456 B2 | 2/2015 | Chen | |
| 8,950,867 B2 | 2/2015 | Macnamara | |
| 2002/0065121 A1* | 5/2002 | Fukunaga | A63F 13/08 463/8 |
| 2004/0132439 A1 | 7/2004 | Tyagi | |
| 2005/0134440 A1* | 6/2005 | Breed | B60N 2/2863 340/435 |
| 2006/0160616 A1* | 7/2006 | Kato | A63F 13/10 463/30 |
| 2006/0166737 A1* | 7/2006 | Bentley | A61B 5/1122 463/30 |
| 2007/0005609 A1* | 1/2007 | Breed | B60N 2/2863 |
| 2007/0109111 A1* | 5/2007 | Breed | B60N 2/2863 340/435 |
| 2008/0062338 A1 | 3/2008 | Herzog | |
| 2010/0144414 A1* | 6/2010 | Edis | A63B 24/0006 463/8 |
| 2012/0144554 A1* | 6/2012 | Thellmann | A63B 21/065 2/161.1 |
| 2012/0193806 A1 | 8/2012 | Orbach | |
| 2013/0044042 A1 | 2/2013 | Olsson | |
| 2013/0066448 A1* | 3/2013 | Alonso | H04Q 9/00 700/91 |
| 2013/0125027 A1 | 5/2013 | Abovitz | |
| 2014/0002472 A1 | 1/2014 | Sobeski | |
| 2014/0003762 A1 | 1/2014 | Macnamara | |
| 2014/0071539 A1 | 3/2014 | Gao | |
| 2014/0072278 A1* | 3/2014 | Kramer | H04N 5/23296 386/240 |
| 2014/0073481 A1* | 3/2014 | Aibara | A63B 24/0084 482/1 |
| 2014/0222462 A1 | 8/2014 | Shakil | |
| 2014/0267420 A1 | 9/2014 | Schowengerdt | |
| 2014/0306866 A1 | 10/2014 | Miller | |
| 2014/0347491 A1 | 11/2014 | Connor | |
| 2015/0016777 A1 | 1/2015 | Abovitz | |
| 2015/0148650 A1 | 5/2015 | Pugh | |
| 2015/0161821 A1 | 6/2015 | Mazula | |
| 2015/0283450 A1* | 10/2015 | McRoberts | G06Q 10/10 473/470 |
| 2015/0360080 A1* | 12/2015 | Hadaschik | G01P 7/00 73/865.4 |
| 2016/0055422 A1* | 2/2016 | Li | G05B 15/02 706/12 |
| 2016/0077593 A1* | 3/2016 | Zuger | G06F 1/163 345/173 |

\* cited by examiner

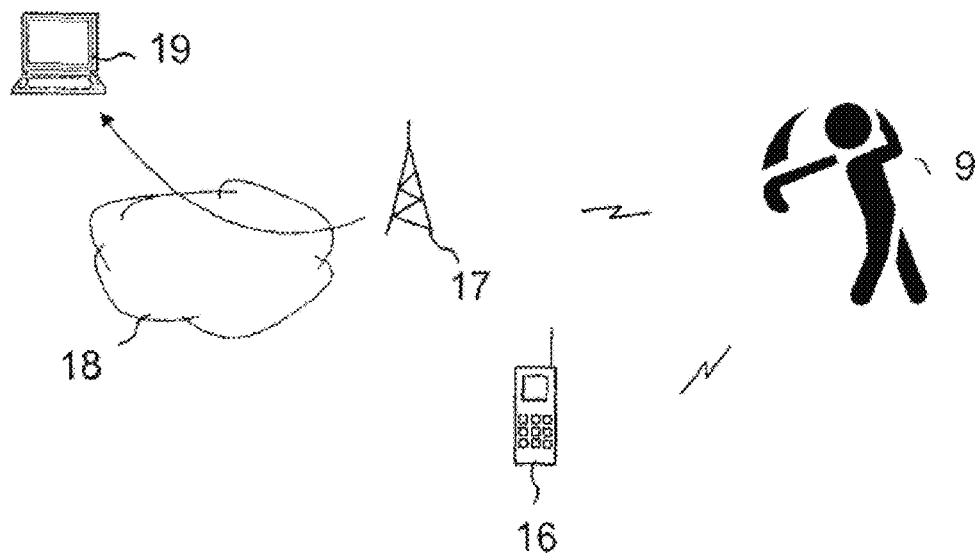
FIG. 1A
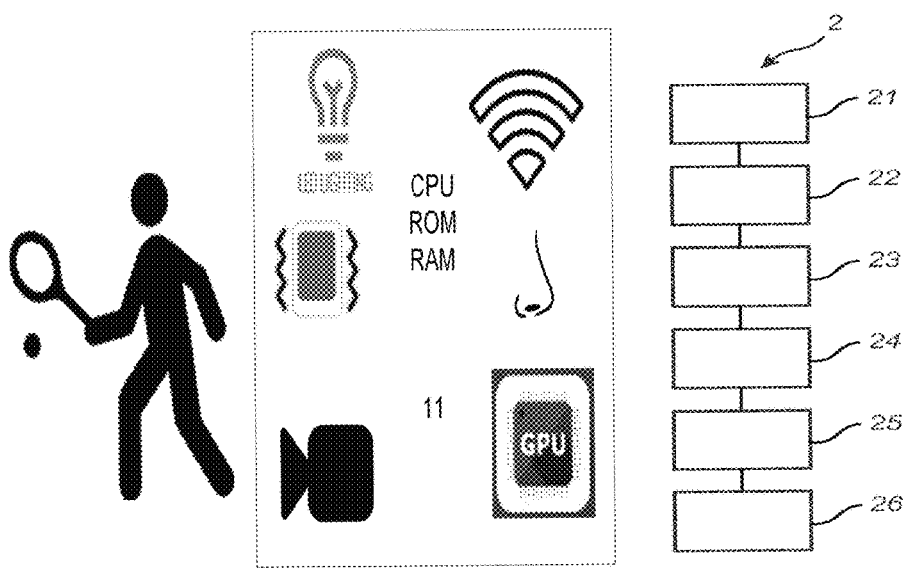
FIG. 1B
FIG. 1C

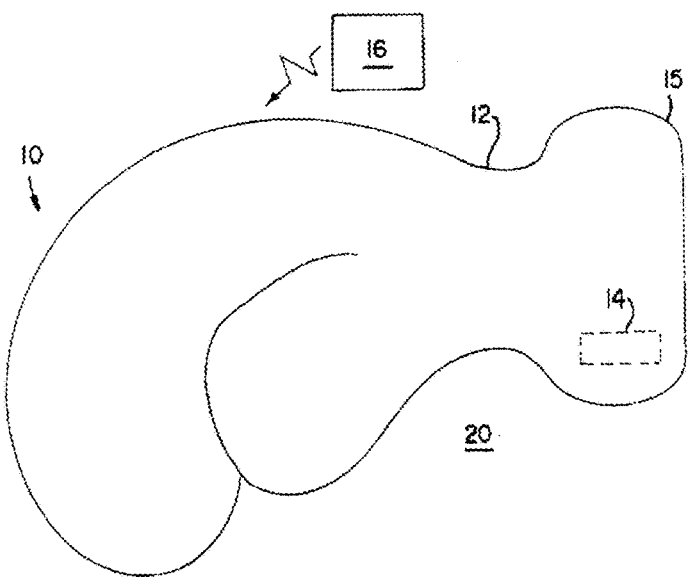
FIG. 7
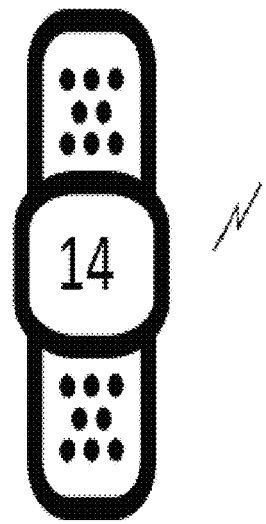
FIG. 8
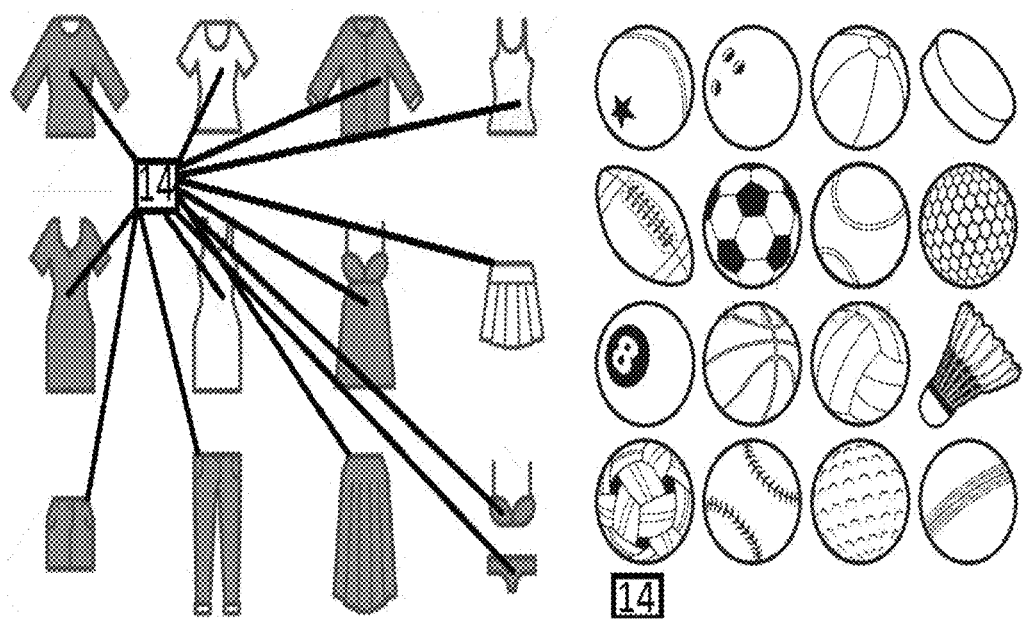
FIG. 9
FIG. 10

SMART DEVICE

BACKGROUND

The present invention relates to the Internet of Things (IoT).

SUMMARY

In one aspect, an Internet of Thing (IoT) device includes a processor coupled to a wireless transceiver; a camera; an accelerometer to detect acceleration of the device; and a module to follow a third-party motion or another device motion based on camera and accelerometer outputs.

These and other features of the present invention will become readily apparent upon further review of the following specification and drawings.

BRIEF DESCRIPTION OF THE DRAWINGS

FIG. 1A illustrates an exemplary environment for communicating data from a monitoring device to external computers FIG. 1B is a perspective view of an exemplary IoT device system.

FIG. 1C is an exemplary process supported by the device according to the present invention.

FIG. 7 shows an exemplary glove,

FIG. 8 shows an exemplary smart band,

FIG. 9 shows exemplary smart clothing,

FIG. 10 shows exemplary smart balls.

FIG. 11A shows exemplary smart rackets while

FIG. 12A-12B show exemplary protective gears, while

FIG. 16A-16C shows exemplary coaching system for skiing, bicycling, and weightlifting/free style exercise, respectively, while

Similar reference characters denote corresponding features consistently throughout the attached drawings.

DETAILED DESCRIPTION OF THE PREFERRED EMBODIMENTS

Figure 2A:
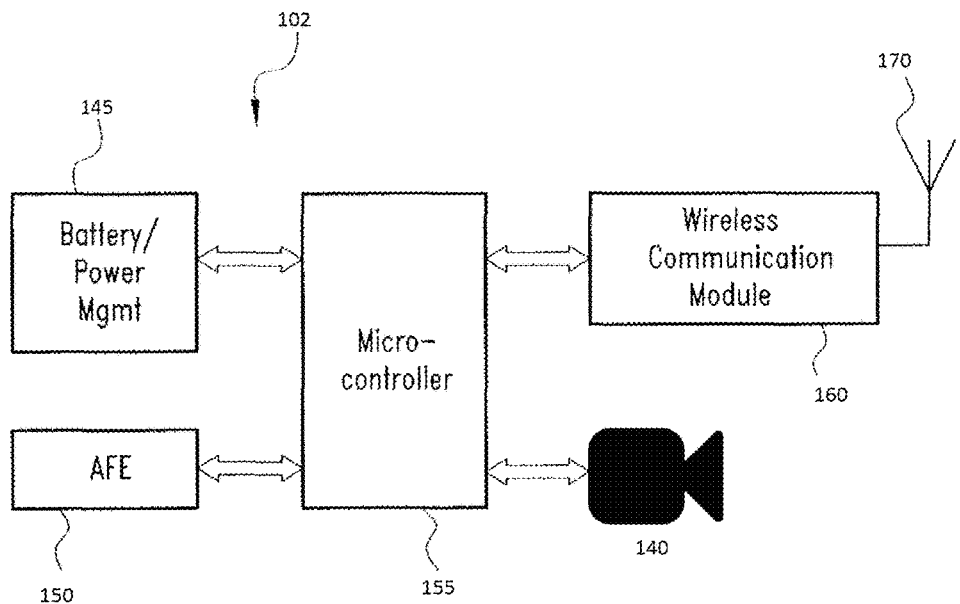
FIG. 2A is a block diagram of an electronic circuit for a smart device.

FIG. 1A illustrates an exemplary environment for communicating data from a monitoring device to external computers. In FIG. 1A, the monitoring device used for a device 9 includes an interface with a radio transmitter for forwarding the result of the comparison to a remote device. In one example, the monitoring device may include an additional switch and user interface. The user interface may be used by the user in order to trigger transmission of the comparison of the hand or foot pattern reference data with the stroke patterns data to the remote device. Alternatively, the transmission may occur automatically each time the device has been used, or may be triggered by placing the device in a cradle or base. All parts of the monitoring device may be encapsulated with each other and/or may be integrated into or attached to the body of the device 9. Alternatively, a radio transmitter may be arranged separately from the other parts, for instance, in a battery charger, cradle or base of the device 9. In that example, the interface 7 may include contact terminals in the device 9, which are connected to the corresponding terminals in the battery charger for forwarding the result of the comparison via a wired connection to the transmitter in the battery charger or may be connected by induction or short range wireless communications. The radio transmitter in the battery charger then transmits this comparison result further via the wireless radio connection to the remote device. In FIG. 1A, the remote device may be a mobile phone 16, PDA or computer 19, which receives the information directly from the monitoring device via a short range radio connection, as one example of a transmitter, such as a Bluetooth or a Wifi or a Zigbee connection. In one example, the user of the remote device may receive information about how thoroughly the device 9 has been used or the need to provide a replacement device. FIG. 1A also illustrates an alternate example of a transmitter, using an intermediate receiver 17 and a network 18, such as a cellular radio system. Also in this example, the radio transmitter may be located in connection with the device 9 or alternatively in connection, with a charger, cradle or base station of the device 9. In such an example, the comparison result may be transmitted via an intermediate receiver 17 and the network 18 to a remote device 19, 16 located further away than the range of a short range radio system, for example. The remove device 19, 16 may be any device suitable for receiving the signals from the network 18 and providing feedback on an output device. The transmission of information via a cellular radio system to the remote device may allow an advertiser provide an advertisement. For example, an advertisement may be added to the comparison result using network elements in the cellular radio system. The user may receive an advertisement with the comparison result. An advantage with such a solution is that the advertiser may provide revenue offsetting all or a portion of the cost for the transmission of the comparison result from the device 9 to the remote device 19, 16.

FIG. 1B shows a block diagram of the unit 9 with processor/RAM/ROM 11. The unit 9 includes a motion sensor, a multi-axis accelerometer, and a strain gage 42. The multi-axis accelerometer may be a two-axis or three-axis accelerometer. Strain gage 21 is mounted in the neck of the racket, and measures force applied to the ball, i.e., force in a z direction. Acceleration and force data are acquired by the microprocessor at a data acquisition rate (sampling rate) of from about 10 to 50 samples/second, e.g., about 20 samples/second. The acceleration data is used to infer motion, using an algorithm discussed below; it is not converted to position data. In this embodiment, because the sensors and strain gage are not in the head region, the head can be removable and replaceable, e.g., by threaded engagement with the handle (not shown), so that the device can continue to be used after instrument wear has occurred. Any desired type of removable head or cartridge can be used.

The unit 11 also includes a camera, which can be a 360 degree camera. Alternatively, the camera can be a 3D camera such as the Kinect camera or the Intel RealSense camera for ease of generating 3D models and for detecting distance of objects. To reduce image processing load, each camera has a high performance GPU to perform local processing, and the processed images, sound, and odor data are uploaded to a cloud storage for subsequent analysis.

The unit 11 includes an electronic nose to detect odor. The electronic nose can simply be a MEMS device acting as a particle counter. An embodiment of the electronic nose can be used that includes a fan module, a gas molecule sensor module, a control unit and an output unit. The fan module is used to pump air actively to the gas molecule sensor module. The gas molecule sensor module detects the air pumped into by the fan module. The gas molecule sensor module at least includes a gas molecule sensor which is covered with a compound. The compound is used to combine preset gas molecules. The control unit controls the fan module to suck air into the electronic nose device. Then the fan module transmits an air current to the gas molecule sensor module to generate a detected data. The output unit calculates the detected data to generate a calculation result and outputs an indicating signal to an operator or compatible host computer according to the calculation result.

An electronic tongue sensor can be provided to sense quality of sweat or liquid. The tongue includes a liquid molecule sensor module, a control unit and an output unit. Body liquid is applied or swiped on to the liquid molecule sensor module. The molecule sensor module detects the liquid molecules pumped into by the stirring module. The liquid molecule sensor module at least includes a molecule sensor which is covered with a compound. The compound is used to combine preset liquid molecules. The control unit controls the stirring module to pump liquid to be "tasted" into the electronic tongue device. Then the module transmits a flow current to the liquid molecule sensor module to generate a detected data. The output unit calculates the detected data to generate a calculation result and outputs an indicating signal to an operator or compatible host computer according to the calculation result. Such electronic tongue can detect quality of fog or liquid, among others.

In one embodiment for analyzing tooth structure, restorative materials within a tooth structure, and disease states of a tooth, the unit 11 includes a probe 20 which may be attached to a variety of probes, and instruments to afford adaptability to a variety of situations in providing diagnostic information on an object such as a naturally occurring structure, man-made materials placed or found within the structure, diseased or otherwise affected, infected or effected structure, as well as structure that has been eroded, worn by attrition, abraded, abfracted, fractured, crazed, broken or otherwise compromised through enthusiast use, misuse, fatigue or longevity of use. The probe 20 generates electrical outputs which are interpreted by a smart phone or computer.

In one embodiment, the probe 20 can be a vibratory transducer that sends out vibrations at known frequency and amplitude. The probe 20 also includes a receiver which can be an accelerometer, for example. The accelerometer is attached to the teeth and connected to a computer. The accelerometer digitizes the received vibrations and provides them into the phone or computer. The transducer can be a single piezoelectric transducer or an array with elements arranged to fit in a mouthpiece or an appliance to be worn over the oral arch. The transducer elements can be mounted in silicone rubber or other material suitable for damping mechanical coupling between the elements. Other materials may also be used for the array construction. For example, the transducer may be formed from one or more pieces of piezocomposite material, or any material that converts electrical energy to acoustic energy. The receiver can also be positioned to fit in the mouthpiece or appliance. One embodiment of the receiver is an accelerometer, but a suitable piezoelectric transducer can serve as the receiver as well. The software in the computer compares these inputs to known vibration responses corresponding to striking states on a ball or object. The computer 30 displays a response on the computer screen for that user.

FIG. 1C schematically shows a method or app 2 which may be implemented by the computing unit 11 shown in FIG. 1B. For example, the app 2 may be a computer implemented method. A computer program may be provided for executing the app 2. The app 2 includes code for:

(21) capture user motion with accelerometer or gyroscope
(22) capture VR views through camera and process using GPU
(23) capture user emotion using facial recognition or GSR
(24) model user action using kinematic model
(25) compare user action with idea action
(26) coach user on improvement to user techniques.

As shown in FIG. 2A, a microcontroller 155 receives and processes signals from the sensor 112-114, and converts those signals into an appropriate digital electronic format. The microcontroller 155 wirelessly transmits tension information in the appropriate digital electronic format, which may be encoded or encrypted for secure communications, corresponding to the sensed traffic and/or crime indication through a wireless communication module or transceiver 160 and antenna 170. Optionally, a camera 140 can be provided to visually detect traffic and/or crime and movement of the structure. While monitoring of the smart device 100 traffic and/or crime is continuous, transmission of tension information can be continuous, periodic or event-driven, such as when the tension enters into a warning or emergency level. Typically the indicated tension enters a warning level, then an emergency level as tension drops below the optimal range, but corresponding warning and emergency levels above the optimal range can also be used if supported by the smart device 100. The microcontroller 155 is programmed with the appropriate warning and emergency levels, as well as internal damage diagnostics and self-recovery features.

The tension information can take any form, including a simple warning/emergency indication that the tension is approaching or exceeding tension specifications, respectively. While under-tension is known to be the primary cause of structural or mechanical problems associated with devices, over-tension can also be a problem and can also be reported by the smart device 100.

The sensors can detect force, load, tension and compression forces on the device such as the device. Other data includes Acceleration; Velocity; Global absolute displacement; Local relative displacement; Rotation; Strain; Stress; Force; and Static-position video. Wind speed/direction; External temperature; weather parameters (rainfall, humidity, solar radiation, etc.); Internal or structural temperature; Mass loading (occupant count, etc.); Static tilt; Fatigue damage; Corrosion; Acoustic emission; and Moving-position video. A force is simply a push or pull to an object and can be detected by a load cell, pressure cell or strain sensor. A Load: Is simply a force applied to a structure. Ex: weight of vehicles or pedestrians, weight of wind pushing on sides.

Tension & Compression are internal forces that make a member longer or shorter. Tension stretches a member and Compression pushes the member closer together. Acceleration can also be detected by Force-Balance (Servo) Piezoelectric Piezoresistive MEMS. Velocity can be measured by force-balance (servo) MEMS, or Mechanical Doppler Heated wire. A local Displacement sensor can be LVDT/ Cable potentiometer Acoustic Optical/laser Temperature Electrical Optical fiber. A rotation sensor can be Gyro MEMS Gyro Tilt Electro-mechanical MEMS. A strain sensor can be a resistance gauge Vibrating wire Optical fiber Corrosion Electrical Chemical sensors. A traffic and/or crime sensor can be a microphone listening to acoustic emission, or Piezoelectric MEMS, for example, and sonar sound processing can be used to detect where crime activity is coming from.

The sensor 112-114, transceiver 160/antenna 170, and microcontroller 155 are powered by and suitable power source, which may optionally include an electromagnetic field (EMF) scavenging device 145, such as those known in the art, that convert ambient EMF (such as that emitted by radio station broadcasts) into small amounts of electrical power. The EMF scavenging device 145 includes a battery to buffer and store energy for the microcontroller 155, sensor 112-114, camera 140 and wireless communications 160/170, among others.

The circuit of FIG. 2A contains an analog front-end ("AFE") transducer 150 for interfacing signals from the sensor 112-114 to the microcontroller 155. The AFE 150 electrically conditions the signals coming from the sensor 112-114 prior to their conversion by the microcontroller 155 so that the signals are electrically compatible with the specified input ranges of the microcontroller 155. The microcontroller 155 can have a CPU, memory and peripheral circuitry. The microcontroller 155 is electrically coupled to a wireless communication module 160 using either a standard or proprietary communication standard. Alternatively, the microcontroller 155 can include internally any or all circuitry of the smart device 100, including the wireless communication module 160. The microcontroller 155 preferably includes power savings or power management circuitry 145 and modes to reduce power consumption significantly when the microcontroller 155 is not active or is less active. The microcontroller 155 may contain at least one Analog-to-Digital Converter (ADC) channel for interfacing to the AFE 150.

The battery/power management module 145 preferably includes the electromagnetic field (EMF) scavenging device, but can alternatively run off of previously stored electrical power from the battery alone. The battery/power management module 145 powers all the circuitry in the smart device 100, including the camera 140, AFE 150, microcontroller 155, wireless communication module 160, and antenna 170. Even though the smart device 100 is preferably powered by continuously harvesting RF energy, it is beneficial to minimize power consumption. To minimize power consumption, the various tasks performed by the circuit should be repeated no more often than necessary under the circumstances.

Stress information from the smart device 100 and other information from the microcontroller 155 is preferably transmitted wirelessly through a wireless communication module 160 and antenna 170. As stated above, the wireless communication component can use standard or proprietary communication protocols. Smart lids 100 can also communicate with each other to relay information about the current status of the structure or machine and the smart device 100 themselves. In each smart device 100, the transmission of this information may be scheduled to be transmitted periodically. The smart lid 100 has a data storage medium (memory) to store data and internal status information, such as power levels, while the communication component is in an OFF state between transmission periods. On the other hand, once the communication commences in the ON state, the microcontroller 155 can execute the following tasks:

1. Neighbor discovery: in this task each smart device 100 sends a beacon identifying its location, capabilities (e.g. residual energy), status. 2. Cluster formation: cluster head will be elected based on the findings in (1). The cluster children communicate directly with their cluster head (CH). 3. Route discovery: this task interconnects the elected cluster heads together and finds the route towards the sink smart device (node) so that minimum energy is consumed. 4. Data transmission: the microcontroller processes the collected color data and based on the adopted data dissemination approach, the smart device 100 will do one of the following. (a) Transmit the data as is without considering the previous status; or (b) transmit the data considering the previous status. Here we can have several scenarios, which include: (i) transmitting the data if the change in reported tension exceeds the warning or emergency levels; and (ii) otherwise, do not transmit.

Figure 2B:
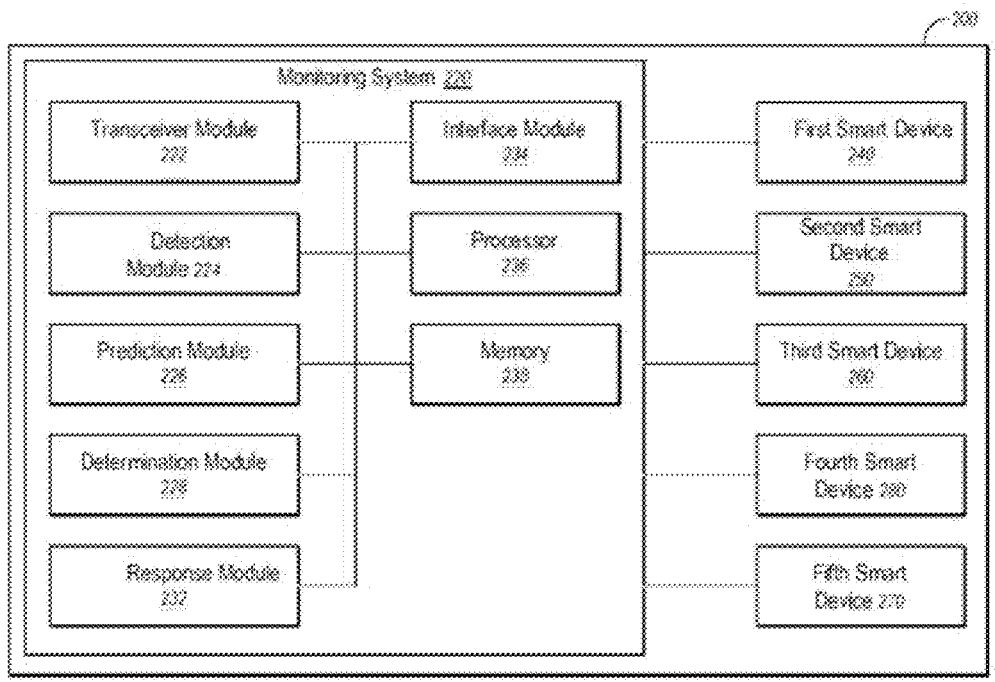
FIG. 2B is a block diagram of a big data system for predicting stress experienced by a structural unit such as a bridge, a building, or a plane, for example.

The electronic of FIG. 2A operates with a big data discovery system of FIG. 2B that determines events that may lead to failure. FIG. 2B is a block diagram of an example stress monitoring system 200 that may be process the stress detected by the smart device 100 of FIG. 1, arranged in accordance with at least some embodiments described herein. Along with the stress monitoring system 220, a first smart device such as a smart device 240, a second smart device 250, a third smart device 260, a fourth smart device 280, and additional sensors 270 may also be associated with the unit 200. The stress monitoring system 220 may include, but is not limited to, a transceiver module 222, a stress detection module 224, a stress prediction module 226, a determination module 228, a stress response module 232, an interface module 234, a processor 236, and a memory 238.

The transceiver module 222 may be configured to receive a stress report from each of the first, second, and third smart devices 240, 250, 260. In some embodiments, the transceiver module 222 may be configured to receive the stress reports over a wireless network. For example, the transceiver module 222 and the first, second, and third smart devices 240, 250, 260 may be connected over a wireless network using the IEEE 802.11 or IEEE 802.15 standards, for example, among potentially other standards. Alternately or additionally, the transceiver module 222 and the first, second, and third smart devices 240, 250, 260 may communicate by sending communications over conductors used to carry electricity to the first, second, and third smart devices 240, 250, 260 and to other electrical devices in the unit 200. The transceiver module 222 may send the stress reports from the first, second, and third smart devices 240, 250, 260 to the prediction module 226, the stress detection module 224, and/or the determination module 228.

The stress module 224 may be configured to detect stress on the object as detected by the devices 100. The signal sent by the devices 100 collectively may indicate the amount of stress being generated and/or a prediction of the amount of stress that will be generated. The stress detection module 224 may further be configured to detect a change in stress of non-smart devices associated with the unit 200.

The prediction module 226 may be configured to predict future stress based on past stress history as detected, environmental conditions, forecasted stress loads, among other factors. In some embodiments, the prediction module 226 may predict future stress by building models of usage and weight being transported. For example, the prediction module 226 may build models using machine learning based on support vector machines, artificial neural networks, or using other types of machine learning. For example, stress may correlate with the load carried by a bridge or an airplane structure. In other example, stress may correlate with temperature cycling when a structure is exposed to constant changes (such as that of an airplane).

The prediction module 226 may gather data for building the model to predict stress from multiple sources. Some of these sources may include, the first, second, and third smart devices 240, 250, 260; the stress detection module 224; networks, such as the World Wide Web; the interface module 234; among other sources. For example, the first, second, and third smart devices 240, 250, 260 may send information regarding human interactions with the first, second, and third smart devices 240, 250, 260. The human interactions with the first, second, and third smart devices 240, 250, 260 may indicate a pattern of usage for the first, second, and third smart devices 240, 250, 260 and/or other human behavior with respect to stress in the unit 200.

In some embodiments, the first, second, and third smart devices 240, 250, 260 may perform predictions for their own stress based on history and send their predicted stress in reports to the transceiver module 222. The prediction module 226 may use the stress reports along with the data of human interactions to predict stress for the system 200. Alternately or additionally, the prediction module 226 may make predictions of stress for the first, second, and third smart devices 240, 250, 260 based on data of human interactions and passed to the transceiver module 222 from the first, second, and third smart devices 240, 250, 260. A discussion of predicting stress for the first, second, and third smart devices 240, 250, 260 is provided below with respect to FIGS. 5 and 6.

The prediction module 224 may predict the stress for different amounts of time. For example, the prediction module 224 may predict stress of the system 200 for 1 hour, 2 hours, 12 hours, 1 day, or some other period. The prediction module 224 may also update a prediction at a set interval or when new data is available that changes the prediction. The prediction module 224 may send the predicted stress of the system 200 to the determination module 228. In some embodiments, the predicted stress of the system 200 may contain the entire stress of the system 200 and may incorporate or be based on stress reports from the first, second, and third smart devices 240, 250, 260. In other embodiments, the predicted stress of the system 200 may not incorporate or be based on the stress reports from the first, second, and third smart devices 240, 250, 260.

The determination module 228 may be configured to generate a unit stress report for the system 200. The determination module 228 may use the current stress of the system 200, the predicted stress of the system 200 received from the prediction module 224; stress reports from the first, second, and/or third smart devices 240, 250, 260, whether incorporated in the predicted stress of the system 200 or separate from the predicted stress of the system 200; and an amount of stress generated or the predicted amount of stress, to generate a unit stress report.

In some embodiments, one or more of the stress reports from the first, second, and/or third smart device 240, 250, 260 may contain an indication of the current operational profile and not stress. In these and other embodiments, the determination module 228 may be configured to determine the stress of a smart device for which the stress report indicates the current operational profile but not the stress. The determination module 228 may include the determined amount of stress for the smart device in the unit stress report. For example, both the first and second smart device 240, 250 may send stress report. The stress report from the first smart device 240 may indicate stress of the first smart device 240. The stress report from the second smart device 250 may indicate the current operational profile but not the stress of the second smart device 250. Based on the current operational profile of the second smart device 250, the determination module 228 may calculate the stress of the second smart device 250. The determination module 228 may then generate a unit stress report that contains the stress of both the first and second smart devices 240, 250.

In some embodiments, the stress monitoring system 220 may not include the prediction module 226. In these and other embodiments, the determination module 228 may use stress reports from the first, second, and/or third smart devices 240, 250, 260, with the received amount of stress inferred on non-smart devices, if any, to generate the unit stress report. The determination module 228 may send the unit stress report to the transceiver module 222.

In some embodiments, the processor 236 may be configured to execute computer instructions that cause the stress monitoring system 220 to perform the functions and operations described herein. The computer instructions may be loaded into the memory 238 for execution by the processor 236 and/or data generated, received, or operated on during performance of the functions and operations described herein may be at least temporarily stored in the memory 238.

Although the stress monitoring system 220 illustrates various discrete components, such as the prediction module 226 and the determination module 228, various components may be divided into additional components, combined into fewer components, or eliminated, depending on the desired implementation. In some embodiments, the unit 200 may be associated with more or less smart devices than the three smart devices 240, 250, 260 illustrated in FIG. 2.

Figure 3:
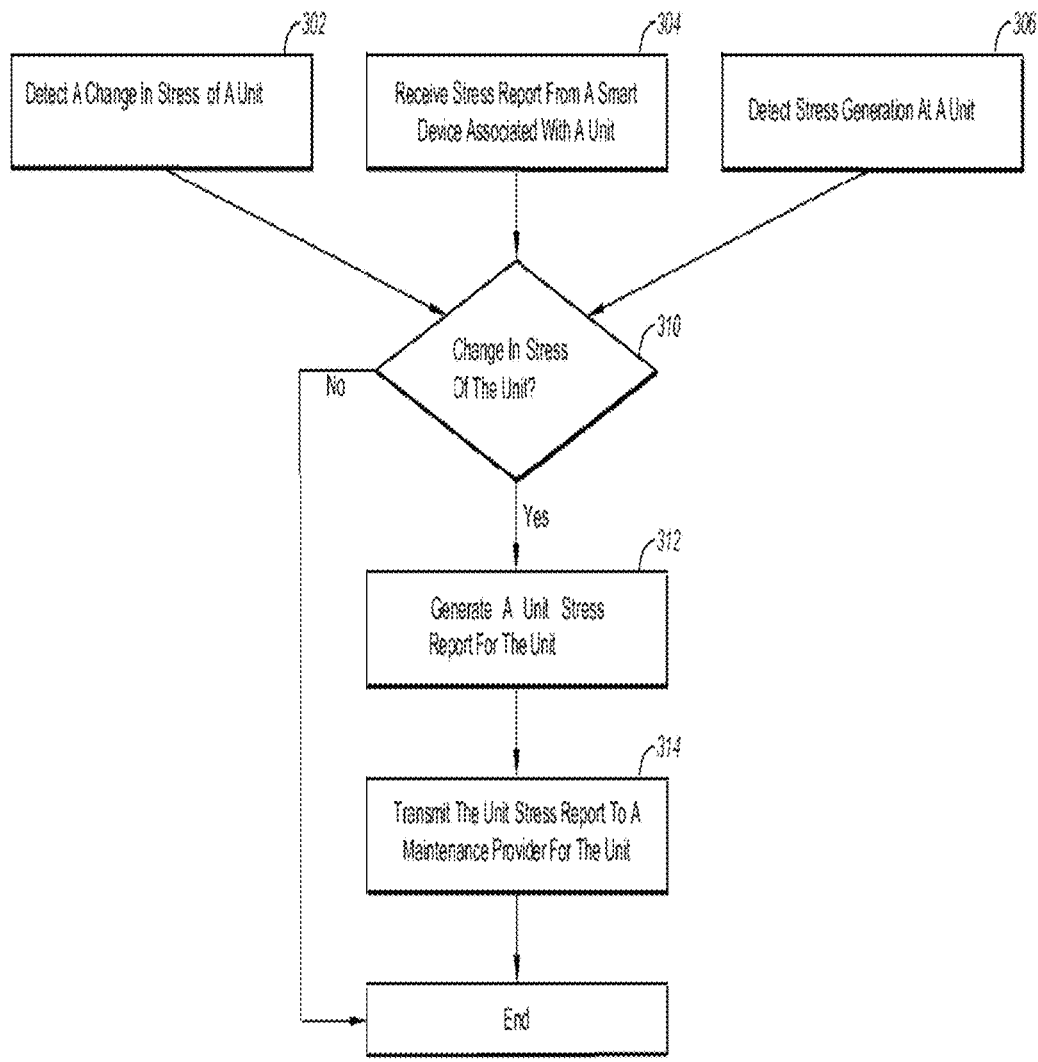
FIG. 3 is a flowchart illustrating one operation of the system of FIG. 2A-2B in detecting stress on a unit.

FIG. 3 is a flow chart of an example method 300 of monitoring stress of a or game unit, arranged in accordance with at least some embodiments described herein. The method 300 may be implemented, in some embodiments, by an stress monitoring system, such as the stress monitoring system 220 of FIG. 2. For instance, the processor 236 of FIG. 2B may be configured to execute computer instructions to perform operations for monitoring stress as represented by one or more of blocks 302, 304, 306, 310, 312, and/or 314 of the method 300. Although illustrated as discrete blocks, various blocks may be divided into additional blocks, combined into fewer blocks, or eliminated, depending on the desired implementation.

The method 300 may begin at one or more of blocks 302, 304, and/or 306. The blocks 302, 304, and/or 306 may occur at the same time or at different times and may or may not depend on one another. Furthermore, one or more of the block 302, 304, 306 may occur during the method 300. For example, the method 300 may complete when blocks 304, 310, and 312 occurs and without the occurrence of block 302 and 306.

In block 302, a change in stress of a device (device or beam) associated with a unit may be detected. A non-smart device may by any device that receives stress and does not generate an stress report indicating its stress, for example a legacy racket without IoT electronics. A change in the stress of a non-smart device may be detected using an stress detection module and/or usage meter associated with the unit, such as the stress detection module 224 and/or the smart device 100. For example, non-smart device stress can be estimated by the load the unit carries, the temperature cycling experienced by the unit, for example.

After a change in stress of the non-smart device is detected, the method 300 proceeds to block 310. In block 304, an stress report from a smart device such as the smart device 100 associated with the unit may be received. A smart device may be a device that detects stress and generates and transmits an stress report indicating the stress on the smart device. The stress report may indicate predicted future stress of the smart device. In some embodiments, an stress report may be received at set intervals from the smart device regardless of a change in the stress report. Alternately or additionally, a stress report may be received after a change in the stress of the smart device results in a change to the stress report. After a stress report is received from the smart device, the method 300 proceeds to block 310.

In block 306, stress experienced at the unit may be detected. Stress at the unit may be detected using a stress detection module, such as the stress detection module 224 of FIG. 2B. After detecting stress at the unit, the method proceeds to block 310. At block 310, it is determined if a change in the stress occurred. For example, if an increase in stress occurs at the same time and at the same amount as an increase in the stress of a non-smart device, a change in the stress may not occur. If a change in the stress occurs, the method 300 proceeds to block 312. If no change occurs, the method 300 ends.

At block 312, a unit stress report is generated for the unit. In some embodiments, the unit stress report may indicate the current stress of the unit. Alternately or additionally, the unit stress report may indicate a current and predicted future stress of the unit. At block 314, the unit stress report is transmitted to a maintenance provider. In some embodiments, the unit stress report may be transmitted when the unit stress report indicates a change in stress for the unit that is greater than a predetermined threshold. If the unit stress report indicates a change in stress for the unit that is less than the predetermined threshold, the unit stress report may not be transmitted to the provider of maintenance services.

Figure 5:
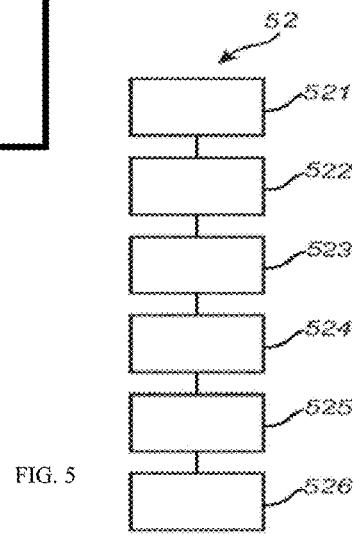
FIG. 5 shows an exemplary process for augmented and/or virtual reality for viewers participating in a game.

FIG. 5 shows in more details the computer 30 and the interface to the probe 20. An amplifier 90 amplifies vibratory output from a transducer 92. A pick up unit having an accelerometer (or an array) 96 receives reflected vibrations from user arm or leg 94, among others. A computer 98 includes a digital converter to digitize output from the pick-up unit and software on the computer 98 can process the captured diagnostic data. Diagnostic software 100 can include a database of known restorations, diseases, and tissue conditions whose signatures can be matched against the capture diagnostic data, and the result can be displayed on a screen for review by the athlete.

Included in one embodiment of the instrumentation is the transmitter or transducer, which will emit the vibrations that will be imparted to the teeth and jaws. This will be connected to a power supply and amplifier, which will allow for a frequency range. On electrical excitation, the transducer emits an outgoing vibration. That vibration will then travel into the arm or leg and down is root into the soft tissues and out into the bones or jaws. The accelerometer or detector will be placed on the bone of interest. It will receive the vibrations from the emitter. The effect of the vibrations on the muscle of interest will generate a pattern of frequency vibrations. Those vibrations will be digitally converted and analyzed against known dental states in the software of the computer. As the data is collected various linear samplings and comparisons will be made against the database. Software will make these comparisons as the data is received from the teeth.

FIG. 5 schematically shows a method or app 52 to perform collaborative VR/AR gaming. The app 52 includes code for:

(51) capture 360 degree view of the live event
(52) detect head position of the viewer
(53) adjust viewing angle on screen based on head position and user posture
(54) render view to simulate action based on user control rather than what the professional is doing
(55) augment view with a simulated object that is powered by viewer action as detected by sensors on viewer body
(56) compare professional result with simulated result and show result to a crowd of enthusiasts for social discussion.

Figure 4:
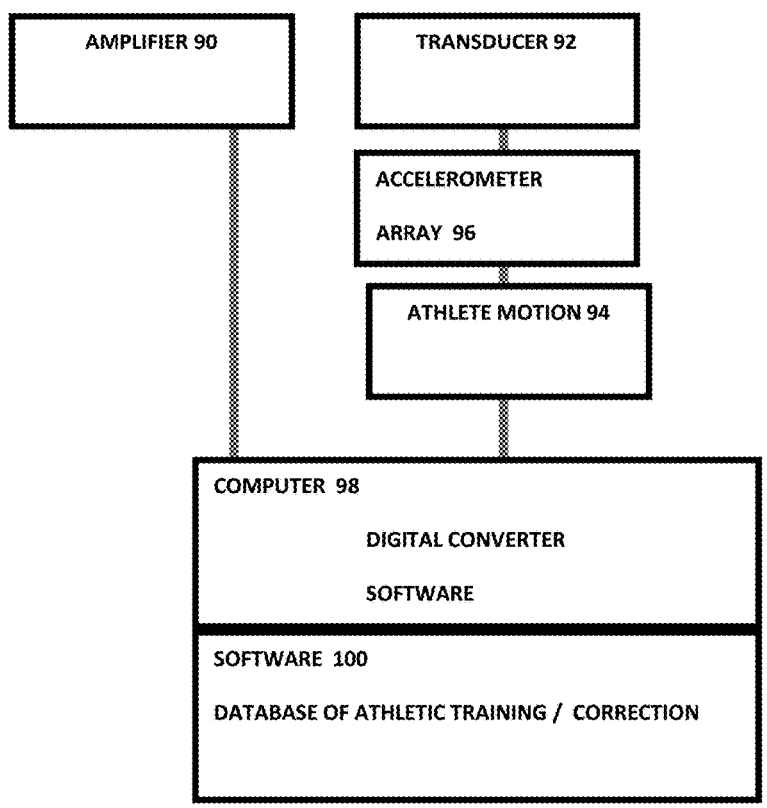
FIG. 4 shows an exemplary sports diagnosis and trainer system for augmented and/or virtual reality.
Figure 6:
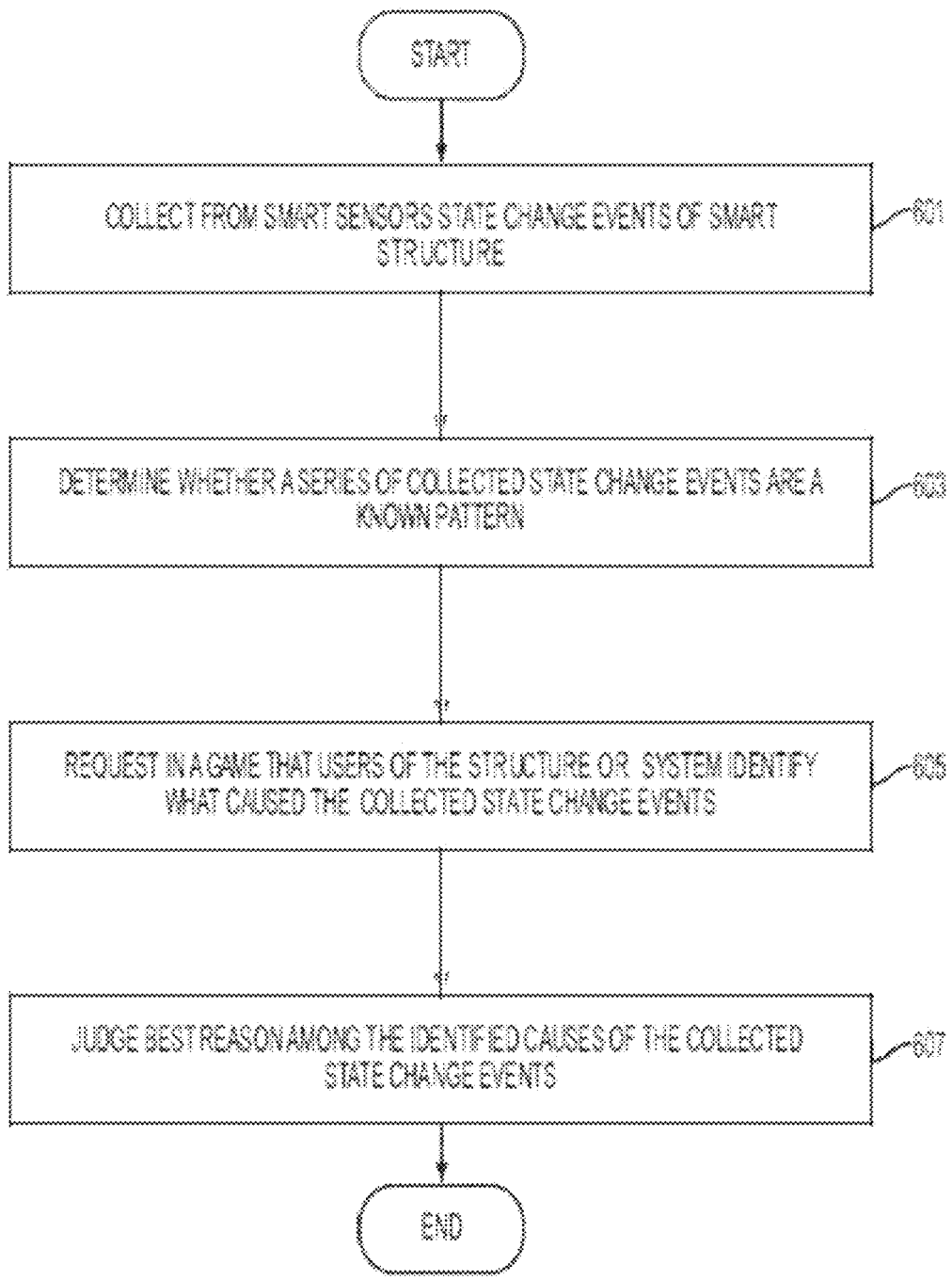
FIG. 6 shows an exemplary process to identify reasons for sensor data changes using a gaming process.

FIG. 6 is a flowchart of a method of an embodiment of the present disclosure. Referring to FIG. 6, a smart system may collect from smart devices state change events of a smart system in operation 601. That is, the smart system of FIG. 4 collects information on each of the group of devices, the smart devices, the smart appliances, the security devices, the lighting devices, the energy devices, and the like. The state change events indicate when there is a change in the state of the device or the surrounding environment. The state change events are stored by the smart system. In operation 603, the system may determine whether a series of the collected state change events are a known pattern. That is, the gateway determines whether there are events which have been correlated or identified in the past. If the collected state change events have been identified in the past, it may be necessary to determine that the smart systems trusts the identification the collected state change events. The trust factor of the identification of the collected state change events may be determined by the number of users who have identified the collected state change events or the number of time collected state change events have been repeated and identified. In operation 605, when the series of the collected state change events is an unknown pattern, request users of the smart system to identify what caused the collected state change events request. That is, the system transmits to a gamification application (hereinafter app) on the user's mobile device a request to identify the collected state change events. The gamification app displays the information and request the user enter information identifying the collected state change events. Each of the mobile devices transmits this information back to the system to the gamification module. In operation 605, the system transmits the each user's identified collected state change events to the other user's of the smart home system and they each vote on the best identification of the collected state change events. Thus, the identified collected change state events that have been repeatedly identified over a period of weeks increases, the trustworthiness of the identification increases. Likewise, if every user of the smart system makes the same identification of the collected change state events, the identified collected change state events may be considered trustworthy at point. Such a determination of a threshold for when the identified collected change state events are considered trustworthy and therefore need not be repeated, is made by a system administrator. However, it will be understood that such a trustworthiness of this type only gives higher confidence of this particular dataset at that point in time. As such further repetition is required, since the sensor data may have noise, the more datasets to be identified to the pattern, the more robust the trustworthiness will be. Until the robustness reaches a threshold, then the system can confirm this is a known trustworthy pattern.

The system can use gaming to help enthusiasts improve dental care or maintain teeth hygiene. This may involve use of virtual tools, corresponding to such tools used in normal dental hygiene: device, tooth picks, dental floss, gum massaging aids, etc. In this embodiment, the game may, for example, have the object of fighting tooth or gum decay, damage or infection which may be caused by carries or other infectious agents. The user is presented with a library of tools and has to select a tool to treat a certain developing virtual condition, e.g. carries or a gum infection. The game rules determine a certain continuous progress of infection which if not properly "treated" by the user will cause decay of one or more teeth, gum infection, potential bleeding, loss of teeth, etc. In step 13, the user may score points depending on his ability to choose the right tools to treat a particular condition or in avoiding a condition from developing. Next, it is determined whether the condition of the teeth is satisfactory. If yes, the process terminates. If no, then the user is prompted whether he wishes to select another tool. If no, the process terminates. If yes, the process restarts. Here again, the game, in addition to being amusing and providing an insight of the user into his own teeth, may be educational, particularly for children, on teeth oral hygiene methods and on the importance of maintaining oral hygiene.

In accordance with another embodiment of the invention the game may involve use of a variety of virtual imaginary tools such as virtual guns, wands, etc. in order to fight infectious agents of the teeth or gums.

Smart Glove

FIG. 7 shows an exemplary glove which can be thin to provide touch sensitivity or thick to provide shock protection for boxers. A body 12 of the boxing glove 10 includes an impact measuring device 14 is embedded within the glove 12 in an area protected from direct impact. Such an area includes the cuff 15 of the glove 12 or that portion of the glove 12 adjacent a user's palm, or adjacent an inside surface of a user's fingers. Placement of the impact measuring device 14 into the lining of the glove in such an area allows for the force of a blow to be measured without presenting a hazard to the recipient of the blow. Under the embodiment, an impact measuring device 14 would be included in the right glove 12 for a right handed fighter, or the left glove 12 for a left handed fighter. For fighters that are equally effective with both hands, or to improve monitoring accuracy, an impact measuring device 14 would be included in both gloves 12. The impact measuring system 20. The impact measuring system 20 includes an impact measuring device 14 and impact display unit 16. The impact measuring device 14 is linked to the impact display 28 via a radio frequency (rf) link 32. Under the embodiment, the impact measuring device 14 includes at least one 3-axis accelerometer. A thin version of the glove can be worn to detect a golf stroke or a tennis stroke with legacy clubs or rackets that lacks IoT intelligence.

Smart Band

FIG. 8 shows an exemplary stick on wearable monitoring device for sports and fitness applications. The wireless sensor electronics 14 is mounted on a band-aid in the example of FIG. 8. The band-aid can be removed upon completion of the sports event. The central patch can be recycled, and the adhesive portion can be disposed. While the embodiment is shown as a band-aid, the inventors contemplate that any suitable bands, straps, attachments can be used in lieu of the band-aid to attach the sensors to the body. For example, in Virtual Reality (VR) sports applications, sensors including gyroscopes and cameras can be positioned on various body portions to capture motion as well as eye tracking, mouth tracking, speech recognition, among others.

One embodiment uses Samsung's Bio-Processor which is an all-in-one health solution chip. By integrating not only Analog Front Ends (AFE), but also microcontroller unit (MCU), power management integrated circuit (PMIC), digital signal processor (DSP), and eFlash memory, it is able to process the bio-signals it measures without the need of external processing parts. Even with its integrated design, the Bio-Processor is particularly innovative thanks to its incredibly small size. When compared to the total area of the discrete parts, the Bio-Processor is only about one fourth of the total combined size, which is ideal for small wearable devices, offering a bounty of options when designing new devices. The Bio-Processor has five AFEs including bio-electrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively.

One embodiment provides a flexible and stretchable electronic patch that monitors impact or other events whereby a flexible substrate is geometrically patterned to allow the substrate to undergo substantial stretching and flexing while large regions of the substrate material experiences local strains much lower than the macroscopic applied strain. The geometric patterning of the substrate facilitates continuous low strain domains (LSDs) throughout the substrate—where low strain domains are defined as regions that experience strain levels (magnitude) lower than the macroscopic applied strain. Conventional electronic components can be mounted to the LSDs, and conventional metal traces can be routed through the LSDs, dramatically reducing the stresses transmitted to the components and traces by the substrate during stretching and flexing, and therefore reducing the potential for component debonding, trace cracking, and circuit failure. The geometrically patterned strain relief features (SRFs) are dispersed either regularly or irregularly throughout the substrate. The geometrically patterned SRF regions form "hinge-like" domains. During macroscopic deformation, the SRFs rotate, translate, open, close, or otherwise change shape, causing the "hinge-like" regions to deform, and the remaining larger LSD substrate regions to primarily rotate and translate. The SRFs are designed such that the "hinge-like" regions also exhibit relatively small strain compared to the macroscopic applied strain and thus enable conductive traces, such as copper or gold, to run through the hinges and maintain function during stretching, flexing and twisting of the patch. The substrate can be multilayered to enable running conductive traces, ground layers, vias, and/or components on/in multiple layers through the thickness of the overall substrate. The geometric patterning can be designed to enable different stretching, flexing and twisting, providing uniaxial, biaxial, and multi-axial stretchability or flexibility, and the ability to conform to a variety of surface curvatures. The geometrically patterned substrate offers a means of packaging complex multi-layered electronics designs for monitoring impact (and other) events onto a stretchable and flexible substrate enabling the device to dynamically stretch, bend, twist, and conform to arbitrary shapes. The stretchable, flexible geometrically structure electronics can be fabricated using the same technologies for conventional flexible circuit boards where the stretch-enabling patterning can be imparted at different stages in the fabrication process and can also be fabricated using emerging materials and fabrication methods. The Stretchable bandaid has the stretchable, flexible substrate described above with multiple LSDs for placement of electronic components (e.g., accelerometers, gyroscopes, pressure temperature, gas and fluid sensors, microprocessors, transceivers, GPS, clocks, actuators, vias, and batteries (or other energy source)) and multiple patterned hinge-like regions bridging the LSDs which enable the routing of conducting interconnecting traces. The SEHIM patch can take the form factor of a bandaid or bandage or other such wearable form factor. The geometric patterning provides stretch, flex and twist to conform to a body and stretch, flex and twist to move or deform with a body. The bandaid detects impact accelerations, using a 3-axis accelerometer and processes the raw acceleration data in the microprocessor. The processed data is stored in the microprocessor and later (or potentially in real time) transmitted via the Bluetooth to a smart phone, tablet or computer. This embodiment encompasses wireless communication but wired communication may be desirable in some applications and can be accommodated by this invention. The bandaid can be stretched, bent and twisted with the traces and components at low strains to maintain electrical function. In all cases there was effectively no strain on the components and solder joints. The bandaid can also possess an adhesive backing for direct adhesion to the head, body or object. The band can also be coated to provide both added comfort and protection against moisture, water, and other environmental factors. The band can also contain other sensors including gyroscopes, temperature and pressure sensors, moisture sensors, clocks, chemical and/or biological sensors, etc. Features of the smart band can include:

Smart Clothing

FIG. 9 shows an exemplary shirt based embodiment where sensors can be positioned anywhere on the shirt and when worn, can capture position, video, and vital signs. One embodiment uses Samsung's Bio-Processor to process the bio-signals it measures without the need of external processing parts with five AFEs including bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. Features of the smart clothe can include:

1. A smart clothing, comprising:
  a shirt, underwear, pant or sock;
  a band to be secured to the a shirt, underwear, pant or sock;
  a processor in the band and coupled to a wireless transceiver;
  an EKG amplifier coupled to the band;
  a sensor disposed in the band; and
  an accelerometer disposed within the band to detect acceleration of the band.
2. The clothing of claim 1, comprising a plurality of bands forming a mesh network and communicating episodically to conserve power.
3. The clothing of claim 1 where the electronic components, sensors, and interconnects of the patch monitor, record, process and/or transmit events of interest (such as accelerometers and gyroscopes for impact events, temperature sensors for temperature and/or temperature gradients, pressure sensors, moisture sensors, chemical sensors).
4. The clothing of claim 1 comprised for sensing and/or monitoring impact events where the sensors are accelerometers, gyroscopes, and/or pressure sensors.
5. The clothing of claim 1 comprised for sensing and/or monitoring and/or controlling ongoing events where the sensors monitor temperature, temperature gradients, motion, position, environmental or chemical levels, or other such information.
6. The clothing of claim 1 comprised for sensing events or other information including mounting multiple distributed sensors for obtaining spatial and/or temporal distribution in the data and/or multiple sensors sensing different information and data.
7. The clothing of claim 1 including wired or wireless communication, such as a Bluetooth module or a wi-fi module or other transmission module, transmitting and/or receiving information to/from another device.
8. The clothing of claim 1 with power and energy sources including batteries, wired or wireless rechargeable batteries, photovoltaics, thermoelectrics, or energy harvesters.
9. The clothing of claim 1 with an adhesive backing for directly adhering to a head, a body, or an object.
10. The clothing of claim 1 contained in an adhesive or a sleeve for adhering or attaching to a head, a body, or an object.
11. The clothing of claim 1 coated with a coating for protection against the elements (water, moisture, dirt, other) and/or for increased comfort to the wearer.
12. The clothing of claim 1, comprising a geometrically patterned substrate that contains regions of low strain domains (LSDs) bridged by hingeable strain relief features (SRFs) which also contain low strain regions and enable the stretching, flexing and twisting of the patch while maintaining continuous low strain regions for mounting electronic components and routing traces.
13. The clothing of claim 1 for attachment to or on or an object, or embedded in an object.
14. The clothing of claim 1 in the form factor of a rectangular or a square or a triangular or other polygon or circular or elliptical or other geometric shape bandage.
15. The clothing of claim 1 in the form factor that is or contains any combination of rectangles, triangles, circles, ellipses or other form factors.
16. The clothing of claim 1 with different geometric patterning of different numbers and shapes and orientations of low strain domains, different numbers and orientation of geometrically structured hinge-like domains, and different geometries of hinge-like domains.
17. The clothing of claim 1 as a programmable circuit board for arbitrary applications.
18. The clothing of claim 1 fabricated using current flex circuit manufacturing methods and materials.
19. The clothing of claim 1 comprising a cloud storage to receive sensor data.
20. The clothing of claim 1 where the polymer layers are current flex manufacturing polymers such as Kapton, polyimides, polyamides, polyesters, or other as well as elastomers such as silicone rubbers (PDMS) or polyurethanes or other elastomers and the interconnects are metals that have high electrical conductivity, such as copper or gold, or where the interconnects are emerging stretchable electronic materials and stretchable conductive inks and materials.

Smart Handle

Figure 11A:
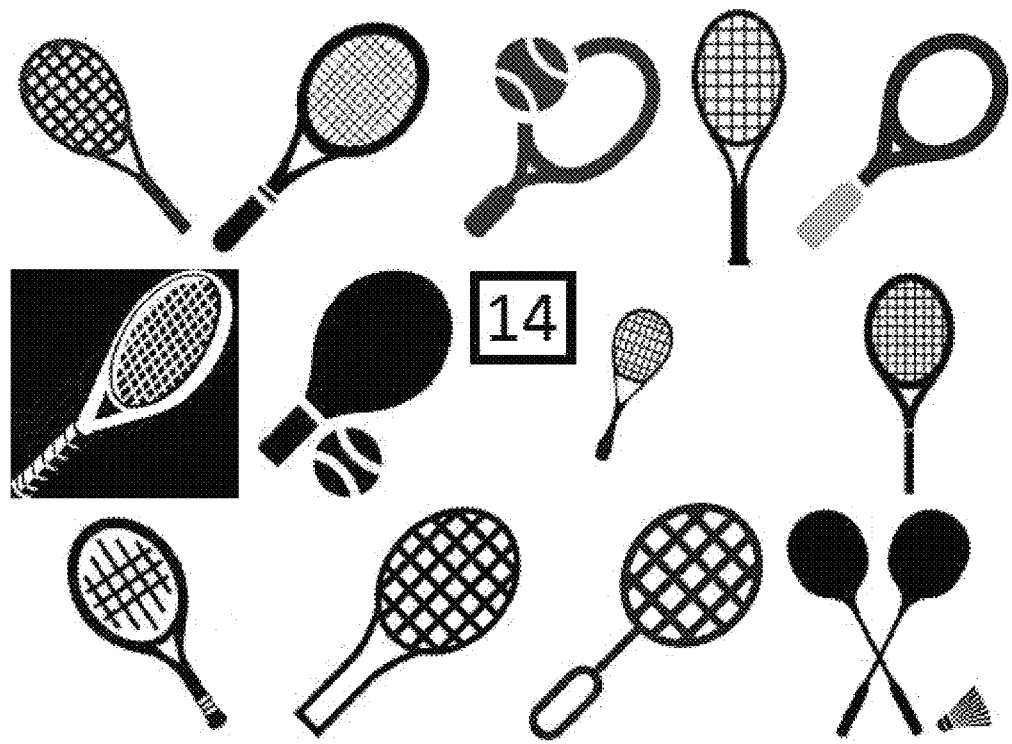
Figure 11B:
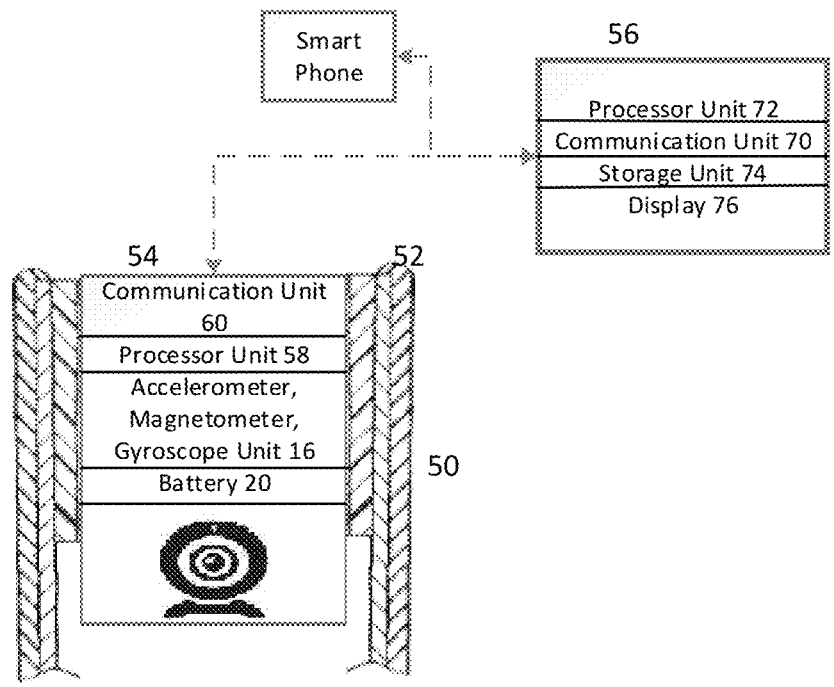
FIG. 11B shows electronics in the handle for golf clubs, rackets, or kung fu sticks.

FIGS. 11A-11B show an exemplary smart handle for sports such as tennis, badminton, table tennis, and golf, among others. The wireless sensor electronics 14 is mounted on a handle in the example of FIG. 11B. The handle can be embedded or can be removed upon completion of the sports event. The sports event does not have to be real, for example, in Virtual Reality (VR) sports applications, sensors including gyroscopes and cameras can be positioned on various body portions to capture motion as well as eye tracking, mouth tracking, speech recognition, among others.

The handle includes a swing analyzer measurement portion 54 in the grip end 52 of the handle of a golf club or a tennis/badminton racket, and a remote or handheld unit 56. The swing analyzer measurement portion 54 includes an accelerometer 16 of combination accelerometer and gyroscope or magnetometer unit, a processor unit 58 coupled to the accelerometer 16, and a battery 20 that is electrically coupled to and provides power to the accelerometer 16 and processor unit 58. A camera is included to capture videos of the swing and also the game in progress for future reference. A communications unit 60 is also housed in the grip end 52 of the golf club 50, receives power from the battery 20, and is coupled to the processor unit 58. Swing analyzer measurement portion 54, with or without the communications unit 60, may be assembled as an integral unit and inserted into a hollow portion of the handle of the golf club or tennis/racket handle 50 at the grip end 52 thereof. Processor unit 58 may be an integrated device that includes hardware and software components capable of processing acceleration measured by the accelerometer(s) 16 and converting the measured acceleration into data about the force on the shaft and position of the face of the club at impact at a set distance. If the measured force exceeds a threshold the measured force or a signal derived therefrom is transmitted via the communications unit 60 to the handheld unit 56. If not, acceleration and face position at impact of the golf club or tennis racket handle 50 is obtained again. The threshold is set so that only acceleration or force measurements arising from actual swings of the golf club 50 are transmitted to the handheld unit 56. Handheld or remote unit 56 includes an application or computer program embodied on a non-transitory computer-readable medium that performs the golf ball carrying distance estimation or prediction steps, as well as manages the training stage described above. Importantly, the handheld unit 56 receives acceleration measurement data from the golf clubs/tennis rackets equipped with a swing analyzer measurement portion 54 and the club face angle in relation to the swing plane, and manages the carrying distance estimation steps for all golf clubs equipped with the swing analyzer measurement portion 54 that are designed to communicate therewith. Handheld or remote unit 56 may be a standalone unit for use only with the golf clubs equipped with the swing analyzer measurement portion 54, and incorporating the application thereon, or may be a smartphone or similar device with the application embodied thereon or downloaded thereto and that can be used for other purposes. Handheld or remote unit 56 includes a communications unit 70 that communicates with the communications unit 60 on each golf club or tennis racket handle 50, i.e., with the communications units present on all of the golf clubs 50 equipped with swing analyzer measurement portions 54 and which have been designated to communicate therewith. Communications unit 70 may be an integral part of the handheld unit 56 as is the case when the handheld unit 56 is a smartphone. Communications unit 70 may also communicate with another device such as a Smartphone, to perform more data manipulations relating to the golf swing and/or swing results to provide more information to the user. The data and the calculation/manipulation results can be stored in the Smartphone and displayed when desired. Currently usable Smartphones are Apple iOS iPhones and Android operating system phones. Handheld or remote unit 56 also includes a processor unit 72, a storage unit 74 and a display 76. When the handheld unit 56 is a smartphone or similar device, all of the processor unit 72, storage unit 74 and display 76 may be integral components thereof. Processor unit 72 performs functions similar to those performed by the processor unit 18 described above, e.g., calculates an estimated carrying distance for the golf ball based on the acceleration measured by the accelerometer(s) 16 and transmitted via the communications units 60, 70, and the type of club provided to the application or computer program in the processor unit 72. Storage unit 74 receives and stores information about the carrying distance of each club as a function of clock or swing position, e.g., in the form of a virtual table associating the type of club, the swing or swing position and the estimated carrying distance.

Other sensors can be used as well. For example, the handle can contain conductive ink to capture biometric. One embodiment uses Samsung's Bio-Processor which is an all-in-one health solution chip to measure bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. The handle can also contain other sensors including gyroscopes, temperature and pressure sensors, moisture sensors, clocks, chemical and/or biological sensors, etc. Features of the smart handle can include:

Smart Protective Gear

Figure 12A:
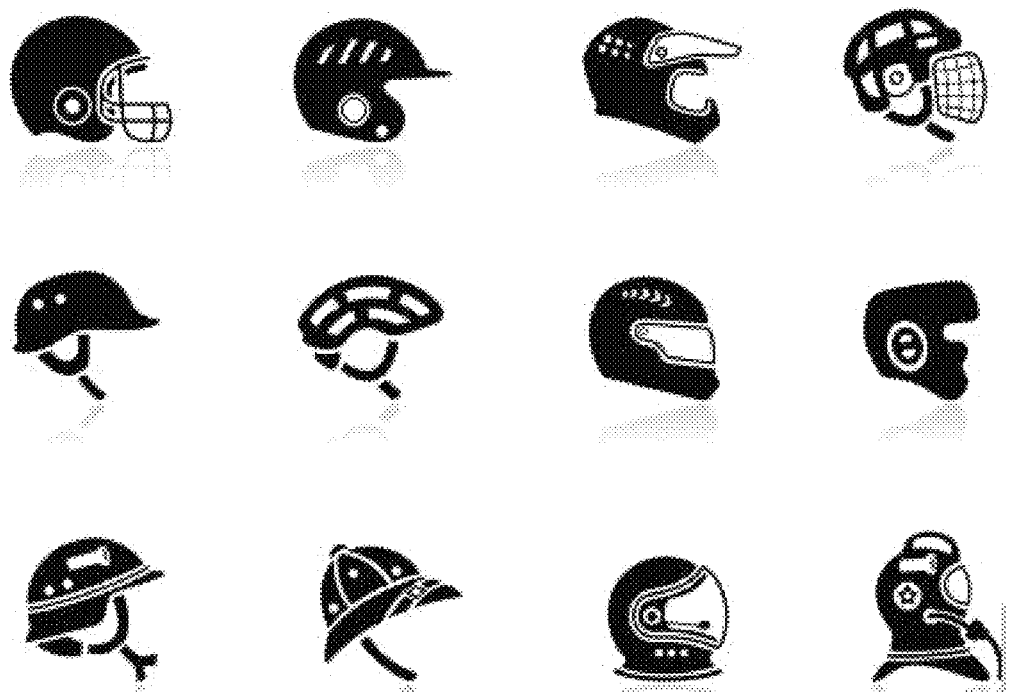
Figure 12C:
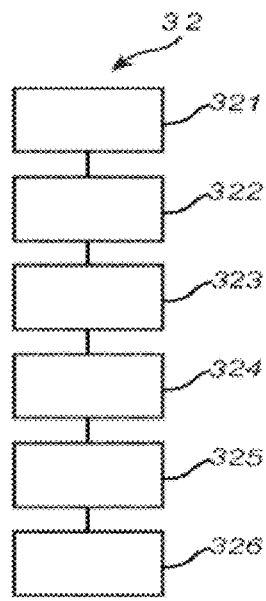
FIG. 12C shows an exemplary process to fabricate mass-customized protective gear.
Figure 12B:
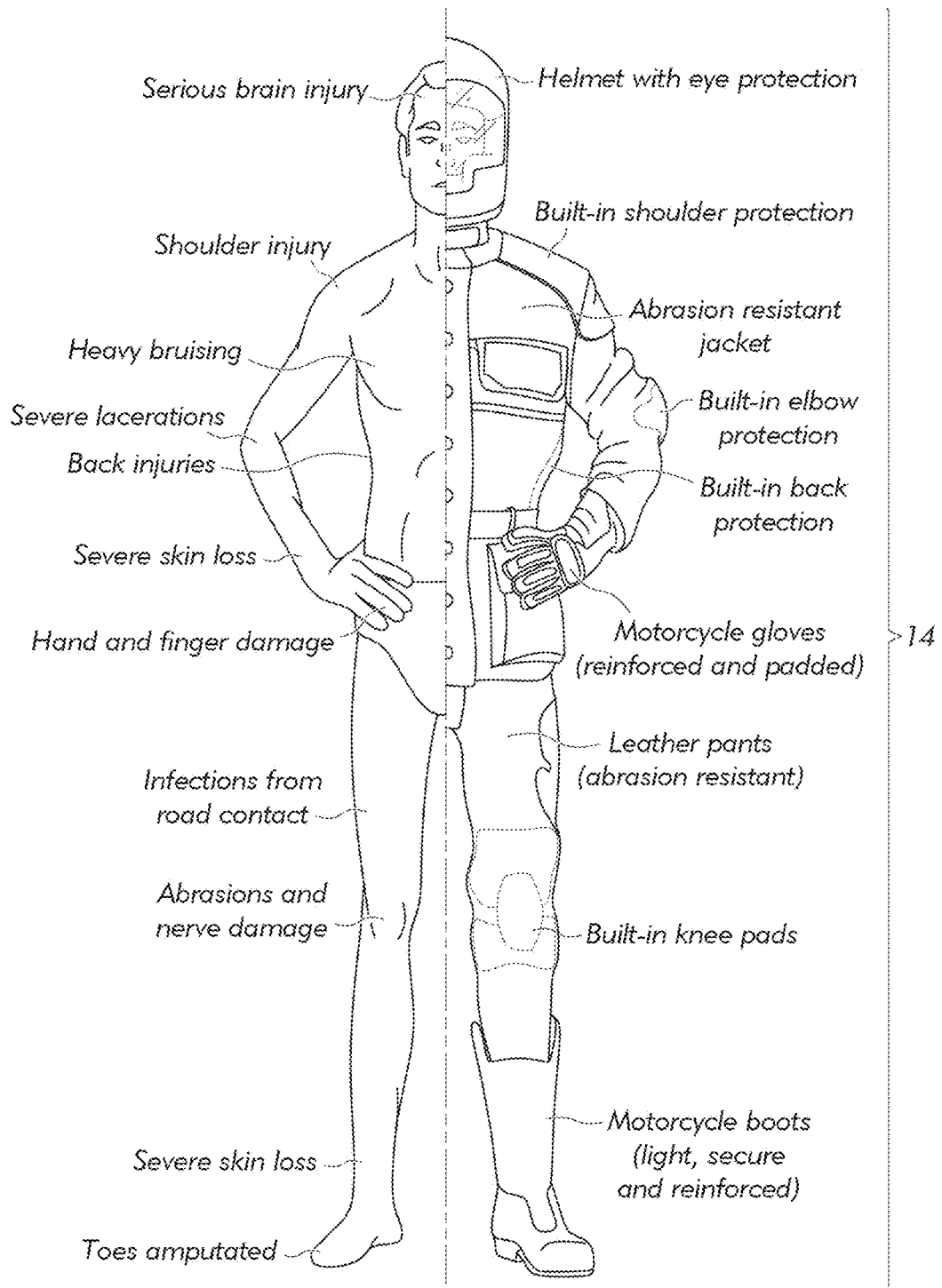

FIGS. 12A-12C illustrate smart protective gears embedded with the IoT sensors and instrumentations to report potential health issues. For soccer, the protection includes shin guards. For football, the protection includes Helmets, Chin Straps & Chin Shields, Cups & Athletic Supporters, Elbow Sleeves & Arm Pads, Back Plates & Rib Protection, Facemasks, Girdles, Helmet Visors, Shoulder Pads, Hip & Tail Pads, Mouthguards, Neck Rolls. For motorcycling, the protection includes helmet, should pads, jacket with back protection, padded gloves, leather pants, knee pads, and boots. For rock climbing, the protection includes shoes, carabiners, webbing, harnesses, among others.

The wireless sensor electronics 14 is mounted on the helmet or shoulder pad in the example of FIG. 12A or 12C. The electronics 14 can be embedded or can be removed upon completion of the sports event. The sports event does not have to be real, for example, in Virtual Reality (VR) sports applications, sensors including gyroscopes and cameras can be positioned on various body portions to capture motion as well as eye tracking, mouth tracking, speech recognition, among others.

The protection gear includes an impact sensor such as an accelerometer to indicate if concussion has occurred. Other sensors can be used as well. For example, the handle can contain conductive ink to capture biometric. One embodiment uses Samsung's Bio-Processor which is an all-in-one health solution chip to measure bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. The handle can also contain other sensors including gyroscopes, temperature and pressure sensors, moisture sensors, clocks, chemical and/or biological sensors, etc.

Impact sensors, or accelerometers, measure in real time the force and even the number of impacts that players sustain. Data collected is sent wirelessly via Bluetooth to a dedicated monitor on the sidelines, while the impact prompts a visual light or audio alert to signal players, coaches, officials, and the training or medical staff of the team. One such sensor example is the ADXL377 from Analog Devices, a small, thin and low-power 3-axis accelerometer that measures acceleration from motion, shock, or vibration. It features a full-scale range of ±200 g, which would encompass the full range of impact acceleration in sports, which typically does not exceed 150 g's. Specifically designed for concussion and head-trauma detection, at 3 mm×3 mm×1.45 mm, the device is small enough to be designed into a helmet. Sensitivity, listed at 6.5 mV/g with −3 dB bandwidth at 1.6 kHz, is sufficiently high for the application. When a post-impact player is removed from a game and not allowed to return until cleared by a concussion-savvy healthcare professional, most will recover quickly. If the injury is undetected, however, and an athlete continues playing, concussion recovery often takes much longer. In addition, the industry is finding that long-term problems from delayed or unidentified injury can include: Early dementia, Depression, Rapid brain aging, and Death. The cumulative effects of repetitive head impacts (RHI) increases the risk of long-term neuro-degenerative diseases, such as Parkinson's disease, Alzheimer's, Mild Cognitive Impairment, and ALS or Lou Gehrig's disease. The sensors' most important role is to alert to dangerous concussions. Yet, the act of real-time monitoring brings these players to the attention of their coaches not only to monitor serious impacts but, based on the data provided by the sensors, also help to modify a player's technique so that they are not, for example, keeping their head low where they can sustain injury to the front and top of the skull. In the NFL there also has been an aggressive crackdown against hits to the head and neck—a response to the ongoing concussion crisis—resulting in immediate penalty to players using their helmets as a "weapon". Customized mouthguards also have sensors therein. A customized mouthguard has tested to be 99 percent accurate in predicting serious brain injury after near-concussive force, according to an Academy of General Dentistry study2. Teeth absorb and scatter infrared light, which shows how much force is taking place at the moment of impact.

Custom Gear

In one aspect, the protective gear is custom formed to the athlete's body. This is done in FIG. 12C as follows:
321) perform 3D scan of person and create 3D model
322) form positive mold from the 3D model
323) place mold into 2 phase 3D printer to form a negative
324) put composite material into mold and form composite protection gear
325) embed IoT electronics into one or more locations into the composite protection gear
326) link IoT electronics with mobile devices and cloud based storage and process impact data and warn user if impact is unsafe.

The protection gear or footwear can be custom produced at the request of a customer, who can specify the nature of the customization for one or more pairs of helmet, protective gear, or footwear. Each helmet of the footwear may have a different design, message or message portion designed into it and rendered using the bed of pins described below to make the custom helmet or shoe design messages or shapes, and then the bottom sole can be fabricated using the reformable bed described below. Once the negative is fixed in the reformable bed, suitable materials for the bottom sole can be deposited and cured and can include rubber, plastic, or foam. Further customization can be done by a Computerized Numerical Control (CNC) where component design can be integrated with computer-aided design (CAD) and computer-aided manufacturing (CAM) programs. The device can be programmed to use a number of different tools-drills, saws, and so on. Alternatively a number of different machines can be used with an external controller and human or robotic operators that move the component from machine to machine. Regardless, a series of steps needed to produce a part can produce a part that closely matches the original CAD design in a highly automated fashion. In accordance with aspects of the subject matter disclosed herein through the use of reformable bed and a suitably programmed CNC tools, customized footwear with custom cut sole designs, can cost effectively be created in small quantities and yet scalable for mass-customization.

Shock Protection

In one embodiment, the sole is not completely filled with material, but is formed as a lattice structure. The system generates triangulated surfaces for export to additive manufacturing (AM) processes. Implementing a process that coverts a CAD object into an image, known as voxelisation, the company uses an image-based method which allows designers to generate implicitly defined periodic lattice structures suitable for additive manufacturing applications and finite element analysis (FEA). The system generates robust lattice structures can overcome the problems faced with hollowing out a part to reduce weight and optimize designs prior to 3D printing. Cellular lattice structures can be used to replace the volume of CAD and image-based parts, reducing weight whilst maintaining optimal performance. In this way, the shoes can be light weight yet strong and provide shock impact absorption during running for the wearer.

Topology optimization can be used to drive the material layout including the lattice regions. From this new topology optimization implementation, the system can identify void regions in the design space, where the material can be removed, regions where solid material is needed, and regions where lattice structure is required. This allows the system to generate the optimal hybrid or blended solid-lattice design based on desired functionality of the part.

Lattice structures can be considered as porous structures. In the case of topology optimization, the semi-dense elements are like the porous media. To refine the design, a second-phase involves a detailed sizing optimization where the end diameters of each lattice cell member are optimized. This allows for further weight reduction while meeting design requirements, such as buckling, stress, and displacement.

A piezo material can be actuated to generate a vibration that cancels incoming shock on the wearer. In one embodiment, the system tracks the shock such as the foot contact patterns and generates an anti-vibration signal to cancel the shock generated when the foot contacts the ground. In this embodiment, a processor receives foot ground contact using an accelerometer. The stride pattern is determined, and the next foot ground contact is detected, and the piezo material is actuated with a counter signal to cancel the expected shock. This is similar to the noise cancellation, except the vibration/shock is canceled.

In one hybrid embodiment, the shoes incorporate passive and active isolation elements. The passive component consists of springs which support the load weight and provide isolation over a broad spectrum. These springs provide a basic level of isolation in the lower frequencies and excellent isolation in the higher frequencies (above 200 Hz). They also support the load while allowing for travel of the actuators in the active component. The performance of the springs is augmented and corrected by an active isolation component. The active isolation component consists of vibration sensors, control electronics, and actuators. The vibration sensors are piezo accelerometers. A plurality of sensors in each isolation system are positioned in different orientations to sense in all six degrees of freedom. The piezo accelerometers convert kinetic vibration energy into electrical signals which are transmitted to the control electronics. The electronics reconcile and process the signals from the various sensors using a processor. The electronics then send a cancellation signal to the actuators. The actuators generate vibrations that are equal to the incoming vibrations but out of phase in relation to the incoming vibrations. This results in cancellation of the incoming vibrational noise, leaving the wearer undisturbed. This process occurs within 5-20 milliseconds of a vibration entering the system.

Figure 13:
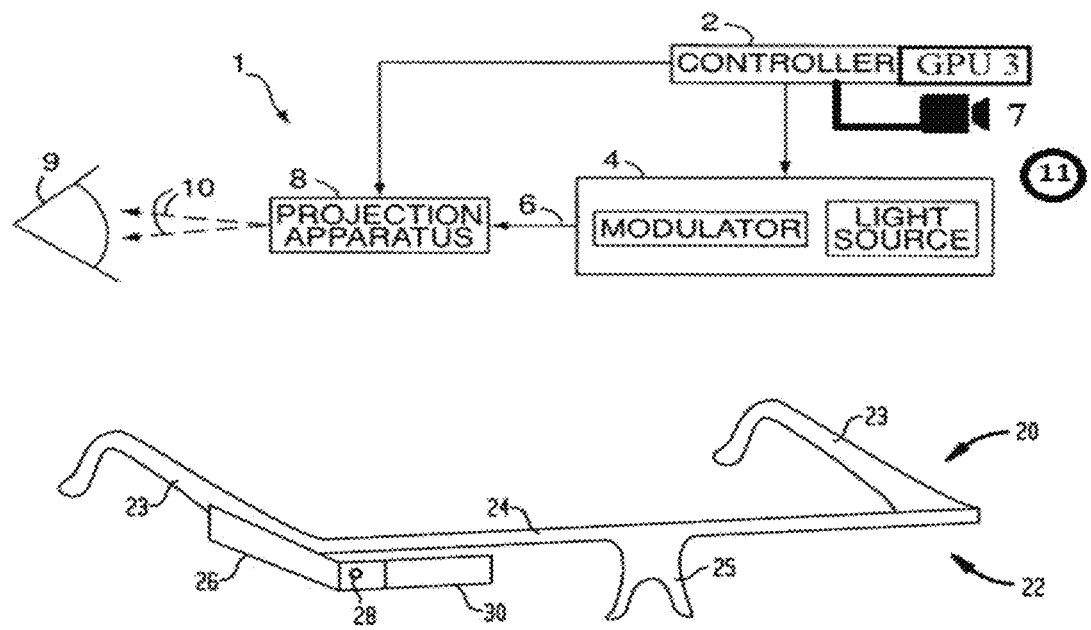
FIG. 13 shows exemplary augmented/virtual reality systems.

FIG. 13 illustrates a system 1 for projecting an image onto a human retina and for scanning the eye. Using waveguides, 3D objects can be viewed from the projections. Data from the scan can be used for medical application such as glucose sensing or for emotion sensing when blood vessels dilate. The system 1 can be used in virtual reality applications, augmented reality applications, or a combination thereof. The system 1 includes a controller 2 with graphical processing units (GPUs) 3 which generates signals in accordance with processes detailed hereinafter for presentation to a modulated optical source 4, which provides a modulated optical beam 6 to a projection apparatus 8. A graphics processing unit (GPU), occasionally called visual processing unit (VPU), is a specialized electronic circuit designed to rapidly manipulate and alter memory to accelerate the creation of images in a frame buffer intended for output to a display device. GPUs are used in embedded systems, mobile phones, personal computers, workstations, and game consoles. GPUs are very efficient at manipulating computer graphics and image processing, and their highly parallel structure makes them more efficient than general-purpose CPUs for algorithms where the processing of large blocks of data is done in parallel. For example, Nividia's PASCAL system has over 5 TeraFLOPS of double precision performance. One or more cameras 7 can capture video images that can be projected by the projection apparatus 8 to stimulate the neurons on the eye of a blind person to enable the blind person to see at least a part of the video. The one or more cameras 7 can aim at the retina or can aim in the viewing direction of a user, depending on the application. The projection apparatus scans an image onto the retina of the eye 9 of a viewer, as indicated by reference numeral 10. The modulated light source includes a laser or other light source, which can be used for generation of an optical image. Preferably, the light source is a laser. The modulated light source can also include a discrete optical modulator, which is addressable and receives control signals from the controller 2. The optical modulator 4 can be of a known type, and is capable of modulating an optical beam with sufficient bandwidth to allow for presentation of the image to the viewer. Those skilled in the art will note that in certain embodiments, the light source may be modulated directly, without the inclusion of the discrete optical modulator. The on-chip laser light source emits a laser light beam that travels through the lens and a partially-silvered mirror. The laser light beam is reflected off a MEMS scanning mirror that is oscillating to provide a scan. The MEMS scanning mirror can be a resonate transducer, as known in the art. This device can be made to resonate at a desired frequency, either in one direction or in two directions. The resonate transducer may use a mechanically free beam of polysilicon and may also be positioned on thin membranes or diaphragms, cantilevers, and other flexure type mechanisms. The resonant frequency may be induced electronically by the scanner electronics, as known in the art. The MEMS scanning mirror has a mirrored surface and resonates at a controlled frequency in the horizontal and vertical direction, can produce a rastering scan pattern when a laser light source is reflected from its surface. The MEMS scanning mirror may be fabricated using integrated circuit techniques such as surface micromachining Alternative fabrication techniques also exist such as bulk micromachining, LIGA (a German acronym referring to lithography, electroforming, and injection molding), or LIGA-like machining, as known in the art. Additional fabrication techniques such as chemical-mechanical polishing may be performed to improve the optical quality of the mirrored surface by reducing the surface roughness. In one embodiment, the light source of unit 4 can be an LED shining light on an object 11 for spectral analysis. The light source can be programmed to sequentially shine predetermined wavelengths on the object 11, and the camera 7 captures the resulting light. The light source displays light at the next predetermined wavelength and the camera 7 captures the result. This is repeated until a multi-spectral analysis can be done for only visible, only non-visible, or both visible and non-visible light wavelengths.

The light emitting spots are produced by microns-sized diodes/lasers pumping phosphors located above the diodes/lasers. The individual spots of light used to make an image can all be of the same color (monochromatic) or of different colors. In the multiple color operation, the present invention uses a single or monochromatic pump source rather than discrete diode/laser sources of different colors. The lasers are fabricated in a two dimensional ("2D") array format with established semiconductor processing techniques and practices. The 2D laser arrays are then integrated with nonlinear optical processes such as up-conversion (anti-Stokes process) in order to obtain multiple color outputs. Using photons with nonlinear up-conversion materials to obtain visible light output from a display device provides an advantage toward miniaturization of the present display.

The optical system is not limited to use of visible light, but may also employ light in other portions of the electromagnetic spectrum (e.g., infrared, ultraviolet) and/or may employ electromagnetic radiation that is outside the band of "light" (i.e., visible, UV, or IR), for example employing electromagnetic radiation or energy in the microwave or X-ray portions of the electromagnetic spectrum.

In some implementations, a scanning light display is used to couple light into a plurality of primary planar waveguides. The scanning light display can comprise a single light source that forms a single beam that is scanned over time to form an image. This scanned beam of light may be intensity-modulated to form pixels of different brightness levels. Alternatively, multiple light sources may be used to generate multiple beams of light, which are scanned either with a shared scanning element or with separate scanning elements to form imagery. These light sources may comprise different wavelengths, visible and/or non-visible, they may comprise different geometric points of origin (X, Y, or Z), they may enter the scanner(s) at different angles of incidence, and may create light that corresponds to different portions of one or more images (flat or volumetric, moving or static). The light may, for example, be scanned to form an image with a vibrating optical fiber.

In one embodiment, the optical coupler subsystem collimates the light emerging from the scanning fiber cantilever The collimated light is reflected by mirrored surface into a narrow distribution planar waveguide which contains at least one diffractive optical element (DOE). The collimated light propagates vertically along the distribution planar waveguide by total internal reflection, and in doing so repeatedly intersects with the DOE with a low diffraction efficiency. This causes a fraction (e.g., 10%) of the light to be diffracted toward an edge of the larger primary planar waveguide 51 at each point of intersection with the DOE and a fraction of the light to continue on its original trajectory down the length of the distribution planar waveguide via TIR. At each point of intersection with the DOE, additional light is diffracted toward the entrance of the primary waveguide. By dividing the incoming light into multiple outcoupled sets, the exit pupil of the light is expanded vertically by the DOE in the distribution planar waveguide. This vertically expanded light coupled out of distribution planar waveguide enters the edge of the primary planar waveguide. Light entering primary waveguide propagates horizontally along the primary waveguide 51 via TIR. As the light intersects with DOE at multiple points as it propagates horizontally along at least a portion of the length of the primary waveguide via TIR. The DOE may advantageously be designed or configured to have a phase profile that is a summation of a linear diffraction grating and a radially symmetric diffractive lens. The DOE may advantageously have a low diffraction efficiency. At each point of intersection between the propagating light and the DOE, a fraction of the light is diffracted toward the adjacent face of the primary waveguide 51 allowing the light to escape the TIR, and emerge from the face of the primary waveguide 51. The radially symmetric lens aspect of the DOE additionally imparts a focus level to the diffracted light, both shaping the light wavefront (e.g., imparting a curvature) of the individual beam as well as steering the beam at an angle that matches the designed focus level. A plurality of beams can extend geometrically to a focus point, and each beam is advantageously imparted with a convex wavefront profile with a center of radius at focus point to produce an image or virtual object at a given focal plane. The generation thereby of a multi-focal volumetric display, image or light field can be done, and the system can include one or more sources of red, green, and blue laser light optically coupled into a proximal end of a single mode optical fiber.

A computer database of graphical imagery is addressed by graphics processing units (GPUs) 3 in the controller 2, such that each point (or pixel) along a sinusoidal path laser light represents an x-y pixel coordinate in the database so as to reconstruct a coherent image to a viewer and modulated to fit physiology of the eye. For example, since at a small distance from the fovea (FIG. 1C) the human eye has very poor ability to resolve sharpness or color, the system can supple the human visual cortex and brain's processing to integrate the entire visual field into a cohesive image. For example, the middle of the retina, where the minimum photon flux is presented due to the maximum velocity of the raster scan, is dimmer that the ends of the retina, which receive a maximum flux of photons. The prior art systems consequently must, at a minimum, compensate for the foregoing natural occurring phenomena to even the brightness of each of the pixels. Further, with a high concentration of image-sensing cones at the eye's fovea, the controller handles rapidly declining cone concentration as a function of distance from the fovea to the periphery of the retina. The controller drives the retinal illumination as center-weighted, which can be the inverse of the illumination. In one embodiment, illumination of just the central portion can be sufficient to create the desired image.

In the light source, a mirror oscillates sinusoidally, such as in an ellipsoidal pattern, which causes the formation of high-resolution imagery in a concentrated zone, while substantially lowering resolution in a circular field around that zone. By coupling the location of this zone of high resolution to the eye's foveal area via an eye tracking mechanism, as discussed below, a very high apparent resolution image is provided. System bandwidth requirements are reduced. Rather than a standard pixel grid in the horizontal and vertical axes, the computer can be tasked to generate pixels in an ellipsoidal sweep with a rotating central axis. This concentrates a large number of pixels into a central zone. The laser beam can be swept in sinusoidal patterns in such a manner that each sweep of the laser beam crosses at a single point in the x-y field, while the sweep precesses, so that a "frame" of image is represented by a circular field. The crossing point can be moved to any position within the field, via proper modulation of a mirror. As the laser beam is swept through a spiral pattern, it can be modulated in brightness and focus so that as the beam sweeps through the single point it is highly focused, yet much less bright. As the beam sweeps away from the point, it can grow grows brighter and less focused, so that the resultant circular field is of even apparent brightness. In this manner the beam crossing point 802 can be of extremely high resolution (since virtually every sweep passes through it) and of extremely high temporal information (since each sweep represents a small fraction of a "frame" representing one complete spiral sweep filling the entire circular field. For example, one complete spiral sweep of the circular field could occur in one-sixtieth ({fraction (1/60)}th) of a second, and consist of 525 precessing sinusoidal sweeps; thus, the field could contain the same information as a field of NTSC video. In contrast to this focus point of all sweeps, the periphery of the field drops off in clarity and information responsive, such as in direct proportion, to the distance from the focus point. At the periphery of the field, resolution is low. Thus, the visual information of a frame (or field) of an image is more concentrated at the crossing point, and more diffuse at the periphery.

One embodiment uses a plurality of cameras 7 to provide a gesture control feature. A pair of light sources can be disposed to either side of cameras and controlled by an image-analysis system. In some embodiments where the object of interest is a person's hand or body, use of infrared light can allow the motion-capture system to operate under a broad range of lighting conditions and can avoid various inconveniences or distractions that may be associated with directing visible light into the region where the person is moving. However, a particular wavelength or region of the electromagnetic spectrum is required.

It should be stressed that the foregoing arrangement is representative and not limiting. For example, lasers or other light sources can be used instead of LEDs. For laser setups, additional optics (e.g., a lens or diffuser) may be employed to widen the laser beam (and make its field of view similar to that of the cameras). Useful arrangements can also include short- and wide-angle illuminators for different ranges. Light sources are typically diffuse rather than specular point sources; for example, packaged LEDs with light-spreading encapsulation are suitable.

In operation, cameras 7 are oriented toward a region of interest in which an object of interest (in this example, a hand) and one or more background objects can be present.

Light sources illuminate the region. In some embodiments, one or more of the light sources and cameras are disposed below the motion to be detected, e.g., where hand motion is to be detected, beneath the spatial region where that motion takes place. This is an optimal location because the amount of information recorded about the hand is proportional to the number of pixels it occupies in the camera images, the hand will occupy more pixels when the camera's angle with respect to the hand's "pointing direction" is as close to perpendicular as possible. Because it is uncomfortable for a user to orient his palm toward a screen, the optimal positions are either from the bottom looking up, from the top looking down (which requires a bridge) or from the screen bezel looking diagonally up or diagonally down. In scenarios looking up there is less likelihood of confusion with background objects (clutter on the user's desk, for example) and if it is directly looking up then there is little likelihood of confusion with other people out of the field of view (and also privacy is enhanced by not imaging faces). In this arrangement, image-analysis system can quickly and accurately distinguish object pixels from background pixels by applying a brightness threshold to each pixel. For example, pixel brightness in a CMOS sensor or similar device can be measured on a scale from 0.0 (dark) to 1.0 (fully saturated), with some number of gradations in between depending on the sensor design. The brightness encoded by the camera pixels scales standardly (linearly) with the luminance of the object, typically due to the deposited charge or diode voltages. In some embodiments, light sources 808, 810 are bright enough that reflected light from an object at distance rO produces a brightness level of 1.0 while an object at distance rB=2rO produces a brightness level of 0.25. Object pixels can thus be readily distinguished from background pixels based on brightness. Further, edges of the object can also be readily detected based on differences in brightness between adjacent pixels, allowing the position of the object within each image to be determined. Correlating object positions between images from cameras 7 allows image-analysis system to determine the location in 3D space of object 814, and analyzing sequences of images allows image-analysis system to reconstruct 3D motion of object using conventional motion algorithms.

In identifying the location of an object in an image according to an embodiment of the present invention, light sources are turned on. One or more images are captured using cameras. In some embodiments, one image from each camera is captured. In other embodiments, a sequence of images is captured from each camera. The images from the two cameras can be closely correlated in time (e.g., simultaneous to within a few milliseconds) so that correlated images from the two cameras can be used to determine the 3D location of the object. A threshold pixel brightness is applied to distinguish object pixels from background pixels. This can also include identifying locations of edges of the object based on transition points between background and object pixels. In some embodiments, each pixel is first classified as either object or background based on whether it exceeds the threshold brightness cutoff. Once the pixels are classified, edges can be detected by finding locations where background pixels are adjacent to object pixels. In some embodiments, to avoid noise artifacts, the regions of background and object pixels on either side of the edge may be required to have a certain minimum size (e.g., 2, 4 or 8 pixels).

Alternatively, glasses can be used to render AR, for example system 20 for receiving, transmitting, and displaying data. The system 20 is shown in the form of a wearable computing device eyeglass 22. The wearable computing device 22 may include side-arms 23, a center frame support 24, and a bridge portion with nosepiece 25. In the example shown in FIG. 13, the center frame support 24 connects the side-arms 23. The wearable computing device 22 does not include lens-frames containing lens elements. The wearable computing device 22 may additionally include an onboard computing system 26 and a video camera 28. The wearable computing device 22 may include a single lens element 30 that may be coupled to one of the side-arms 23 or the center frame support 24. The lens element 30 may include a display such as the laser projector described above, and may be configured to overlay computer-generated graphics upon the user's view of the physical world. In one example, the single lens element 30 may be coupled to the inner side (i.e., the side exposed to a portion of a user's head when worn by the user) of the extending side-arm 23. The single lens element 30 may be positioned in front of or proximate to a user's eye when the wearable computing device 22 is worn by a user. For example, the single lens element 30 may be positioned below the center frame support 24.

Video Feature Tracking and Matching

The GPU 3 can help with recognizing objects, as well as rasterizing the laser paintings to the eye. In one embodiment, the CPU and GPUs are in one device with a heterogeneous multicore microprocessor architecture, combining a general purpose processing core(s) and basic graphics core(s) into one processor package, with different clocks for the graphics core and the central processing core. The GPUs provide thousands of processors for parallel processing, similar to the way the brain operates in parallel.

In one embodiment, a KLT tracking process and a SIFT feature extraction process to enable real-time processing of high resolution video. The KLT tracking process computes displacement of features or interest points between consecutive video frames when image motion is fairly small. Feature selection is done by finding maximas of a saliency measure (minimum eigen-values of the 2×2 structure matrix obtained from gradient vectors. It is evaluated over the complete image and a subsequent non-maximal suppression is performed. Assuming a local translational model between subsequent video frames, the feature displacements are computed using Newton's method to minimize the sum of squared distances (SSD) within a tracking window around the feature position in the two images.

A multi-resolution KLT tracker allows handling larger image motion while multiple tracking iterations at each scale increases its accuracy. Features tracks are often lost after a few frames of tracking; hence new features are selected in a particular video frame only after tracking features in a few successive frames. This maintains a roughly fixed number of features in the tracker.

GPU-KLT maps these various steps to sets of different fragment programs. The multi-resolution pyramid of the image and its gradients are computed by a series of two-pass separable convolutions performed in fragment programs. The KLT cornerness map is computed in two render passes. The first pass computes the minimum eigen value of the 2×2 gradient matrix at each pixel and the two passes together accumulate the cornerness value within a 7×7 window centered at each pixel. During feature re-selection, the neighborhood of existing features is invalidated; early Z-culling avoids computations in these image regions. The cornerness map is transferred back to the CPU where non-maximal suppression is done to build the final feature-list. KLT tracking performs a fixed number of tracking iterations at each image resolution starting with the coarsest pyramid level. Each tracking iteration constructs a linear system of equations in two unknowns for each interest point, AX=B and directly solves them to update the estimated displacement. All steps are performed on the GPU. A SSD residual is computed between the two image patches of a particular KLT feature in order to reject features tracked inaccurately. Conditional statements are avoided in fragment programs by tracking a constant number of features and rejecting inaccurate tracks after the final tracking iteration on the GPU and before reading back the feature-list.

The Scale Invariant Feature Transform (SIFT) process performs extraction of interest points invariant to translation, rotation, scaling and illumination changes in images. It first constructs a Gaussian scale-space pyramid from the input image while also calculating the gradients and difference-of-gaussian (DOG) images at these scales. Interest points are detected at the local extremas within the DOG scale space. Once multiple keypoints have been detected at different scales, the image gradients in the local region around each feature point are encoded using orientation histograms and represented in the form of a rotationally invariant feature descriptor. The construction of the Gaussian scale space pyramid is accelerated on the GPU using fragment programs for separable convolution. The intensity image, gradients and the DOG values are stored in a RGBA texture and computed in the same pass. Blending operations in graphics hardware are used to find local extremas in the DOG pyramid in parallel at all pixel locations. The Depth test and the Alpha test is used to threshold these keypoints; The local principal curvatures of the image intensity around the keypoint is inspected; this involves computing the ratio of eigenvalues of the 2£2 Hessian matrix of the image intensity at that point. The keypoint locations are implicitly computed in image-sized, binary buffers, one for each scale in the pyramid. A fragment program compresses (a factor of 32) the binary bitmap into RGBA data, which is readback to the CPU and decoded there. At this stage, a list of keypoints and their scales have been retrieved. Since reading back the gradient pyramid (stored in texture memory) to the CPU is expensive, the subsequent steps in SIFT are also performed on the GPU. Gradient vectors near the keypoint location are Gaussian weighted and accumulated inside an orientation histogram by another fragment program. The orientation histogram is read back to the CPU, where its peaks are detected. Computing histograms on the GPU is expensive and doing it on the CPU along with a small readback is a little faster. The final step involves computing 128 element SIFT descriptors. These consist of a set of orientation histograms built from 16£16 image patches in invariant local coordinates determined by the associated keypoint scale, location and orientation. SIFT descriptors cannot be efficiently computed completely on the GPU, as histogram bins must be blended to remove quantization noise. This step is partitioned between the CPU and the GPU. Each feature's gradient vector patch is resampled, weighted using a Gaussian mask using blending support on the GPU. The resampled and weighted gradient vectors are collected into a tiled texture block which is subsequently transferred back to the CPU and then used to compute the descriptors. This CPU-GPU partition was done to minimize data readback from the GPU since transferring the whole gradient pyramid back to the CPU is impractical. Moreover texture re-sampling and blending are efficient operations on the GPU and are performed there. This also produces a compact tiled texture block which can be transferred to the CPU in a single readback. GPU-SIFT gains a large speed-up in the Gaussian scale-space pyramid construction and keypoint localization steps. The compressed readback of binary images containing feature positions reduces the readback data-size by a factor of 32. The feature orientation and descriptors computation is partitioned between the CPU and GPU in a way that minimizes data transfer from GPU to CPU.

Video Compression

In one embodiment, the video feature tracking and matching described above is used to compress video. The operation is as follows:

1) send the first few minutes of video using conventional or compressed video and simultaneously determine predetermine facial and body features;

2) after the start up period, for each frame determine whether the current frame only has facial/body changes and if so look for an updated position of the features and transmit a vector indicating facial and body feature changes to the remote computer the remote computer converts the vector of changed facial features to an image of the user's face and body position 3) otherwise, there are significant changes to the frame and so loop back to (1) to do a fresh compression cycle.

The process achieves a very high compression ratio since only a vector of feature position changes are sent as a vector and the vector is converted back into frame image by the remote computer. Moreover, if significant scene changes occur (such as new participants entering the conference, or participant picks up a book and show book to the camera), then the system reverts back to H.264 compression of full image.

Face Recognition

Face detection can be performed on board the camera for autofocus of the camera. Additionally, the face detection can be used to identify regions in the video that should be encoded at high resolution for certain applications.

A parallelized implementation of convolutional neural networks (CNNs) is done with parallelizing the detection process using the GPU. The convolutional network consists of a set of layers each of which contains one or more planes. Approximately centered and normalized images enter at the input layer. Each unit in a plane receives input from a small neighborhood in the planes of the previous layer. The idea of connecting units to local receptive fields dates back to the 1960s with the perceptron and Hubel and Wiesel's discovery of locally sensitive, orientation-selective neurons in the cat's visual system. The general strategy of a convolutional network is to extract simple features at a higher resolution, and then convert them into more complex features at a coarser resolution. The simplest was to generate coarser resolution is to sub-sample a layer by a factor of 2. This, in turn, is a clue to the convolutions kernel's size.

The weights forming the receptive field for a plane are forced to be equal at all points in the plane. Each plane can be considered as a feature map which has a fixed feature detector that is convolved with a local window which is scanned over the planes in the previous layer. Multiple planes are usually used in each layer so that multiple features can be detected. These layers are called convolutional layers.

The GPU supports a fast, automatic system for face recognition which is a combination of a local image sample representation, a self-organizing map network, and a convolutional network for face recognition. For the images in the training set, a fixed size window is stepped over the entire image and local image samples are extracted at each step. At each step the window is moved by 4 pixels. Next, a self-organizing map (e.g. with three dimensions and five nodes per dimension) is trained on the vectors from the previous stage. The SOM quantizes the 25-dimensional input vectors into 125 topologically ordered values. The three dimensions of the SOM can be thought of as three features. The SOM can be replaced with the Karhunen-Loeve transform. The KL transform projects the vectors in the 25-dimensional space into a 3-dimensional space. Next, the same window as in the first step is stepped over all of the images in the training and test sets. The local image samples are passed through the SOM at each step, thereby creating new training and test sets in the output space created by the self-organizing map. (Each input image is now represented by 3 maps, each of which corresponds to a dimension in the SOM. The size of these maps is equal to the size of the input image divided by the step size. A convolutional neural network, or alternatively a multilayer perceptron neural network, is trained on the newly created training set.

The self-organizing map provides a quantization of the image samples into a topological space where inputs that are nearby in the original space are also nearby in the output space, which results in invariance to minor changes in the image samples, and the convolutional neural network provides for partial invariance to translation, rotation, scale, and deformation. Substitution of the Karhunen-Lo'eve transform for the self organizing map produced similar but slightly worse results. The method is capable of rapid classification, requires only fast, approximate normalization and preprocessing, and consistently exhibits better classification performance than the eigenfaces approach on the database considered as the number of images per person in the training database is varied from 1 to 5.

Face Detection/Gesture Detection

As discussed above, a parallelized implementation of convolutional neural networks (CNNs) is done with parallelizing the detection process using the GPU. This can be used for autofocus of the camera. Once the face is detected, the GPUs can also be used to detect gestures as commands. Motion features are first computed on the input image sequence (stationary camera assumed). The face detector is then employed to obtain a user-centric representation, and again a classifier to discriminate between gestures is learned using a variant of AdaBoost. A real-time version of this classifier is deployed using the GPU.

To calculate the motion features, the optical flow for each frame is determined. The optical flow vector field F is then split into horizontal and vertical components of the flow, Fx and Fy, each of which is then half-wave rectified into four non-negative channels Fx+, Fx−, Fy+, Fy−. A channel corresponding to motion magnitude F0 is obtained by computing the L2 norm of the four basic channels. These five non-negative channels are then normalized to facilitate gesture recognition in soft-real time where frame rates can be variable, and to account for different speed of motion by different users.

Given a vector v that represents the optical flow for a given pixel, the system computes $v=v/(\|v\|+e)$, where e is used to squash optical flow vectors with very small magnitude introduced by noise. Next, each of the five channels is box-filtered to reduce sensitivity to small translations by the user performing the gesture. This final set of five channels: ^Fx+, ^Fx−, ^Fy+, ^Fy−, ^F0 will be used as the motion features for each frame.

A gesture is represented as a collection of movements required to complete a single phase of the gesture, rather than just capture a subset of the gesture phase. Hence, the system aggregates the motion features over a temporal history of the last k frames, for some k which is large enough to capture all frames from a gesture phase.

Face detection is used to create a normalized, user centric view of the user. The image is scaled based on the radius of the detected face, and is then cropped and centered based on the position of the face. The frame is cropped and resized to a 50×50 pixel region centered around the user. All five motion feature channels described above are flattened into a single vector which will be used to determine the gesture being performed.

A multi-class boosting process AdaBoost is used such as the one at http://multiboost.sourceforge.net AdaBoost takes the motion features as input. The supervised training is based on a set of labeled gestures. A set of weak learners is generated based on thresholding value from a particular component of the motion feature vector. The output of the final strong learner on motion feature v for class label is determined using weights chosen by AdaBoost.

Panaroma Stitching

The GPUs 3 of can perform panaroma stitching so that the user can see a 180 degree immersive view. The GPU operations are done pipeline fashion as follows: Radial Distortion Correction. Next, the GPUs perform Keypoint Detection & Extraction (Shi-Tomasi/SIFT). Keypoint Matching is done, and the GPUs recover Homography (RANSAC). Next, the GPUs create a Laplacian Pyramid. A Projective Transform is done, and a Multi-Band Blend is the last stage of the pipeline.

Object Recognition

The CPU/GPU can identify video objects and then generate metadata for video objects contained within the captured video frames. For each of the captured video frames, the CPU/GPUs may execute program instructions to: (i) detect whether the video frame contains a video object, (ii) generate meta data for each detected video object, and (iii) cause data storage to store the relevant portions of the video and the metadata describing objects in the video for search purposes.

Generating the metadata may be carried out in various ways. For instance, generating the meta data may be carried out by segmenting video objects within a video frame and then representing features of each segmented video object. As an example, the feature representation may be color appearance information, that is, the analytical data may comprise color data based on the color or colors of a video object. The analytical data based on the color or colors of a video object may include any of a variety of color data. For example, for any given video object, the color data may include Red Green Blue (RGB) color space data, Hue Saturation Value (HSV) color space data, YCrCb color space data, and/or YUV color space data.

As another example, the metadata may include data based on pixel intensity, data indicating which pixels are part of the video object, a unique identifier of the video object, and/or structural information associated with the video object. The structural information may include information pertaining to edges, curvature, and/or texture of the video object, for example. The structural information may include information that indicates how close a structure of the video object matches a circle, rectangle, star, or some other arbitrary shape. The metadata may also include confidence measures of the other types of data in the metadata. The confidence measures may indicate a determination of how likely a video object is a given type of object, such as a vehicle, person, animal, bag, or some other type of object.

In one embodiment, the GPU detects an object using color and then tracks the object by:

1. Create a masking image by comparing each pixel with a target color value. Convert pixels that fall within the range to white, and convert those that fall outside the range to black.
2. Find the centroid of the target color. The centroid of the tracked color defines the center position for the overlay image. A multipass pixel-processing kernel is used to compute a location. The output of this phase is a 1×1-pixel image, containing the coordinate of the centroid in the first two components (pixel.rg) and the area in the third component (pixel.b). The area is used to estimate the distance of the object from the camera.
3. Composite an image over the detected object. Assuming the shape of the object does not change with respect to the frame, then the change in area of the tracked color is proportional to the square of the distance of the object from the viewer. This information is used to scale the overlay image, so that the overlay image increases or decreases in size appropriately.

In another embodiment, Shape-Based Matching (SBM) is used for recognizing partially occluded objects which is very robust against illumination changes. It is closely related to correlation. The main difference is that SBM uses the inner product of normalized edge gradient vectors as similarity measure instead of raw image intensity. To recognize an object, the search image is correlated with the model using the similarity measure of SBM. The model image is fitted in all possible translations within the search image and a score is assigned to each position. As correlation based methods do not cope with any other object transformation those must be handled by evaluating the results of multiple correlations.

In one embodiment, a Hough transform (HT) can be used to recognize any analytically describable shape]. A generalization of the Hough transform (GHT) who manages any discrete shape is also available [1]. Ulrich presents a modification of the generalized Hough transform (MGHT), gaining real-time performance by taking advantage of resolution hierarchies, which is not as straight forward as it might first seem. The principles of it are described below. Initially, a model of the object to be recognized is generated. A gradient map is generated from the model image and edges are extracted. Then a table, mapping edge gradient direction (represented as an angle) to offset vectors to the center of the model, is created.

In the search procedure a gradient map of the search image is used. For each gradient direction (represented as an angle) a number of displacement vectors are looked up using the table. A vote is placed on each position pointed at by a displacement vector. If the point belongs to an edge of the object, at least one of the vectors point at the center of the object that is to be found, and a vote will be placed for that position. After this is done, a peak has appeared in the voting space at the center of the object as this is the single point that the most dislocation vectors points at (at least one for each gradient belonging to the edge of the object in the search image).

To utilize a resolution pyramid the model image is divided into tiles for all levels but the coarsest. A separate lookup table is generated for each tile. Searching then begins with a regular search at the coarsest pyramid level which yields a coarse position of the object which will be refined for each level in the pyramid.

In the refinement, the entire gradient map is considered as before, but only the mapping table connected to the tiles that have dislocation vectors pointing to a neighborhood of the known position are evaluated for each gradient. This way the amount of votes to place, and the voting space itself is much smaller than before.

In another embodiment, a chamfer distance transform of an edge image is used as a model. Another edge image is extracted from the search image. To find the position of the object a similarity measure is evaluated for each potential position (as for cross correlation). The similarity measure is the mean distance from each edge in the search image to the closest edge in the model for the current translation. This is obtained by accumulating samples from the distance map of the model for each edge in the search image. If there is a perfect match, the mean distance is 0.

Other object recognition techniques can be used to tap into the GPU's parallel stream processing.

In an example, images of food can be automatically analyzed in order to identify the types and quantities of food consumed. In an example, pictures of food taken by a camera or other picture-taking device can be automatically analyzed to estimate the types and amounts of specific foods, ingredients, or nutrients that a person is consumes. In an example, an initial stage of an image analysis system can comprise adjusting, normalizing, or standardizing image elements for better food segmentation, identification, and volume estimation. These elements can include: color, texture, shape, size, context, geographic location, adjacent food, place setting context, and temperature (infrared). In an example, a device can identify specific foods from pictures or images by image segmentation, color analysis, texture analysis, and pattern recognition.

In various examples, automatic identification of food types and quantities can be based on: color and texture analysis; image segmentation; image pattern recognition; volumetric analysis based on a fiduciary marker or other object of known size; and/or three-dimensional modeling based on pictures from multiple perspectives. In an example, a device can collect food images that are used to extract a vector of food parameters (such as color, texture, shape, and size) that are automatically associated with vectors of food parameters in a database of such parameters for food identification. In an example, a device can collect food images that are automatically associated with images of food in a food image database for food identification. In an example, specific ingredients or nutrients that are associated with these selected types of food can be estimated based on a database linking foods to ingredients and nutrients. In another example, specific ingredients or nutrients can be measured directly. In various examples, a device for measuring consumption of food, ingredient, or nutrients can directly (or indirectly) measure consumption at least one selected type of food, ingredient, or nutrient.

In an example, selected types of foods, ingredients, and/or nutrients can be identified by the patterns of light that are reflected from, or absorbed by, the food at different wavelengths. In an example, a light-based sensor can detect food consumption or can identify consumption of a specific food, ingredient, or nutrient based on the reflection of light from food or the absorption of light by food at different wavelengths. In an example, an optical sensor can detect fluorescence. In an example, an optical sensor can detect whether food reflects light at a different wavelength than the wavelength of light shone on food. In an example, an optical sensor can be a fluorescence polarization immunoassay sensor, chemiluminescence sensor, thermoluminescence sensor, or piezoluminescence sensor. In an example, a light-based food-identifying sensor can collect information concerning the wavelength spectra of light reflected from, or absorbed by, food. In an example, an optical sensor can be a chromatographic sensor, spectrographic sensor, analytical chromatographic sensor, liquid chromatographic sensor, gas chromatographic sensor, optoelectronic sensor, photochemical sensor, and photocell. In an example, an optical sensor can analyze modulation of light wave parameters by the interaction of that light with a portion of food. In an example, an optical sensor can detect modulation of light reflected from, or absorbed by, a receptor when the receptor is exposed to food. In an example, an optical sensor can emit and/or detect white light, infrared light, or ultraviolet light. In an example, a light-based food-identifying sensor can identify consumption of a selected type of food, ingredient, or nutrient with a spectral analysis sensor. In various examples, a food-identifying sensor can identify a selected type of food, ingredient, or nutrient with a sensor that detects light reflection spectra, light absorption spectra, or light emission spectra. In an example, a spectral measurement sensor can be a spectroscopy sensor or a spectrometry sensor. In an example, a spectral measurement sensor can be a white light spectroscopy sensor, an infrared spectroscopy sensor, a near-infrared spectroscopy sensor, an ultraviolet spectroscopy sensor, an ion mobility spectroscopic sensor, a mass spectrometry sensor, a backscattering spectrometry sensor, or a spectrophotometer. In an example, light at different wavelengths can be absorbed by, or reflected off, food and the results can be analyzed in spectral analysis.

In an example, a food-consumption monitor or food-identifying sensor can be a microphone or other type of sound sensor. In an example, a sensor to detect food consumption and/or identify consumption of a selected type of food, ingredient, or nutrient can be a sound sensor. In an example, a sound sensor can be an air conduction microphone or bone conduction microphone. In an example, a microphone or other sound sensor can monitor for sounds associated with chewing or swallowing food. In an example, data collected by a sound sensor can be analyzed to differentiate sounds from chewing or swallowing food from other types of sounds such as speaking, singing, coughing, and sneezing.

In an example, a sound sensor can include speech recognition or voice recognition to receive verbal input from a person concerning food that the person consumes. In an example, a sound sensor can include speech recognition or voice recognition to extract food selecting, ordering, purchasing, or consumption information from other sounds in the environment.

In an example, a sound sensor can be worn or held by a person. In an example, a sound sensor can be part of a general purpose device, such as a cell phone or mobile phone, which has multiple applications. In an example, a sound sensor can measure the interaction of sound waves (such as ultrasonic sound waves) and food in order to identify the type and quantity of food that a person is eating.

In an example, a food-consumption monitor or food-identifying sensor can be a chemical sensor. In an example, a chemical sensor can include a receptor to which at least one specific nutrient-related analyte binds and this binding action creates a detectable signal. In an example, a chemical sensor can include measurement of changes in energy wave parameters that are caused by the interaction of that energy with food. In an example, a chemical sensor can be incorporated into a smart utensil to identify selected types of foods, ingredients, or nutrients. In an example, a chemical sensor can be incorporated into a portable food probe to identify selected types of foods, ingredients, or nutrients. In an example, a sensor can analyze the chemical composition of a person's saliva. In an example, a chemical sensor can be incorporated into an intraoral device that analyzes microsamples of a person's saliva. In an example, such an intraoral device can be adhered to a person's upper palate.

In various examples, a food-consumption monitor or food-identifying sensor can be selected from the group consisting of: receptor-based sensor, enzyme-based sensor, reagent based sensor, antibody-based receptor, biochemical sensor, membrane sensor, pH level sensor, osmolality sensor, nucleic acid-based sensor, or DNA/RNA-based sensor; a biomimetic sensor (such as an artificial taste bud or an artificial olfactory sensor), a chemiresistor, a chemoreceptor sensor, a electrochemical sensor, an electroosmotic sensor, an electrophoresis sensor, or an electroporation sensor; a specific nutrient sensor (such as a glucose sensor, a cholesterol sensor, a fat sensor, a protein-based sensor, or an amino acid sensor); a color sensor, a colorimetric sensor, a photochemical sensor, a chemiluminescence sensor, a fluorescence sensor, a chromatography sensor (such as an analytical chromatography sensor, a liquid chromatography sensor, or a gas chromatography sensor), a spectrometry sensor (such as a mass spectrometry sensor), a spectrophotometer sensor, a spectral analysis sensor, or a spectroscopy sensor (such as a near-infrared spectroscopy sensor); and a laboratory-on-a-chip or microcantilever sensor.

In an example, a food-consumption monitor or food-identifying sensor can be an electromagnetic sensor. In an example, a device for measuring food consumption or identifying specific nutrients can emit and measure electromagnetic energy. In an example, a device can expose food to electromagnetic energy and collect data concerning the effects of this interaction which are used for food identification. In various examples, the results of this interaction can include measuring absorption or reflection of electromagnetic energy by food. In an example, an electromagnetic sensor can detect the modulation of electromagnetic energy that is interacted with food.

In an example, an electromagnetic sensor that detects food or nutrient consumption can detect electromagnetic signals from the body in response to the consumption or digestion of food. In an example, analysis of this electromagnetic energy can help to identify the types of food that a person consumes. In an example, a device can measure electromagnetic signals emitted by a person's stomach, esophagus, mouth, tongue, afferent nervous system, or brain in response to general food consumption. In an example, a device can measure electromagnetic signals emitted by a person's stomach, esophagus, mouth, tongue, afferent nervous system, or brain in response to consumption of selected types of foods, ingredients, or nutrients.

In various examples, a sensor to detect food consumption or identify consumption of a selected type of nutrient can be selected from the group consisting of: neuroelectrical sensor, action potential sensor, ECG sensor, EKG sensor, EEG sensor, EGG sensor, capacitance sensor, conductivity sensor, impedance sensor, galvanic skin response sensor, variable impedance sensor, variable resistance sensor, interferometer, magnetometer, RF sensor, electrophoretic sensor, optoelectronic sensor, piezoelectric sensor, and piezocapacitive sensor.

In an example, a food-consumption monitor or food-identifying sensor can be a location sensor. In an example, such a sensor can be geographic location sensor or an intra-building location sensor. A device for detecting food consumption and/or indentifying a selected type of food, ingredient, or nutrient consumed can use information concerning a person's location as part of the means for food consumption detection and/or food identification. In an example, a device can identify when a person in a geographic location that is associated with probable food consumption. In an example, a device can use information concerning the person's geographic location as measured by a global positioning system or other geographic location identification system. In an example, if a person is located at a restaurant with a known menu or at a store with a known food inventory, then information concerning this menu or food inventory can be used to narrow down the likely types of food being consumed. In an example, if a person is located at a restaurant, then the sensitivity of automated detection of food consumption can be adjusted. In an example, if a person is located at a restaurant or grocery store, then visual, auditory, or other information collected by a sensor can be interpreted within the context of that location.

In an example, a device can identify when a person is in a location within a building that is associated with probable food consumption. In an example, if a person is in a kitchen or in a dining room within a building, then the sensitivity of automated detection of food consumption can be adjusted. In an example, a food-consumption monitoring system can increase the continuity or level of automatic data collection when a person is in a restaurant, in a grocery store, in a kitchen, or in a dining room. In an example, a person's location can be inferred from analysis of visual signals or auditory signals instead of via a global positioning system. In an example, a person's location can be inferred from interaction between a device and local RF beacons or local wireless networks.

In an example, a sensor to monitor, detect, or sense food consumption or to identify consumption of a selected type of food, ingredient, or nutrient can be a wearable sensor that is worn by the person whose food consumption is monitored, detected, or sensed. In an example, a wearable food-consumption monitor or food-identifying sensor can be worn directly on a person's body. In an example a wearable food-consumption monitor or food-identifying sensor can be worn on, or incorporated into, a person's clothing.

In various examples, a device for measuring a person's consumption of at least one selected type of food, ingredient, or nutrient can provide feedback to the person that is selected from the group consisting of: feedback concerning food consumption (such as types and amounts of foods, ingredients, and nutrients consumed, calories consumed, calories expended, and net energy balance during a period of time); information about good or bad ingredients in nearby food; information concerning financial incentives or penalties associated with acts of food consumption and achievement of health-related goals; information concerning progress toward meeting a weight, energy-balance, and/or other health-related goal; information concerning the calories or nutritional components of specific food items; and number of calories consumed per eating event or time period.

In various examples, a device for measuring a person's consumption of at least one selected type of food, ingredient, or nutrient can provide feedback to the person that is selected from the group consisting of: augmented reality feedback (such as virtual visual elements superimposed on foods within a person's field of vision); changes in a picture or image of a person reflecting the likely effects of a continued pattern of food consumption; display of a person's progress toward achieving energy balance, weight management, dietary, or other health-related goals; graphical display of foods, ingredients, or nutrients consumed relative to standard amounts (such as embodied in pie charts, bar charts, percentages, color spectrums, icons, emoticons, animations, and morphed images); graphical representations of food items; graphical representations of the effects of eating particular foods; holographic display; information on a computer display screen (such as a graphical user interface); lights, pictures, images, or other optical feedback; touch screen display; and visual feedback through electronically-functional eyewear.

In various examples, a device for measuring a person's consumption of at least one selected type of food, ingredient, or nutrient can provide feedback to the person that is selected from the group consisting of: advice concerning consumption of specific foods or suggested food alternatives (such as advice from a dietician, nutritionist, nurse, physician, health coach, other health care professional, virtual agent, or health plan); electronic verbal or written feedback (such as phone calls, electronic verbal messages, or electronic text messages); live communication from a health care professional; questions to the person that are directed toward better measurement or modification of food consumption; real-time advice concerning whether to eat specific foods and suggestions for alternatives if foods are not healthy; social feedback (such as encouragement or admonitions from friends and/or a social network); suggestions for meal planning and food consumption for an upcoming day; and suggestions for physical activity and caloric expenditure to achieve desired energy balance outcomes.

In an example, a device for measuring a person's consumption of at least one selected type of food, ingredient, or nutrient can identify and track the selected types and amounts of foods, ingredients, or nutrients that the person consumes in an entirely automatic manner. In an example, such identification can occur in a partially automatic manner in which there is interaction between automated and human identification methods.

In an example, a device for measuring a person's consumption of at least one selected type of food, ingredient, or nutrient can identify and track food consumption at the point of selection or point of sale. In an example, a device for monitoring food consumption or consumption of selected types of foods, ingredients, or nutrients can approximate such measurements by tracking a person's food selections and purchases at a grocery store, at a restaurant, or via a vending machine. Tracking purchases can be relatively easy to do, since financial transactions are already well-supported by existing information technology. In an example, such tracking can be done with specific methods of payment, such as a credit card or bank account. In an example, such tracking can be done with electronically-functional food identification means such as bar codes, RFID tags, or electronically-functional restaurant menus. Electronic communication for food identification can also occur between a food-consumption monitoring device and a vending machine.

In an example, a device for measuring a person's consumption of at least one selected type of food, ingredient, or nutrient can identify food using information from a food's packaging or container. In an example, this information can be detected optically by means of a picture or optical scanner. In an example, food can be identified directly by automated optical recognition of information on food packaging, such as a logo, label, or barcode. In various examples, optical information on a food's packaging or container that is used to identify the type and/or amount of food can be selected from the group consisting of: bar code, food logo, food trademark design, nutritional label, optical text recognition, and UPC code. With respect to meals ordered at restaurants, some restaurants (especially fast-food restaurants) have standardized menu items with standardized food ingredients. In such cases, identification of types and amounts of food, ingredients, or nutrients can be conveyed at the point of ordering (via an electronically-functional menu) or purchase (via purchase transaction). In an example, food can be identified directly by wireless information received from a food display, RFID tag, electronically-functional restaurant menu, or vending machine. In an example, food or its nutritional composition can be identified directly by wireless transmission of information from a food display, menu, food vending machine, food dispenser, or other point of food selection or sale and a device that is worn, held, or otherwise transported with a person.

However, there are limitations to estimating food consumption based on food selections or purchases in a store or restaurant. First, a person might not eat everything that they purchase through venues that are tracked by the system. The person might purchase food that is eaten by their family or other people and might throw out some of the food that they purchase. Second, a person might eat food that they do not purchase through venues that are tracked by the system. The person might purchase some food with cash or in venues that are otherwise not tracked. The person might eat food that someone else bought, as when eating as a guest or family member. Third, timing differences between when a person buys food and when they eat it, especially for non-perishable foods, can confound efforts to associate caloric intake with caloric expenditure to manage energy balance during a defined period of time. For these reasons, a robust device for measuring food consumption should (also) be able to identify food at the point of consumption.

In an example, a device, method, or system for measuring a person's consumption of at least one selected type of food, ingredient, or nutrient can identify and track a person's food consumption at the point of consumption. In an example, such a device, method, or system can include a database of different types of food. In an example, such a device, method, or system can be in wireless communication with an externally-located database of different types of food. In an example, such a database of different types of food and their associated attributes can be used to help identify selected types of foods, ingredients, or nutrients. In an example, a database of attributes for different types of food can be used to associate types and amounts of specific ingredients, nutrients, and/or calories with selected types and amounts of food.

In an example, such a database of different types of foods can include one or more elements selected from the group consisting of: food color, food name, food packaging bar code or nutritional label, food packaging or logo pattern, food picture (individually or in combinations with other foods), food shape, food texture, food type, common geographic or intra-building locations for serving or consumption, common or standardized ingredients (per serving, per volume, or per weight), common or standardized nutrients (per serving, per volume, or per weight), common or standardized size (per serving), common or standardized number of calories (per serving, per volume, or per weight), common times or special events for serving or consumption, and commonly associated or jointly-served foods.

In an example, a picture of a meal as a whole can be automatically segmented into portions of different types of food for comparison with different types of food in a food database. In an example, the boundaries between different types of food in a picture of a meal can be automatically determined to segment the meal into different food types before comparison with pictures in a food database. In an example, a picture of a meal with multiple types of food can be compared as a whole with pictures of meals with multiple types of food in a food database. In an example, a picture of a food or a meal comprising multiple types of food can be compared directly with pictures of food in a food database.

In an example, a picture of food or a meal comprising multiple types of food can be adjusted, normalized, or standardized before it is compared with pictures of food in a food database. In an example, food color can be adjusted, normalized, or standardized before comparison with pictures in a food database. In an example, food size or scale can be adjusted, normalized, or standardized before comparison with pictures in a food database. In an example, food texture can be adjusted, normalized, or standardized before comparison with pictures in a food database. In an example, food lighting or shading can be adjusted, normalized, or standardized before comparison with pictures in a food database.

In an example, a food database can be used to identify the amount of calories that are associated with an identified type and amount of food. In an example, a food database can be used to identify the type and amount of at least one selected type of food that a person consumes. In an example, a food database can be used to identify the type and amount of at least one selected type of ingredient that is associated with an identified type and amount of food. In an example, a food database can be used to identify the type and amount of at least one selected type of nutrient that is associated with an identified type and amount of food. In an example, an ingredient or nutrient can be associated with a type of food on a per-portion, per-volume, or per-weight basis.

In an example, a vector of food characteristics can be extracted from a picture of food and compared with a database of such vectors for common foods. In an example, analysis of data concerning food consumption can include comparison of food consumption parameters between a specific person and a reference population. In an example, data analysis can include analysis of a person's food consumption patterns over time. In an example, such analysis can track the cumulative amount of at least one selected type of food, ingredient, or nutrient that a person consumes during a selected period of time.

In various examples, data concerning food consumption can be analyzed to identify and track consumption of selected types and amounts of foods, ingredients, or nutrient consumed using one or more methods selected from the group consisting of: linear regression and/or multivariate linear regression, logistic regression and/or probit analysis, Fourier transformation and/or fast Fourier transform (FFT), linear discriminant analysis, non-linear programming, analysis of variance, chi-squared analysis, cluster analysis, energy balance tracking, factor analysis, principal components analysis, survival analysis, time series analysis, volumetric modeling, neural network and machine learning.

In an example, a device for measuring a person's consumption of at least one selected type of food, ingredient, or nutrient can identify the types and amounts of food consumed in an automated manner based on images of that food. In various examples, food pictures can be analyzed for automated food identification using methods selected from the group consisting of: image attribute adjustment or normalization; inter-food boundary determination and food portion segmentation; image pattern recognition and comparison with images in a food database to identify food type; comparison of a vector of food characteristics with a database of such characteristics for different types of food; scale determination based on a fiduciary marker and/or three-dimensional modeling to estimate food quantity; and association of selected types and amounts of ingredients or nutrients with selected types and amounts of food portions based on a food database that links common types and amounts of foods with common types and amounts of ingredients or nutrients. In an example, automated identification of selected types of food based on images and/or automated association of selected types of ingredients or nutrients with that food can occur within a wearable or hand-held device. In an example, data collected by a wearable or hand-held device can be transmitted to an external device where automated identification occurs and the results can then be transmitted back to the wearable or hand-held device.

In an example, a device and system for measuring a person's consumption of at least one selected type of food, ingredient, or nutrient can take pictures of food using a digital camera. In an example, a device and system for measuring a person's consumption of at least one selected type of food, ingredient, or nutrient can take pictures of food using an imaging device selected from the group consisting of: smart watch, smart bracelet, fitness watch, fitness bracelet, watch phone, bracelet phone, wrist band, or other wrist-worn device; arm bracelet; and smart ring or finger ring. In an example, a device and system for measuring a person's consumption of at least one selected type of food, ingredient, or nutrient can take pictures of food using an imaging device selected from the group consisting of: smart phone, mobile phone, cell phone, holophone, and electronic tablet.

In an example, a device and system for measuring a person's consumption of at least one selected type of food, ingredient, or nutrient can take pictures of food using an imaging device selected from the group consisting of: smart glasses, visor, or other eyewear; electronically-functional glasses, visor, or other eyewear; augmented reality glasses, visor, or other eyewear; virtual reality glasses, visor, or other eyewear; and electronically-functional contact lens. In an example, a device and system for measuring a person's consumption of at least one selected type of food, ingredient, or nutrient can take pictures of food using an imaging device selected from the group consisting of: smart utensil, fork, spoon, food probe, plate, dish, or glass; and electronically-functional utensil, fork, spoon, food probe, plate, dish, or glass. In an example, a device and system for measuring a person's consumption of at least one selected type of food, ingredient, or nutrient can take pictures of food using an imaging device selected from the group consisting of: smart necklace, smart beads, smart button, neck chain, and neck pendant.

In an example, an imaging device can take multiple still pictures or moving video pictures of food. In an example, an imaging device can take multiple pictures of food from different angles in order to perform three-dimensional analysis or modeling of the food to better determine the volume of food. In an example, an imaging device can take multiple pictures of food from different angles in order to better control for differences in lighting and portions of food that are obscured from some perspectives. In an example, an imaging device can take multiple pictures of food from different angles in order to perform three-dimensional modeling or volumetric analysis to determine the three-dimensional volume of food in the picture. In an example, an imaging device can take multiple pictures of food at different times, such as before and after an eating event, in order to better determine how much food the person actually ate (as compared to the amount of food served). In an example, changes in the volume of food in sequential pictures before and after consumption can be compared to the cumulative volume of food conveyed to a person's mouth by a smart utensil to determine a more accurate estimate of food volume consumed. In various examples, a person can be prompted by a device to take pictures of food from different angles or at different times.

In an example, a device that identifies a person's food consumption based on images of food can receive food images from an imaging component or other imaging device that the person holds in their hand to operate. In an example, a device that identifies a person's food consumption based on images of food can receive food images from an imaging component or other imaging device that the person wears on their body or clothing. In an example, a wearable imaging device can be worn in a relatively fixed position on a person's neck or torso so that it always views the space in front of a person. In an example, a wearable imaging device can be worn on a person's wrist, arm, or finger so that the field of vision of the device moves as the person moves their arm, wrist, and/or fingers. In an example, a device with a moving field of vision can monitor both hand-to-food interaction and hand-to-mouth interaction as the person moves their arm, wrist, and/or hand. In an example, a wearable imaging device can comprise a smart watch with a miniature camera that monitors the space near a person's hands for possible hand-to-food interaction and monitors the near a person's mouth for hand-to-mouth interaction.

In an example, selected attributes or parameters of a food image can be adjusted, standardized, or normalized before the food image is compared to images in a database of food images or otherwise analyzed for identifying the type of food. In various examples, these image attributes or parameters can be selected from the group consisting of: food color, food texture, scale, image resolution, image brightness, and light angle.

In an example, a device and system for identifying types and amounts of food consumed based on food images can include the step of automatically segmenting regions of a food image into different types or portions of food. In an example, a device and system for identifying types and amounts of food consumed based on food images can include the step of automatically identifying boundaries between different types of food in an image that contains multiple types or portions of food. In an example, the creation of boundaries between different types of food and/or segmentation of a meal into different food types can include edge detection, shading analysis, texture analysis, and three-dimensional modeling. In an example, this process can also be informed by common patterns of jointly-served foods and common boundary characteristics of such jointly-served foods.

In an example, estimation of specific ingredients or nutrients consumed from information concerning food consumed can be done using a database that links specific foods (and quantities thereof) with specific ingredients or nutrients (and quantities thereof). In an example, food in a picture can be classified and identified based on comparison with pictures of known foods in a food image database. In an example, such food identification can be assisted by pattern recognition software. In an example, types and quantities of specific ingredients or nutrients can be estimated from the types and quantities of food consumed.

In an example, attributes of food in an image can be represented by a multi-dimensional food attribute vector. In an example, this food attribute vector can be statistically compared to the attribute vector of known foods in order to automate food identification. In an example, multivariate analysis can be done to identify the most likely identification category for a particular portion of food in an image. In various examples, a multi-dimensional food attribute vector can include attributes selected from the group consisting of: food color; food texture; food shape; food size or scale; geographic location of selection, purchase, or consumption; timing of day, week, or special event; common food combinations or pairings; image brightness, resolution, or lighting direction; infrared light reflection; spectroscopic analysis; and person-specific historical eating patterns.

An embodiment provides a system and a method for rendering augmented/virtual reality content and enabling users to modify the augmented reality content. The system may include one or more image capturing devices through which data from the instant surrounding of the user may be captured. Further, the system may communicate with one or more multimedia content servers to access files from the multimedia content servers. Such files may be stored in a database within the system. Examples of multimedia files may include images, text and icons or moving content such as video clips, among others. The system may render augmented reality content to be displayed to the user by integrating the data captured through the image capturing device and data retrieved from the multimedia servers in the database. The system may include one or more sensors through which input may be provided to a processor. The input may for example include data corresponding to tactile data, gestures data, movement and positional data of the user, among others. Semantics corresponding to such input may be stored in a gesture recognition database. The system may further determine one or more outcomes based on the input received through the sensors. The outcomes corresponding to the input may be stored in the gesture recognition database, which is accessible to the processor. One or more objects of the augmented reality content may be altered by applying the outcomes based on the input to the content that is presented to the user. The augmented reality content may be presented on an augmented/virtual reality display device which may be integrated with the system.

Alternatively, the virtual/augmented reality content may be projected on surfaces such as for example, walls, tables, floors and ceilings, among others. The virtual reality content may be displayed either in two dimensional or three dimensional formats. A rendering module may render the content to be displayed such that, the user may experience the event occurring in a three-dimensional space and interact with the contents of the event.

Another embodiment provides a system for enabling a plurality of users to participate in an activity and communicate in virtual reality. The system may be implemented in a plurality of scenarios where the user of the system, while being engaged in an activity, may be willing to experience the virtual presence of other users, taking part in the same activity, while the activity is in progress. For example, the system may be used in a scenario when the user is performing yoga at home. The user may be willing to experience the virtual presence of one or more of his friends performing yoga beside him. The system may be configured to render virtual content showing virtual images or videos of one or more other users who may or may not be performing yoga. The users may be able to communicate with one another through voice or text or both voice and text. The system may be used in all possible scenarios where virtual interaction may be desired by the user with his/her family, friends or any person whom the user may be interested in interacting virtually. One or more of the other users may be connected to the user on one or more social networking platforms. The system may retrieve information corresponding to the other users, who may be connected to the user on one or more social networking platforms by accessing the user's profile. The system may be configured to render a virtual reality environment based on the type of activity the user may be engaged in. The processor, input units, database, image capturing device may be embedded within the augmented/virtual reality (AR/VR) devices. Each user participating in an activity in virtual reality with one another may interact through their respective AR/VR devices.

The database may include information corresponding to the user's profile as retrieved from one or more social networking platforms. Alternatively, the user may feed data corresponding to his profile in the system, which may be stored in the database. The database may communicate with servers associated with one or more social networking portals and retrieve the user's relationship information with other users on the portal. Profiles of a plurality of users with whom the user may be connected may be stored in the database. Such information may also be fed into the system by the user and may be stored in the database. The system may be configured to generate virtual content based on the user's profile information and profiles of the plurality of users stored in the database. The database may also store preconfigured profiles of users who may not be connected with the user. Such profiles may include profiles of celebrities, animated characters or other profiles or personalities in whom the user may have shown interest. The processor may be configured to access the database and generate content based on the user's preference and profile. The database may store a set of preconfigured or configurable rules that the processor may access to determine the type of content to be rendered based on at least the preference and profile of the user for whom the content is to be displayed.

One method provides rendering virtual reality content to be displayed to the user, based on the input provided by the user, in accordance with an embodiment. At step 502, the system may receive input from the user. Such input may be information corresponding to what type of content the user is interested in viewing. The input may be provided through a physical keypad, which may be connected to the system or a virtual keypad that the system provides to the user. Alternatively, such input may also be provided by the user by touching or tapping options being provided to the user on a display interface. Such input may also be provided through voice. At step 504, the input received at the previous step may be communicated to the processor. At step 506, the processor may assess the input. At step 508, the processor may retrieve content based on the input. The content may be retrieved by accessing the multimedia servers or the database 308. At step 510, the retrieved content may be integrated with the images received from the image-capturing device 312. For this purpose, the processor may determine interest points, define interest operators and construct an optical flow of the images of the instant environment captured through the image capturing device 312. The instant surrounding's pixel coordinates may be determined from the data obtained by processing the image. The processor, upon receiving input from users about the type or theme of the content to be rendered, may generate the image and, subsequently, determine the interest points, define interest operators and construct an optical flow of the virtual images that may be retrieved from the multimedia content. At step 512, the rendering module 304 of the processor may render the integrated content into two or three dimensional content by integrating the content depicting the images from the physical world. At step 514, the rendered content may be communicated to the AR device to be displayed to the user. The AR device may display the content on the AR display device or a surface such as a wall, floor, table and ceilings, among others. The display surface may depend on the type of AR device. For example, if the AR device is a device worn like an eyewear, the display may be on the AR device's display surface. If the AR device is a head mounted device, then the display surface may be one or more of the display surfaces mentioned above. The processor may be a self learning artificially intelligent processor to determine the type of content to be presented to the user. The processor may learn from previous activities or selections made by the user and take into consideration such information while generating the content including the virtual images to be integrated with the images of the surroundings.

The sensors may receive inputs corresponding to parameters indicating a set of defined user characteristics. Characteristics may, for example, include head movement speed, head movement acceleration, and/or relationship between head movement and eye movement (e.g., ratio of one to the other), limb movement speed. The characteristics may even include indications of the tendency of a user to pay attention to certain virtual objects such as virtual object type (e.g., text, charts), movement of a virtual object (e.g., large shifts from image to image, fast or rapid movement, direction of movement), and characteristics of the virtual object (e.g., color, brightness, size), among others.

The user's eye and head movements and changes in position may be constantly monitored for displaying virtual content. A sensor, such as a position sensor may be integrated in the AR device which may be configured to monitor the viewer's (user) head and eye positions. The position information may be constantly communicated to the processor and stored in the database 308. The processor may determine the direction of light entering into the eye depending on the eye position. The line of sight may also be determined based on the eye position. The virtual content may be displayed to the user, based on the line of sight of the user.

In another method of displaying virtual reality content to the user, in accordance with an embodiment, at step 602, the user's eye position may be constantly monitored by the augmented reality device. At step 604, the information relating to the eye position may be constantly communicated to the processor. Such information may include how fast the eye movement changes, the position of the eye for each change and the line of sight, among others. Such information may be stored in the database 308 and retrieved by the processor to determine the instantaneous velocity at which the eye may move. At step 606, the processor may determine the corresponding direction of projection of light into the eye depending on the eye position. The determined direction of projection of light into the eye depending on the eye position may be stored in the database 308 for the processor to retrieve in future. At step 608, the rendering module 304 of the processor may carry out rendering of content into two or three-dimensional formats. At step 610, the processor may communicate the rendered content, along with instructions of direction of projection of light to the AR device. At step 612, the AR device may receive the content along with instructions related to the direction of projection of light and thereafter project the content into the eye of the user such that, the user sees the content in two or three-dimensional formats. The processor may further determine the velocity at which frames of images may be rendered based on the user's eye position. The processor may estimate an instantaneous velocity at which the eye position changes and the information relating to the velocity may be communicated to the rendering module 304, such that images may be presented as continuous scene according to change in position of the eye.

A method of displaying virtual reality content to the user, such that the content is clearly visible to the user, is detailed next. At step 702, the AR device may determine the intensity of light of the instant surrounding in the user's line of sight. At step 704, the AR device may communicate the information relating to the intensity of light to the processor. Such information may include information corresponding to ambient lighting of the environment, brightness of the objects and foreground and background lighting, among others. At step 706, the processor may receive the information and determines the intensity of light to be projected into the user's eyes, such that, the content is clearly visible to the user. For example, the processor may determine the intensity of light to be projected into the user's eye such that the user is clearly able to view an image of the surrounding, depending on the amount of brightness or darkness of the instant surrounding. The processor may define areas of brightness and darkness in a scene and accordingly execute image correction algorithms and apply it on the images to be rendered. At step 708, the rendering module 304 of the processor may render the content to be displayed to the user based on the determination of intensity of light by the processor. At step 710, the content may be communicated to the AR device, to be displayed to the user such that, the content is clearly visible to the user.

One or more sensors may receive input such as, tactile and gesture input, data indicating pressure and force vectors, applied through the user's limbs, among others. In an embodiment, the processor may further receive voice data from the one or more sensors such as a microphone. This may be voice input provided by the user, wherein the voice input may correspond to a command. The processor may be configured to receive input from the sensors and synthesize the input and derive the visual output or outcome based on the input. The derived visual output may be applied to the virtual images to alter one or more parameters (location, size etc) of the objects in the image. For example, in a car racing game, the input may correspond to pitch, yaw or roll data of a user's limbs. The user may change the position of the hands to steer a vehicle in the game, thereby altering the pitch, yaw or roll values of the hands. The processor may determine the outcomes of the pitch, yaw and roll data and their effect on the content. The outcome, for example, may be, steering the vehicle to the left or right, or increasing or decreasing the speed of the vehicle.

In an embodiment, the gesture recognition database 310 may store gestures along with the semantics of each gesture received through the sensors. The semantics of the gestures may be predefined and stored in the gesture recognition database 310. The gesture recognition database 310 may also store outcomes of such input. The outcomes may indicate one or more physical actions carried by the user which may be applied to the virtual content to modify or alter parameters of the content. For example, if the user were to provide a gesture indicating expanding or zooming a particular object which is displayed to the user, the outcome would be zooming of the object. The gesture can be the action of zooming with his fingers. The system may receive the input and accesses the gesture recognition database 310 to determine the outcome of the gesture input. The rendering module 304 may receive the outcome of the gesture input and render it in real time to the virtual content in order to alter details of the content. The gesture inputs may for example imply, resizing, adding, deleting, and shifting one or more items or objects of the content from one location to another. Gesture input may not only be limited to gestures made with fingers or hand, such input may also include tactile input, voice input and movement data of the user, among others.

The system can receive gesture input from the user and thereafter rendering content to be displayed to the user, based on the gesture input, in accordance with an embodiment. At step 802, rendered content may be displayed to user. This rendered content may include the image of the instant surrounding combined with the images of virtual objects. At step 804, user input may be provided in form of gestures. At step 806, sensors and image or sound capturing device may capture the gesture. The image-capturing device 312 may be the image-capturing device that may be implemented to capture gestures. Sound may be captured through one or more microphones. These devices may be the parts of the input unit 306. These devices may be integrated into the system or may be peripheral devices connected to the system. Such devices may be detachable from the system. At step 808, the input gesture may be communicated to the processor. The processor may communicate with the gesture recognition database 310 to find the semantics of such input and derive an outcome corresponding to the input. At step 810, the processor may access the gesture recognition database 310 to determine corresponding outcome to the gesture input. At step 812, the processor may find the corresponding outcome to the gesture input. If the processor is able to find the outcome corresponding to the gesture input, then at step 814, the outcome corresponding to the gesture input may be communicated to the processor. If the processor is not able to find the outcome corresponding to the gesture input at step 812, then at step 816, the user may be provided an option to provide an outcome corresponding gesture which will be stored in the gesture recognition database 310. The user may provide outcome corresponding to the gestures through virtual keypads that may be displayed to the user. The user may also provide such input through a physical keypad connected to the system. At step 818, the rendering module 304 of the processor may render the outcome of the input gesture into the two or three dimensional augmented reality content. At step 820, the rendered content may be communicated to the AR device to be displayed to the user. The outcome of the gestures may be used to alter, edit, add or delete one or more content in the images that are presented as the augmented reality content. The corresponding outcome may define one or more physical activities performed by the user such as, pointing at some object, moving an object, scrolling, deleting an object, adding objects, walking in virtual reality and speaking, among others. Some or all of the virtual reality content may get altered based on the input provided by the user.

As an example, the rendering module 304 may render the image of a desktop in either 2 dimensional or 3 dimensional form. The user may have set a password for one particular file on the actual desktop. The user may be currently viewing the desktop in virtual reality and the password protected file needs to be unlocked. The user may use the virtual keypad to enter input mapping to the password which may result in unlocking the file on the virtual as well as actual desktop. In another example, the user may be enabled to unlock a programme or show on a television in virtual reality. The system may also enable locking and unlocking of physical or mechanical locks to virtual doors, gates and cars, among others. For example, a door may be rendered in virtual reality and the user may be required to walk through the door which is locked using a mechanical lock. The user may make gestures in space. The gesture may be communicated to the processor to determine the outcome that may imply an unlocking action. The outcome may be rendered to the virtual reality content, thereby allowing the user to unlock the door.

In another example, the system may display a virtual desktop. The files in the desktop may be arranged and displayed on the left side of the desktop. The user may require moving a file from the left hand side of the virtual desktop to the right hand side or to the taskbar of the virtual desktop. The user may use the physical or virtual keypad to enter inputs to the content that may be used to alter the file location on the virtual desktop. Alternatively, user may provide a gesture indicating moving the file from the left hand side to the right hand side. The gesture input may be communicated to the processor through the motion sensors. The processor may determine the outcome of the gesture and communicate the implication of the outcome to the rendering module 304. The rendering module 304 may render the implication and display the change in the virtual content by moving the file from the original position to the desired position.

In yet another example, the user may be enabled to alter content in a virtual football game. The user may be required to run and kick the ball by moving his feet in space to score goals. Pressure sensors may communicate the pressure and force applied by the user's feet. The user may be required to provide an input indicating forwarding the ball to another player. The motion, force and pressure vectors may be taken into account to determine the direction and force at which the ball may move. The output data corresponding to movements of the user's limbs may be rendered on the display. Whether a goal is being scored or whether the user has made a successful pass to another player may be rendered on the virtual reality content display based on the user's inputs.

In an alternate embodiment, the processor may be configured to receive input from the virtual or physical keypad to alter or modify one or more details or objects of the virtual reality content.

The system can change virtual reality content being altered by the outcome of a gesture input, in accordance with an embodiment. The virtual content is being displayed to the user. The user may wish to view a particular object in the content by expanding the dimensions of the virtual object. The user may provide gesture with his fingers, which may correspond to expand. The portion of the content may be altered by rendering the outcome of the corresponding gesture.

In an embodiment, the depth of field of the user's eye may be calculated based on the eye movement and positions. The rendering module 304 may be configured to render the content into one or more resolutions to enable highlighting certain aspects of the content compared to other aspects of the content. For example, the content in the foreground may be of higher resolution compared to the content in the background. This may enable the user to have a more realistic view of the content, wherein objects nearer to the user are more pronounced in the visibility compared to objects which are farther from the user. The measure of depth of field may and the content being rendered based on the measurement may be applicable in enabling a user to view content in either two or three dimensional formats.

In an embodiment, the field of view of the user's eye may also be calculated based on the eye movement and positions.

The field of view may be used to determine the extent to which the user may view the instant surrounding at any given instant.

The system includes displaying virtual reality content to the user considering the field of view and depth of field of the user, in accordance with an embodiment. At step 902, the AR device may constantly track the eye movement of the user. At step 904, the information related to the eye movement of the user may be constantly communicated to the processor. Such information may include how fast or slow the user' eye may move and change its position and line of sight, among others. Upon receiving the information related to the eye movement of the user, at step 906, the processor may determine the field of view and depth of field of the user's eye. At step 908, the rendering module 304 of the processor may render the content into two or three-dimensional formats taking into consideration field of view and depth of field of the user. At step 910, the rendered content may be communicated to the AR device to be displayed to the user. The user's head position may be constantly changing and the eye position may change relative to the movement of the head. The field of view of the user's eye may be calculated based on the line of sight and the position of the eye. Additionally, the horizontal and vertical field of view of the image-capturing device 312 or the focal length of the image-capturing device 312 may be measured to calculate the field of view of the user's eye.

Further, the rendering module 304 of the processor may render the virtual reality content based on the user's position and orientation. The rendering module 304 may receive from the processor data corresponding to the user's position and orientation. The processor may include pre-configured set of rules pertaining to the user's preferences of the format of display based on the user's position and orientation.

Another system can render virtual reality content based on the display surface, in accordance with an embodiment. At step 1002, the user's position and orientation information may be received through the sensors. At step 1004, the user's position and orientation information may be communicated to the processor. Such information may include information corresponding to a user's position such as sitting, standing, walking and lying in a horizontal position, among others. At step 1006, the processor determines the display surface relative to the user's position and orientation. At step 1008, the processor may communicate the information relating to the display surface to the rendering module 304 along with the preferable formats of display such as two or three-dimensional formats. At step 1010, the rendered content may be communicated to the AR device for display along with the formats the content to be displayed.

Displays may be presented to the user based on the user's position and orientation, in accordance with an embodiment. As an example, the user may be presented a holographic display interface based on the position and orientation. Users may be provided options to choose interfaces based on preference, location and orientation, among others. For example, one interface could be displayed while the user is working or taking part in a conference or event, another interface could be displayed while the user is participating in a leisurely activity such as a game. Furthermore, another interface could be displayed while the user is sitting on a couch and watching a movie. Each of these display interfaces may be different from one another. Each of these display interfaces may be configured to display virtual reality content based on the user's position data, movement data, orientation of head and eyes and orientation of limbs, among others.

Further, the display interfaces may be changed for the user based on the theme of the content being displayed. For example, when the user is watching a movie on Netflix, the display interface may be different from the display interface that is presented while the user is watching sports on ESPN. For example, while watching ESPN posters of players or advertisements may be rendered for display on blank walls.

The processor may be a self learning artificially intelligent processor to determine the format of display to be presented, based on the user's position and orientation. Upon rendering the content based on the user's position and orientation, the virtual reality content may be communicated to the VR device to be displayed on the display surface. As an example, if the user is sitting on a couch and the head is tilted towards the right, the display may also be tilted relative to the position of the head. Further, relative to the overall orientation of the user's body, the display surface may be selected by the system, such as, wall, ceiling and floor, among others. Furthermore, the display may be a curved display of a straight display. The virtual reality content may be rendered to be displayed on curved display surfaces. The virtual reality content or at least a portion of the content may be remapped such that the virtual reality content may be displayed on curved display surfaces. The rendering module 304 may remap the virtual reality content and render the content to be displayed on curved surfaces.

The rendering module 304 may render two dimensional or three dimensional visual content for display based on the user's position and orientation data. The virtual reality content may, as an example, also be displayed or projected in space as holographic display.

Referring to FIG. 12, in another embodiment the system may enable a plurality of users to participate in an activity and communicate, in virtual reality. The system may include a communication module 1202. The system may be configured to communicate with one or more remote servers 1204 via the communication module 1202. The system may be located on a server which may not be located on the VR device and the system may be configured to communicate with the VR device. Alternatively, the system may be located on the VR device. The VR device may project the virtual content based on the instructions received from the processor. The virtual content may be images of other users or videos of other users. The system may include one or more image capturing devices. The rendering module 304 may be configured to render virtual content in one or more formats upon receiving instruction from the processor.

In an embodiment, the system may be configured to communicate with one or more servers 1204 to retrieve user information. The communication module 1202 may enable the system to communicate with the servers 1204. The communication module 1202 may also enable communication of data from the processor to the AR device. The processor may be configured to store information retrieved from the server 1204 in the database 308. The stored information may be information corresponding to the user's profile, relationship information with other users on one or more social networking platforms and one or more activities the user may be performing, among others. Based on the data stored, the processor may generate lists of preconfigured themes that may represent the activities of the user. The user may be provided an option to select one or more themes depending on the type of the activity, the user may be indulged in. Such lists may be provided to the user on a virtual interface such that the user may select one or more options from the lists.

FIG. 13A is a flowchart illustrating the method of rendering virtual content based on the theme or the type of activity the user may be performing, in accordance with an embodiment. At step 1302, the processor may communicate with one or more remote servers 1204 to retrieve information corresponding to the user. At step 1304, the processor may store in the database 308, information or data corresponding to one or more activities that the user may perform. At step 1306, the processor may generate a plurality of lists of preconfigured themes that may be based on the activities. At step 1308, the processor may enable the user to select one or more options from among the lists of themes, which may be based on the type of activity the user may be involved in. At step 1310, the processor may render virtual content based on the theme or type of activity selected by the first user.

Further, a set of machine learning algorithms may enable the processor to learn from the previous choices of theme for an activity selected by the user and thereby automatically select themes based on the activity of the user. Machine learning algorithms may be stored in the database 308 and accessed by the processor. Upon selecting the theme, content may be rendered into virtual reality. Further, the user may be required to provide necessary additional information such that the processor may be able to select the theme based on input provided by the user. Such content may correspond to sceneries that may be able to provide the user experience of the activity the user may be participating in.

FIG. 13B is another flowchart illustrating the method of rendering virtual content to the user based on the theme or the type of activity the user may be performing, in accordance with an embodiment. At step 1312, the processor may communicate with one or more remote servers 1204 to retrieve information corresponding to the user. At step 1314, the processor may learn from the previous activities of the user, choice of themes by the user, relationships, preferences, hobbies, work schedule among other information and store the information in the database 308. At step 1316, the processor may determine the type of activity the user may be performing. At step 1318, the processor may determine the type of content that has to be rendered based on the determination of the activity. At step 1320, the processor may render at least a portion of the virtual content based on the type of activity. Such virtual content rendered at this step may be only a portion of the entire content, such as, for example, the background and scenery that may form the background, among others. Such content may also include one or more other participant's virtual model. At step 1322, whether the virtual content matches the theme of activity the first user may be performing, may be determined. At step 1324, if the virtual content does not match the theme of activity which the user may be performing, then the processor may request additional information from the user. Based on the received additional information, the processor may, at step 1326, render virtual content using the user provided information suitable to the theme of activity. At step 1322, if the virtual content matches the theme of the activity, then at step 1328, the processor may render virtual images of one or more other participants whom the user wishes to be participants in the activity. The selection of other participants in the activity may also be based on the user's profile information. The processor may be configured to execute step 1328 after step 1326. The virtual images of one or more of the user's friends or family members whom the user may be willing to participate with depends on the information corresponding to the user's profile. For example, the user may wish to perform yoga with his family members. The processor may receive this information from the user and subsequently may provide or render the virtual images of one or more family members of the user. At step 1330, whether the virtual images correspond to the participants whom the user may be willing to participate with, may be determined. If the virtual images do not correspond to the participants whom the user may be willing to participate with, then the processor, at step 1332, may request for input from the user to modify or alter the content based on the input provided by the user. At step 1334, the processor may render modified virtual content based on the input received from the user. If the virtual figures correspond to the users whom the user may be willing to participate with, then, at step 1336, the processor may enable the user to perform the desired activity and interact with one or more participants during the activity. Further, the processor may also be configured to render images of other participants, who may not engage in the activity. The processor may only display images of participants who may not engage in the activity. The processor may be configured to execute step 1336 after step 1334.

In an embodiment, the content that may form the scenery may be displayed on one or more display interfaces. Such content may be in two or three dimensional format based on one or more factors, such as, the type of content, type of display interface and user's preference among others. The display interfaces may be, for example, a wall, floor and ceiling among others. The AR device may be configured to project the rendered images onto the display interface.

The system may be configured to render virtual content, showing the virtual presence of one or more participants to a user while the user is at home preparing for a yoga session. The user may be wearing his/her AR device. The system may render virtual content displaying the virtual images of one or more participants whom the user may or may not know in person. The system may also allow the one or more participants to communicate with the user through the communication module 1202 during the session through voice or through texts or both voice and text. The system may render the virtual content such that the user may experience an environment where the user is performing yoga with the plurality of other participants. The system may also render the virtual image of an instructor whom the user may or may not know in person. The system may further render suitable background scenery of a meadow or a meditation hall, among other backgrounds.

The system may be implemented in a scenario to replace business travel by virtual teleconferences where participants may experience the feeling of physically being present at the location, interacting with their co-workers or clients, even though they may not be physically present at the location. The participants who may be wearing the VR devices may be provided access to other participants who may be participating in the conference virtually. However, the participants participating virtually may be able to see all the participants, who are physically present at the conference and who are virtually participating in the conference. Similarly, the participants, who are physically present at the conference, may be able to see all the virtual participants. This can be enabled by providing a video camera at the conference, which may record the events at the conference as well as images and videos of the participants of the conference. One or more of the participants may be enabled to take control of the session. The participant(s) who may be taking control of the session may be able to initiate the session and allow other participants to provide data to be displayed as virtual content, while the session is in progress. The data provided by the participants may be data related to the teleconference.

The system may be implemented in a scenario where the user may be willing to dine at home as well as feel the presence of one or more of his friends or family members beside him. The processor may render virtual content by receiving input from the user. The processor displays the background as the scenery of a restaurant. The virtual content representing the scenery of a restaurant may be displayed to the user. The user may be enabled to select one or more friends and family members whose presence the user wishes to feel or whom the user wishes to have as participants while dining. The processor may render the virtual images of those people selected by the user. The processor may render the virtual image of his/her friends on a display interface such as holographic display interface. The user may be enabled to communicate with his friends while dining, through the communication module 1202.

In an embodiment, and referring to the above examples, the processor may, retrieve from the database 308, information corresponding to the user's social networking profile and the user's relationship information with other users on the social networking platform. The profiles of one or more users with whom the user may be connected on the social networking platform may be retrieved and stored in the database 308. The processor may generate the virtual content based on the information retrieved. The processor may further instruct the VR device to display virtual models of one or more of the user's friends whose profiles may be stored in the database 308.

Alternatively or additionally, the system may be configured to receive inputs from the user wherein the input may include information corresponding to the user. Such information may include a user's name, place of work, contact details, home address, list of friends of the user and their contact information, hobbies, activities the user may be involved in and recent activities the user was engaged in and daily activity schedule, among other information. Such information can also be fed to the system 100 by the user, such as, for example, by filling a questionnaire and may be stored in the database 308. The user may also provide information corresponding to his/her friends and family members such as, place of work, hobbies, activities they may like doing and recent activities they were engaged in and daily activity schedule among other such information.

In an embodiment, the processor may be configured to understand the user's interest, preferences and priorities among others based on the information corresponding to the user's profile. The processor may also be configured to learn what activity the user may be performing at a particular time of the day, or on any particular day, based on the user's daily activities and previous activities. Such information may be stored in the database 308 and retrieved from the same whenever necessary. Based on the learning, the processor may generate the virtual content by retrieving the user's profile information from the database 308.

The system can include a selectively controllable front transmission and reflection unit to converted between AR and VR, or variations in between for a rich visual environment. To provide full 360 degree view, the embodiment also provides a rear view mirror on both sides of the eye to provide complete selectivity of rear view. Multiple layers can be used in a multi-layered structure making up an exemplary window that can turn off the outside view for VR in the reflection mode, or can allow view of the outside world for AR in the transmission mode. In this structure, the electrically active optical layer is a nematic liquid crystal thin film of about 4 to 25 microns in thickness. The nematic liquid crystal materials (commonly used for thin film transistor driven liquid crystal displays and readily purchased from companies such as Merck KGaA of Germany or Chisso Corporation of Japan) can be used as an electrically active optical layer in this structure. The electrically active optical layer 100 is aligned by treated surface layers 101 which can be rubbed polyimides such as SE610 from Nissan Chemicals. The electrical stimulus is applied to the electrically active optical layer 100 via optically transparent, conductive Indium Tin Oxide (ITO) layers 102, which are directly deposited on substrates 103. Such a standard glass substrate is the ITO coated Corning 1737F borosilicate glass from Corning, Inc. The ITO layer 102 may cover the entire substrate 103, or may be pixellated so that different regions of the window structure may be controlled in opacity and reflectance independently. A desirable substrate in some instances could be an ITO coated plastic substrate that is flexible, where the assembled window structure will be able to assume curved shapes.

The next layer in one direction is an absorptive polarizer. The next layer in the other direction is a reflective polarizer 104. Absorptive polarizer 105B can be pre-assembled to reflective polarizer such that the polarized light transmission direction of the reflective polarizer 104 is parallel to that of the absorptive polarizer. If the reflective polarizer is linear, it reflects one polarization while transmits the orthogonal polarization of light incident on it. On the other hand, the absorptive polarizer 105, if linear, absorbs one polarization while transmitting the orthogonal polarization of light incident on it. Absorptive polarizers with pressure sensitive adhesive layers are available from companies such as Sanritz Corporation of Japan. Alternatively, polarizers preassembled with a compensation film, such as those wide viewing angle absorptive polarizers. The next layers are transparent polymer layers where the layers serve multiple purposes including shock absorption, UV blocking, index matching, and anti-glass shattering. A common polymer layer is that of polyvinyl butyrate from Solutia, Inc. The next layers are protective substrates 107, where glass used for conventional window glass can be used and is laminated on the interior structures 106 through 100 using either a pressure treatment process or heat curing process, depending on adhesive films used in the stack. Alternatively, treated glass, such as those from DENGLAS Technologies, LLC, offers advantages of increased transmission, reflection, and anti-glare when used as protective substrates 107, where the glass substrates are coated with broadband antireflection coatings. Yet another alternative is to laminate antireflection polymer films 108, such as those from Toppan Printing Co. Ltd of Japan, on uncoated glass of 106 to reduce glare and to increase transmission of the window stack. Furthermore, UV absorbing or rejecting film 109, such as the Llumar series from CPFilms, Inc. is laminated on the stack to reduce the amount of UV from ambient or from Sunlight to enter into the building and to reduce potential damage to the electrically active optical layer 100 or other polymer based components in the window structure.

According to one of the above embodiments, the present invention may generally include a view mirror assembly with a variable reflectance mirror element and a projector, display electronic device positioned behind the mirror element so as to transmit or receive light through the mirror element. Unlike prior rearview variable reflectance mirror elements, however, the mirror element may utilize a polarized reflector that transmits light having a first polarization, while reflecting light having a second polarization opposite the first polarization. The electronic device emits light or receives light having the first polarization such that the light passes very efficiently through the mirror element with almost no loss. Approximately half of the ambient light, on the other hand, is reflected so that the mirror element acts as an effective rearview mirror. The polarized reflector may function as one of the electrodes of the variable reflectance mirror element.

The reflective polarizer may be a "wire grid" type of polarizer that reflects (specularly) one plane of light polarization and transmits the other. A display or other light source that emits polarized light would not suffer a large drop in brightness if it is oriented such that its polarized light is transmitted through the mirror element and not reflected. If a light source or light emitting display that does not emit polarized light is used behind a "wire polarizer" mirror element, a portion of the light is transmitted and a portion of the light is reflected. Both the transmitted and reflected light is polarized. The polarized reflected light could be de-polarized by reflective scattering and part of that light will then be transmitted by the mirror element or the plane of polarization of the light could be rotated 90 degrees and reflected back through the "wire grid" polarizer. This will enhance the display brightness. Similar techniques could be used to utilize ambient light that is transmitted through the wire grid polarizer into the display/reflector assembly.

If a TFT LCD is used as a video display, and the display is oriented such that its polarized light is transmitted by the wire grid polarizer, almost 100 percent of the light it emits is transmitted and almost 50 percent of ambient light is specularly reflected by the mirror. The result is a high brightness "display on demand" mirror where almost no display brightness is lost yet the "mirror" is near 50 percent reflective to ambient light.

This "wire grid" polarizer/mirror and display assembly could be used "as is" in a non-dimming rearview mirror assembly or it could be laminated to or attached to an electro-optic dimming window (LCD or electrochromic element) to make a dimming "wire grid" polarizer/mirror and display assembly with variable reflectance. One advantage of using such an electro-optic element in front of the reflective polarizer is that the electro-optic element may be made less transmissive when the display is turned on. The ambient light striking the mirror element passes through the electro-optic element twice while the light from the display or light source only passes through once. Thus, by dimming the electro-optic element when the display is on, twice as much of the ambient light is absorbed as the light from the display or light source thereby increasing the relative contrast ratio of the display during high brightness ambient conditions.

A typical "wire grid" polarizer available from Moxtek (ProFlux™ type) is made by coating glass with a reflective aluminum layer. This aluminum layer is then patterned into straight lines and spaces using typical semiconductor patterning technology. The beginning of line to beginning of line spacing is about 0.15 microns (150 nm). The aluminum line width and spacing width can vary, but looks to be about a 60 AC/40 size ratio by SEM analysis. The ratio of the metallic line width to space width can be varied to change the ratio of reflection to transmission. Such an assembly could be used as an electrode in an electro-optic element such as an electrochromic device or an LCD device. For example, if a silver or silver alloy film is patterned in such a way, it could be used as a third surface reflector electrode in an electrochromic mirror element. The metal grid layer could be overcoated or undercoated with a transparent conductor, such as ITO, ZnO, or tin oxide to enhance conductivity or electrode stability. The wire grid layer could also be overcoated or undercoated with a thin layer of reflective material such as silver, silver/gold, gold, aluminum, or other reflective metal or metal alloy to enhance reflectivity. The reflectivity could also be enhanced by an overcoat or undercoat of a dichroic film stack or enhanced by such typical means of increasing the reflectivity of silver or aluminum films. In this way, a dimming mirror assembly can be made that will support a high brightness, high resolution display assembly.

Other methods used to reflect light of one type of polarization (circular or linear) and transmit light of the second type of polarization are known that may be used as the polarized reflector of a variable reflectivity mirror. A laminated foil made of multiple layers of plastic film wherein some or all of the films layers have an internal molecular orientation (induced by stretching or other means) that induces a directional difference in refractive index can be constructed such that the laminated foil reflects one type of polarization and transmits the second type of polarization.

Cholesteric polarizers can also be made that will reflect one type of polarization and transmit the second type of polarization, and thus serve as the polarized reflector for a variable reflectivity mirror. These polarizers can be made such that they are voltage switchable. In other words, these polarizers can be switched from reflecting the first type of polarization and transmitting the second type of polarization to transmitting both types of polarization or they can be switched from reflecting the second type of polarization and transmitting the first type of polarization to transmitting both types of polarization. The wavelength of light that is reflected by these cholesteric polarizers is dependant on the pitch of the twist in the cholesteric structure. A single pitch cholesteric structure reflects a fairly narrow (<100 nm) bandwidth of light. A variable pitch cholesteric structure reflects a wider bandwidth of light. The greater the variation in cholesteric pitch, the wider the bandwidth of light that is reflected. Such a variable pitch cholesteric structure is described in U.S. Pat. Nos. 5,762,823 and 5,798,057, the entire disclosures of which are incorporated herein by reference.

One or two of these switchable variable pitch cholesteric polarizers can be used in combination with a light emitting display device to construct a variable reflectance rearview mirror with enhanced display viewability. One switchable variable pitch cholesteric polarizer in combination with a typical TFT LCD assembly can be configured to either reflect one type of polarization and transmit the second type of polarization that the TFT LCD emits or transmit both types of polarization. This construct enables four modes of operation: 1) mirror at ~50% reflection, display off; 2) mirror at ~50% reflection, display on; 3) mirror at ~0% reflection, display on; and 4) mirror at ~0% reflection, display off (note: the reflectance of the mirror assembly in this configuration would approximately be the magnitude of reflection off of the first substrates surface or about 4%).

Two switchable variable pitch cholesteric polarizers used in combination with a typical TFT LCD add one additional high reflectance mirror mode to the above. In the high reflectance mode, the first switchable reflective polarizer would reflect one type of polarization and transmit the second and the second switchable reflective polarizer would reflect the second type of polarization. In the mid reflectance mode, one reflective polarizer would reflect one type of polarization and transmit the second type of polarization which is the same polarization of light the TFT LCD emits. In the low reflectance mode, both switchable reflective polarizers would transmit both types of polarization. This construction enables five modes of operation: 1) mirror at ~100% reflection; 2) mirror at ~50% reflection, display off; 3) mirror at ~50% reflection, display on; 4) mirror at first surface reflection (~4%), display off; and 5) mirror at first surface reflection (~4%), display on. Additional reflectance states may be obtained when using one or more switchable variable pitch cholesteric reflective polarizers in combination with an electrochromic element positioned between the viewer and the polarizer(s). If additional levels of reflectivity are desired, an electrochromic element may be disposed in front of the cholesteric element(s), or the cholesteric element(s) may be used alone to a two- or three-state variable reflectivity mirror.

As described further below, switchable variable pitch cholesteric reflective polarizers can also be used in vehicle windows, sunroofs, architectural windows, and skylights.

Another embodiment of the present invention is based on the recognition by the inventors that displays (particularly TFT LCD displays) emit light from well-defined relatively small light emitting areas constituting only about 30 percent of the total surface area of the display. According to this embodiment, very small holes or slits are created in a highly reflective coating and are aligned with the pattern of light emitting areas from the display. Each pixel has a hole positioned to allow light to pass with little attenuation toward the driver of defined user location. By creating holes of the correct size aligned with the emitting areas of the display, an average reflection percentage of 60% or higher can be achieved and still have very little attenuation at the points of transmission. This concept can be enhanced in several ways. First the holes need not be round with uniform edges. Holes with complex edges can be made less visible. The hole regions can be made transflective to further disguise the hole. This sacrifices some transmission efficiency for better reflector appearance. It is desirable to disguise the display region such that the display is more of an "on demand" display. This can be further enhanced by employing the hole pattern over the entire mirror area. It can be further enhanced by matching the reflection of the basic display regions in the regions not backed up by the display.

Further, there is another form allowing a very high reflection percentage and no attenuation of the display. This can be achieved by using a shutter action. The display top surface may carry a high reflection surface matching that of the mirror. When aligned (shutter open), holes in the display reflecting surface align with holes in the mirror reflecting surface and the display becomes visible. If the display is displaced, the holes in the mirror align with the reflecting surface of the display. This yields a 100% reflecting area. Since the reflecting surfaces can be in direct contact, the only optical distortion is due to the thickness of the mirror reflecting layer causing very small ridges around the holes. The resulting optical distortions are virtually invisible for viewing angles of use in rearview mirrors.

The shutter movement can be made using ceramic piezoelectric transducers. Movement can include a component to separate the surfaces as part of allowing the display to shine through. This would avoid any surface damage due to shutter movement.

The concept of aligning apertures through the reflector with the areas of display emission meets the challenge of creating a highly reflecting surface and having a high degree of display transmission because it separates the surface requirements. It has the effect of impacting only the display aperture regions. Thus the vast majority of the surface functions as well as a conventional reflector. As a result, means can be used in the aperture areas to switch between reflector and transmission that would not be suitable if applied over the entire area. This approach is inherently very robust as a failure only impacts the display holes not the primary reflecting surface.

By placing an optical device between the display and the mirror surface, light from the display can be converged so more light can be passed through a smaller aperture. The light converges to a very small diameter then diverges at the same angle. If the point of convergence to a smaller diameter is approximately aligned with the holes in the reflecting coating a much larger field of view may be achieved using smaller aperture holes and a greater spacing between the display and the mirror surface. This would be more practical when the reflector is provided on the third surface of the mirror element.

An appropriate optical device would be a plastic sheet with molded lens details for every pixel. Light from the display radiates to the lens where it is converged, through the reflecting layer hole and then diverges at the same angle as the convergence. To the viewer the display regions seem larger and the display can be seen from angles greater than could be achieved if the optical device were removed.

This sheet like optical element can be made by the same processes as those currently used to make lenticular lens sheets for auto-stereoscopic displays only in this case the lenses would be spherical. It should be noted an auto-stereoscopic display through a reflecting surface can also be made using this same basic idea only the hole patterns in the reflecting layer would be formed as narrow vertical slits.

The system includes a method of receiving information corresponding to the user and generating virtual content based on the information corresponding to the user retrieved from the database 308, in accordance with an embodiment. At step 1502, the processor may communicate with one or more servers 1204 to retrieve information corresponding to the user and other participants the user may be connected with on one or more platforms. The platforms may be for example, social networking platforms. At step 1504, the processor may further receive information corresponding to the user and other participants the user may be connected with on one or more platforms provided by the user. The user may provide such information manually through a user interface that may be associated with the system. At step 1506, the database 308 may store the information corresponding to the user retrieved from different servers 1204 and the information provided by the user. Information provided by the user may include information corresponding to one or more users the user may know or may be willing to participate with, in an activity. At step 1508, the processor may learn from the user's profile information retrieved from the servers 1204, the user's interest, preferences and priorities. At step 1510, whether the information retrieved from the servers 1204 is sufficient to generate the virtual content, may be determined. If the information from the servers 1204 is not sufficient, the processor, at step 1512, may access the information stored in the database 308, which may be provided by the user. If the information from the servers 1204 is sufficient to generate the virtual content, then, at step 1514, the processor 102 may generate virtual content to be rendered and displayed to the user based on the information retrieved. Also step 1514 may be executed after step 1512.

In an embodiment, the processor may instruct the VR device to display a list showing the names or profiles of one or more users whom the user might have interacted with on one or more platforms earlier. Such profiles may be stored in the database 308. The user may be provided an option to select one or more users to participate in an activity with from the displayed list. Such a list may be generated by the processor by accessing the database 308. The processor may instruct the VR device to provide virtual images of one or more of the users whose names and profile information may be displayed on the list. The processor may render the virtual content and communicate it to the VR device for display.

The processor through the communication module 1202 may further be configured to notify the participants, whose profiles have been selected by the user, about the user's interest in participating in the activity with them. One or more of the participants to whom the notification may have been communicated, may show interest in joining the user in the activity. The processor may accept response from one or more participants who may show interest in joining the user in the activity. The processor may render the virtual content displaying the presence of the participants who may have responded showing interest in joining the user. The virtual content may be videos of the other users. The user may be enabled to communicate or interact with the other users through the communication module 1204. The image capturing device of the system may capture images of the user and communicate it to the other users. Similarly, the respective image capturing devices of the systems 300 of the other users may capture the image and voice of the other users and communicate it to the user.

In yet another embodiment, the user may be enabled to send requests to one or more participants, whom the user may be acquainted with, to join the user during the yoga session. The other participants may accept or decline the request. The processor may display the virtual presence of the participants who may have accepted the user's request. The virtual content may be videos of the other users. The user may be enabled to communicate with the other participants through voice data. Alternatively, the user may be able to send requests to one or more users whom the user may be connected with on a social networking platform. The image capturing device of the system 100 may capture images of the user and communicate it to the other users. Similarly, the respective image capturing devices of the systems 100 of the other users may capture the image and voice of the other users and communicate it to the user. The other users may replicate the actions performed by the user.

The system can render virtual content based on the user's selection of participants in the activity, in accordance with an embodiment. At step 1516, the processor may instruct the VR device to display a list to the user, displaying the names or profiles of one or more participants, whom the user might have interacted with on one or more platforms earlier, to join the user in an activity. At step 1518, the processor, may enable the user to select from the list of users, one or more participants the user may be interested to participate with. At step 1520, the processor may notify the participants, whose profiles have been selected by the user. At step 1522, the processor may further enable the user to send requests to one or more participants, whom the user may be acquainted with, to join the user in an activity. It may be noted that the steps 1516 and 1522 can be optional and may be executed individually in two different scenarios. At step 1524, the processor may accept response from one or more participants who may show interest in joining the user in the activity. At step 1526, the processor may render the virtual content displaying the presence of the participants who may have responded showing interest in joining the user in the activity.

In another embodiment, the processor may be configured to render virtual content displaying virtual presence of one or more participants whom the user may be willing to participate with, based on preconfigured or configurable set of rules incorporated in the processor. The processor may learn from the user's previous interactions and types of activities and thereby determine, whom the user may be willing to participate with for one particular activity. For example, the user may have participated in yoga sessions with users A, B and C on one particular day and with users B, D and G on a second day. On a third day, the processor may render virtual content wherein the virtual content may display virtual model of user B and allow the user to select other users in addition to user B to perform yoga.

The system includes a method of rendering virtual content based on machine learning algorithm incorporated in the processor, in accordance with an embodiment. At step 1528, the machine learning algorithm incorporated in the processor may be configured to learn from activities that had been performed earlier by the user. At step 1530, the processor may determine the type of content that has to be rendered based on the learning. At step 1532, the processor may render at least a portion of the virtual content based on the learning. Such content may include images of one or more participants whom the user may have performed an activity with earlier. At step 1534, the processor may determine whether the portion of the virtual content displayed corresponds to a particular activity. For example, the processor may determine whether the model of the user rendered, corresponds to the participant who might have performed the activity with the user earlier. If the portion of the virtual content displayed does not correspond to the particular activity, then, at step 1536, the processor may request for additional information from user. At step 1538, the processor may render virtual content using the user provided information that may correspond to the activity. If the portion of the virtual content displayed corresponds to the particular activity, then, at step 1540, the processor may provide an option to the user to modify the content. Modifying the content may include adding more participants to the content, removing participants from the content and changing the type of activity, among others. If the user wishes to modify the content, then at step 1542, the processor may receive input from the user to modify or alter the content. At step 1544, the processor 102 may render modified virtual content based on the input received from the user. If the user does not wish to modify the content, then at step 1546, the processor may enable the user to perform the activity and communicate with the one or more users during the activity.

The processor may render virtual content to the user, displaying videos of the participants the user might be willing to participate with. The video data may be integrated with voice data. Alternatively, the processor may generate virtual two or three dimensional models of the participants the user might be willing to participate with. The virtual two or three dimensional models of the participants may be integrated with voice data. Further, the processor may be able to render pre recorded voice data to the virtual two or three dimensional models. The user may be able to communicate with the virtual content displaying presence of the participants the user might be willing to participate with, through voice and text.

The system may be integrated with one or more social networking servers 1204 such as Facebook. The system may enable the users to log in to the social networking portal. The user's profile may be connected or related with a plurality of other users on the portal. The user may be provided an option to communicate with one or more of the plurality of users who may be available or online as seen on the page of the social networking portal. The user may be provided an option to participate with a plurality of users whom the user may prefer to communicate with. Virtual models of one or more of the plurality of users may be rendered and displayed to the user for communication. The communication may happen in the form of voice or text.

In an embodiment, the processor may render virtual two or three dimensional models of random users/people that the user may not know in person. Such random profiles of users whom the user may or may not know in person may be preconfigured by the processor by receiving input from the user. Further, such profiles may be preconfigured profiles of other users by the processor may be created by applying intelligence based on the user's preference, interest and priorities, among others. These preconfigured profiles of random people may be stored in the database 308. Examples of random models may include models of celebrities or animated characters, among other profiles. The processor may be configured to voice attributes among other such attributes to such models. Such random virtual three dimensional models of random participants may be rendered when the user may not be willing to communicate with the users who may be connected with the user or such users may not be available to communicate at that instant.

In one embodiment, for the system to enable the users to participate in an activity and communicate with the user in virtual reality, it may be required that all the other users wear their respective VR devices.

Input such as, tactile and gesture input, data indicating pressure and force vectors, applied through the user's limbs, among others may be received through one or more sensors included in the system. The processor may be configured to synthesize the input and determine the visual output or outcome based on the input. The outcome may be applied to the virtual images to alter one or more parameters (location, size etc) of the objects in the virtual images. Gestures along with the semantics of each gesture received through the sensors may be stored in the database 308. The semantics of the gestures may be predefined and stored in the database 308. The database 308 may also store outcomes of such input. The outcomes may indicate one or more physical actions carried by the user which may be applied to the virtual content to modify or alter parameters of the content.

Virtual content may be displayed to the user to provide the user with the experience of physically shopping at a location, though the user is indulging in virtual shopping. The system may be able to communicate with one or more remote servers 1204 via the communication module 1202. The servers 1204 may be associated with one or more service providers such as, store websites, online shopping websites and super markets among other service providers. Input may be accepted from the users, through a user interface. The user interface may be portals pertaining to the service providers. Input may include requests to view a shopping location, having at least one store, and displaying the shopping location to the user via the virtual interface of the system. The input may be in the form of URLs provided through a virtual browser that may identify a particular service provider's website. The system may provide users with experience of walking beside aisles of the stores, entering the store by opening and walking through its doors, examining the items on the shelves, and placing them into the shopping cart. The gesture of picking up an item and placing it in the shopping cart may be perceived as placing an item in the shopping cart.

The virtual content may be preconfigured or configurable by the service providers. The processor may access the servers 1204 associated with the plurality of service providers and render and display the virtual content to the users. The content may be customized for each user and the customization may be based on the user's profile. The user's profile may include information corresponding to the user's history of purchase, age, gender, location of the user and the user's preferences, among others. The user may create a profile on the portals of the service providers. Alternatively, the servers associated with the service providers may be able to retrieve such information from one or more servers 1204 associated with one or more platforms where the user may have already created a profile. Further, the servers associated with the service providers may be able to retrieve such information corresponding to the user from the processor.

In an embodiment, if the user is virtually shopping at a store, the user may request to interact with one or more of the store's shopping assistant while purchasing. The users may post queries and the shopping assistant, who may provide answers to the queries. In addition, the virtual content that may be presented to the users by the service providers may enable the users to learn about the store, its brands, or any other information the store may wish to covey to the user. Further, the users may be able to provide feedback based on their experience.

Alternatively, the users may be assisted by virtual shopping assistants at one or more sections while purchasing. For example, when the user may not be able to decide between two similar items and spends more time browsing at one particular section without placing any item into the shopping cart, the shopping assistant's virtual model may be displayed to the user to assist the user in the purchase. The store keeper may provide reviews and feedbacks of other customers to the user and help the user make the purchase.

In another embodiment, virtual assistance may be rendered into virtual reality by means of one or more among text and voice as opposed to virtual models of shopping assistants providing assistance.

In an embodiment, virtual content for an online shopping website may be pre configured or configurable by the service provider. The processor may access the servers associated with a plurality of service providers and render and display the virtual content to the users. The user may request for the shopping assistant to assist him/her with the purchase. For example, if the user is shopping for apparels, he/she may request virtual assistance from a stylist or may request for the specifications of the product. If the user is purchasing a book, the user may scan through the cover and request for reviews. Reviews provided by other users may be displayed in virtual reality. Virtual assistance may also be rendered into virtual reality by means of one or more among text and voice as opposed to virtual models of random people.

In an embodiment, all information corresponding to a particular product may be rendered and displayed as soon as the user selects the product or places it into the shopping cart, in virtual reality. Information may include all reviews provided by users from across the world, specification of a particular product and a comparison chart between two or more similar products among others may be rendered to the user in virtual reality. Such information may appear as texts. Such information may be presented by random models of users who may have purchased the product earlier or who may be associated with the product through audio output. Further such information may be presented as one or more among texts and voices.

In an embodiment, virtual assistance may be provided to the user based on the user's profile and purchase history, among others. Alternatively, the users may be provided with options to select assistance whenever the user might require assistance.

Figure 16A:
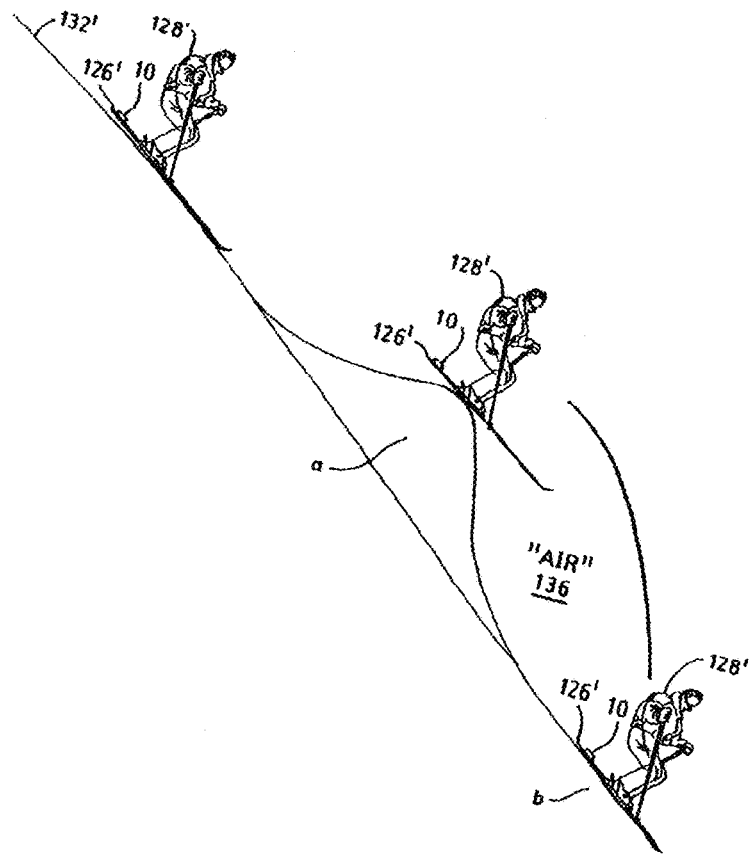
Figure 16B:
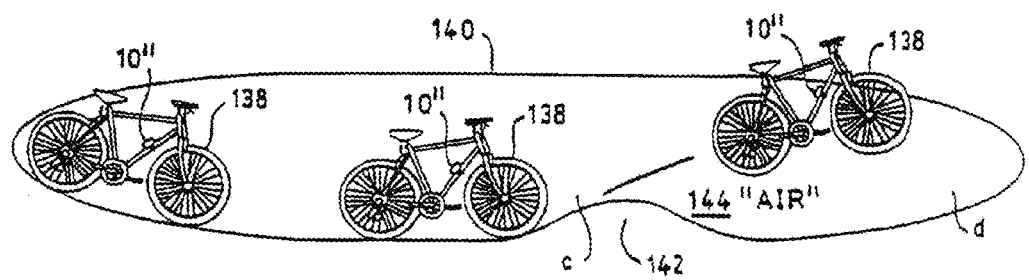
Figure 16C:
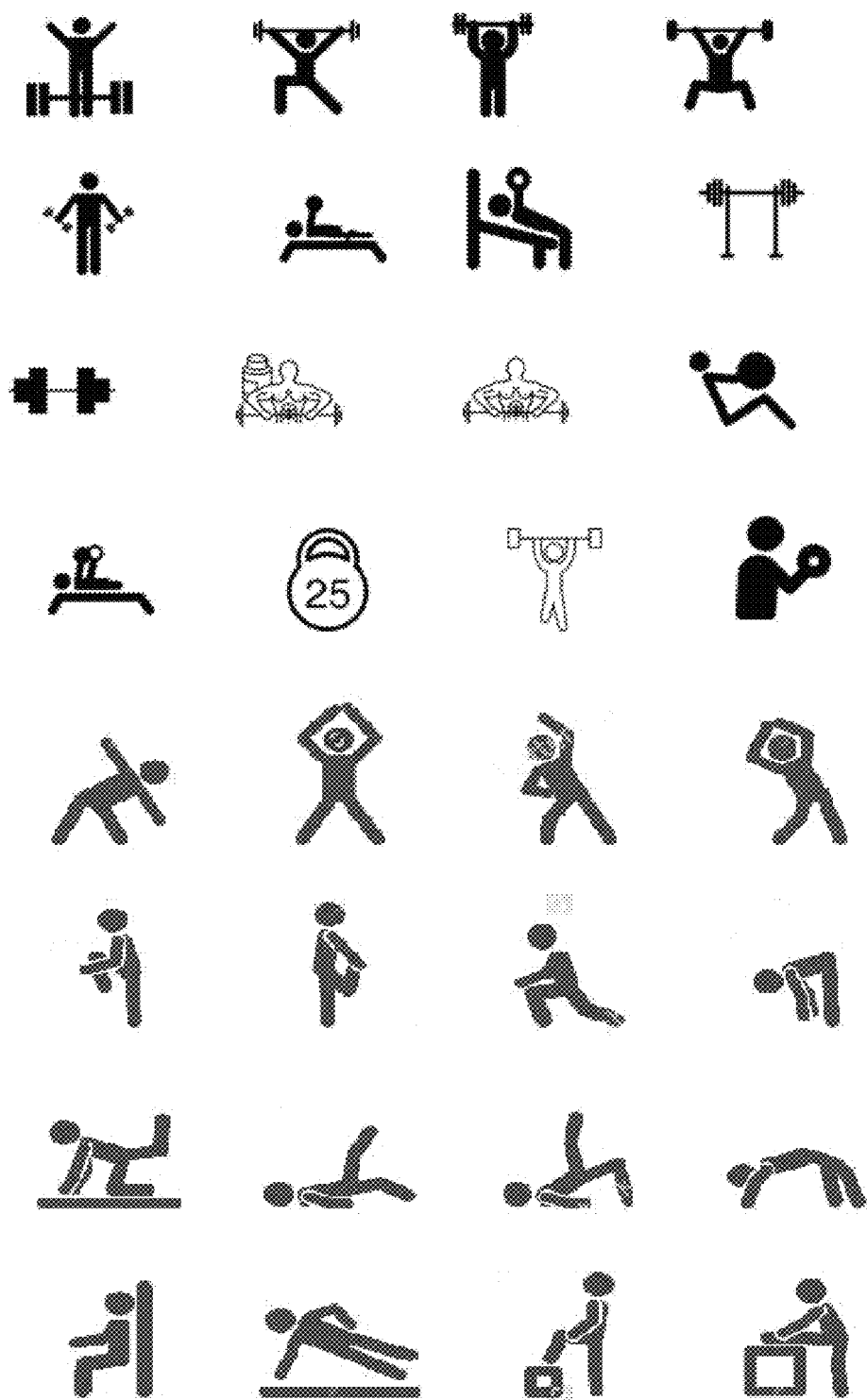

FIG. 16C is a flowchart illustrating the method of rendering virtual content to the user to enable the user to shop online or at stores, in accordance with an embodiment. At step 1602, the processor may communicate with one or more remote servers to retrieve information corresponding to one or more service providers. At step 1604, the processor may allow the user to provide input requesting to view a service provider's portal/webpage. At step 1606, the processor may render virtual content displaying a service provider's webpage. At step 1608, the processor may allow the user to browse through different sections of the service provider's webpage. At step 1610, the processor may determine if the user has requested for assistance to make a purchase. If the user has not requested assistance, then the processor, at step 1612, determines whether the user has selected any product. If the processor determines that the user has requested for assistance to make a purchase, then at step 1614 the processor may render virtual content presenting virtual assistance to the user. After step 1614 has been executed, the processor may execute step 1612 again until the processor determines that the user has made a selection at step 1612. If the processor determines that the user has made a selection, then, the processor, at step 1616 may render virtual content including information corresponding to all or a portion of the products the user has selected.

In an embodiment, the user may be provided an option to proceed with payment after making selection. The user may also be assisted during the payment. Virtual assistance may be provided to the user to select a payment method and accordingly proceed with the steps of payment. Such virtual assistance may be in the form of voice or text or virtual models may be presented to assist the user.

In another embodiment, the system may be integrated with an application module that may be implemented for the purpose of enabling the user to shop online or at physical stores virtually in a two or three dimensional virtual reality interface. The user may be required to log into the application module and browse for shops or products or categories of products through the virtual interface.

In some embodiments, one or more of users participating in the activities in all the above examples may have cameras or any image or video capturing devices integrated with their respective VR devices. Images, photos, videos or live webcam feeds of the users may be communicated to the other users whom they are participating and communicating with.

In an embodiment, the users may communicate with one another in virtual reality via voice communication modules. The users may also communicate with other users using voice data through a telephone module. The users may be enabled to provide voice data through a microphone and receive voice data from other users through headphones or speakers.

In an embodiment, the rendering module 304 may render enlarged lifesize views of three-dimensional content on display surfaces such as walls, floor, ceiling and table surfaces among others.

In an embodiment, live feeds from one or more servers 1204 may be received and processed by the processor in near real time to generate the virtual content.

The system can be used in industrial applications, for example in repair/maintenance augmentation. One exemplary pseudo-code is Repair Augmentation
User selects AR assisted repair mode,
System identifies surface and components mounted thereon
System looks up repair sequence:
determines type of component, location of component,
identifies or highlights on the HUD each component to be opened or removed and provides instructions on removal techniques,
wait until each component is opened or removed and then show next component until done
accesses the target component to replace or repair and show instructions to repair or replace,
sequentially shows instructions to put back components previously opened or removed.

In another implementation, objects may be presented to the illumination and sensors so that their content may be analyzed and their placement on the repair surface may be determined by the computing system. The computing system may then supply augmented reality data streams to the AR interface users to inform them of the composition of each of the sortable objects.

In one embodiment for sorting a stream of small objects, a sorting machine can have a number of lanes on a moving sorting surface, each lane containing objects having the same composition. For example, as the sorting surface moves between a group of sorters, the sorters may simply push the objects into a specific lane based on composition. The AR system can color code each object to be sorted into a particular lane. At the end of the moving surface, a sorter may have pre-arranged bins placed to receive the objects from each lane as they fall off the surface into the appropriate bin. The AR system can provide sensors such as spectral sensors for a majority determination of composition. In the event that an object does not have a consistent spectral response, information may be presented over the AR interface to a sorter, letting him or her know that the object should be set aside for further consideration. The computing system may provide a group of sorters, using augmented reality interfaces, with information regarding how to bin each object. The sorters may continue to place objects by composition into appropriate bins until the bins become full. In one configuration, a sorter may then stop sorting and move the bin to a shipping location. During the time the sorter is away from his or her position by the sorting surface, the sorter may notify a facility operator of this break in the sorting process over a voice transmitting channel associated with the AR interface. Alternatively, another facility worker may move the bin to a post-processing station (such as a station to box the items for shipping to another facility). If the post-processing station becomes overburdened due to a large amount of material to ship out, the post-processing worker may notify the facility operator over an AR interface voice channel that the sorting process for that particular material should be delayed. In either alternative, the facility operator may then direct the computing system to slow the travel of the moving sorting surface or even stop it entirely. In this manner, the sorting process may be adapted to changes in the work flow.

Figure 14:
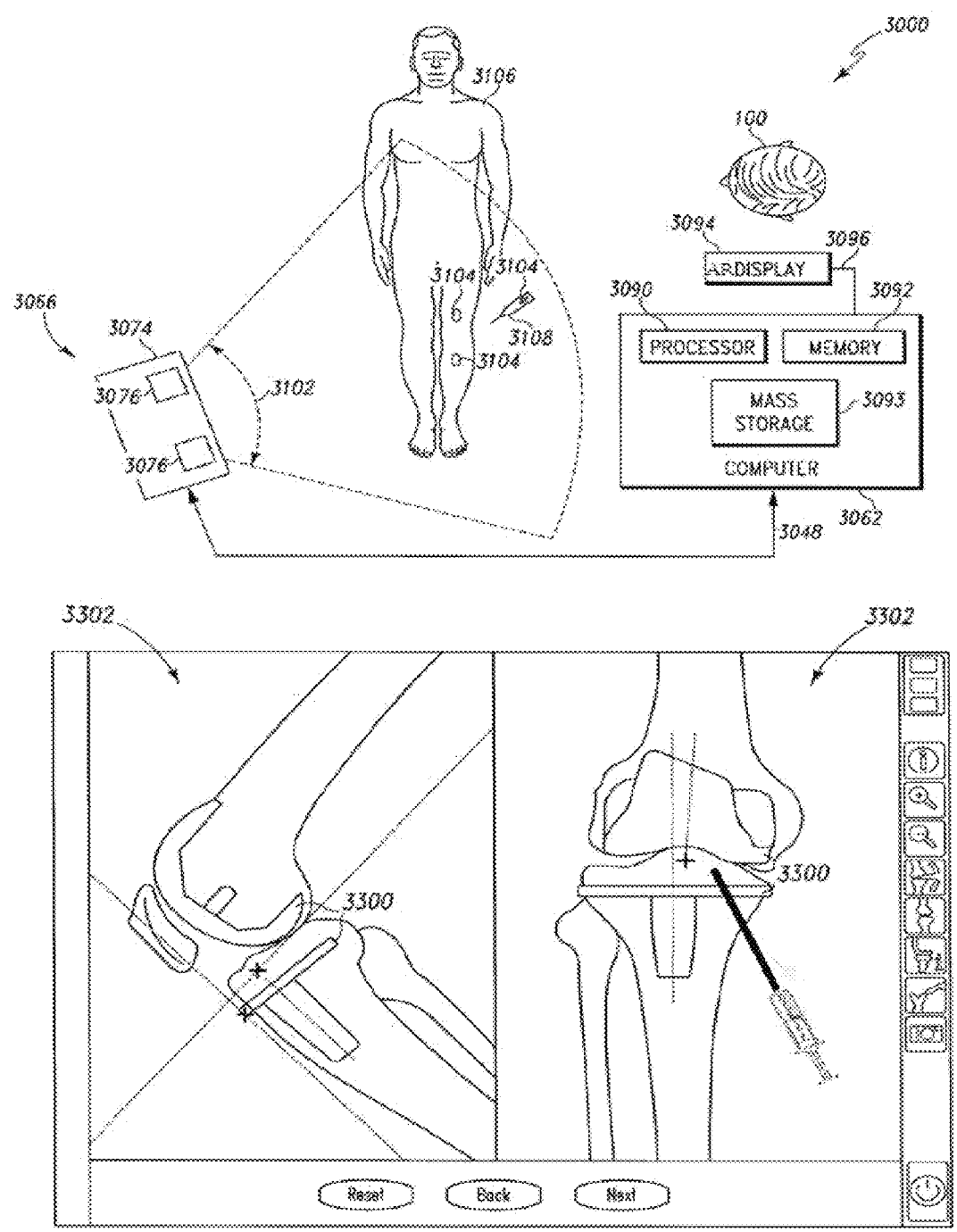
FIG. 14 shows an exemplary AR surgical system.

FIG. 14 shows an exemplary AR surgical system. The system may include a processor 3090, a memory device 3092, and mass storage device 3093. The computing device is communicatively coupled with a display device 3094. The AR display device 3094 may be a body mounted display such as a heads-up display or a glass mounted in an AR system such as that of FIG. 1, or an additional display device may be positioned away from the computing device. For example, the display device 3094 may be positioned upon the ceiling or wall of the operating room wherein the orthopaedic surgical procedure is to be performed. Additionally or alternatively, the display device 3094 may include a virtual display such as a holographic display and/or other types of displays. The computing device may be communicatively coupled to one or more camera units. The system0 may also include sensors or reference arrays 3104 which may be coupled to relevant bones of a patient 3106 and/or with orthopaedic surgical tools 3108. For example, a tibial array can be used that includes a reference array and bone clamp. The bone clamp may be coupled with a tibia bone of the patient using a Schantz pin, but other types of bone clamps may be used. The reference array may be coupled with the bone clamp via an extension arm. The reference array may include a frame and three reflective elements. The reflective elements in one embodiment are spherical, but may have other geometric shapes. Additionally, in other embodiments sensor arrays having more than three reflective elements may be used. The reflective elements may be positioned in a predefined configuration that enables the computing device to determine the identity of the tibial array based on the configuration. That is, when the tibial array is positioned in a field of view of the camera head, the computing device may determine the identity of the tibial array based on the images received from the camera head. Additionally, based on the relative position of the reflective elements, the computing device may determine the location and orientation of the tibial array and, accordingly, the tibia to which the array is coupled.

Reference arrays may also be coupled to other surgical tools. For example, a registration tool may be used to register points of a bone. The registration tool may include a sensor array having reflective elements coupled with a handle of the tool. The registration tool may also include a pointer end that is used to register points of a bone. The reflective elements may be positioned in a configuration that enables the computing device to determine the identity of the registration tool and its relative location (i.e., the location of the pointer end). Additionally, reference arrays may be used on other surgical tools such as a tibial resection jig. The jig may include a resection guide portion that is coupled with a tibia bone at a location of the bone that is to be resected. The jig may include a reference array that is coupled with the portion via a frame. The reference array 146 may include three reflective elements 148 that may be positioned in a configuration that enables the computing device to determine the identity of the jig and its relative location (e.g., with respect to the tibia bone).

During the performance of the orthopaedic surgical procedure, a custom surgical plan may include one or more instructions that program or otherwise configure the HUD to display images of the individual surgical procedure steps which form the orthopaedic surgical procedure being performed. The images may be graphically rendered images or graphically enhanced photographic images. For example, the images may include three dimensional rendered images of the relevant anatomical portions of a patient. The surgeon may interact with the computing device to display the images of the various surgical steps in sequential order. In addition, the surgeon may interact with the computing device to view previously displayed images of surgical steps, selectively view images, instruct the computing device to render the anatomical result of a proposed surgical step or procedure, or perform other surgical related functions. For example, the surgeon may view rendered images of the resulting bone structure of different bone resection procedures. In this way, the custom surgical plan may configure the system0 to provide a surgical "walk-through" customized to the patient 106 that the surgeon may follow while performing the surgical procedure.

In one embodiment, the custom surgical plan may include an ordered selection of instructional images that depict individual surgical steps that make up at least a portion of the orthopaedic surgical procedure to be performed. The instructional images may include images of surgical tools and associated text information, graphically rendered images of surgical tools and relevant patient anatomy, and/or other images and/or text information that assist the surgeon during the surgical procedure. The instructional images may be stored in an electronic library, which may be embodied as, for example, a database, a file folder or storage location containing separate instructional images and an associated look-up table, hard-coded information. The surgical plan may include among other things an ordered selection of instructional images that are displayed to the surgeon via the display device 3094 such that the instructional images provide a surgical "walk-through" of the procedure or portion thereof. The surgical plan may also include a number of surgical sub-step images, some of which may or may not be displayed to and performed by the surgeon based on selections chosen by the surgeon during the performance of the orthopaedic surgical procedure.

In some embodiments, the surgeon may also interact with the computing device to control various devices of the system0. For example, the surgeon may interact with the system0 to control user preferences or settings of the AR display device 3094. Further, the computing device may prompt the surgeon for responses. For example, the computing device 62 may prompt the surgeon to inquire if the surgeon has completed the current surgical step, if the surgeon would like to view other images, and/or other surgical procedure inquiries.

The AR system may be used to generate pre-operative orthopaedic surgical plans, surgical notes created during an orthopaedic surgery, medical images of a patient's bone (and soft tissue) and/or orthopaedic implants coupled thereto, and/or other data. Such data generated via the system0 may be stored in the database by, for example, transmitting the data from the system0 to the database via the network. Additionally, other medical devices typically found in a hospital or other healthcare facility may be used to generate medical images of a bone (and, in some embodiments, soft tissue) of the patient. Such medical images may also be stored in the database. The medical images may be embodied as any type of medical image providing a visual indication of a relevant bone or bones (and soft tissue if desired) of a patient. For example, the medical images may be embodied as any number of X-ray images, magnetic resonance imaging (MRI) images, computerized tomography (CT) images, or the like. Regardless, such medical images may be stored in the database 28 along with associated data relevant to the particular medical images. Such associated data may include, but is not limited to, the patient's name and other patient identification information, date of the images, surgeon's or doctor's name, the name of the hospital or healthcare facility wherein the medical images were generated, and the like.

Car Repair/Maintenance

In one embodiment, the AR display can be used to assist smart vehicles. Information from sensors can be displayed usings a heads-up display (HUD) or the AR system. The sensors can be part of a car, a motorcycle, a bicycle, a boat, a plane, a dirigible, or a drone, for example. FIG. 13 shows an exemplary smart vehicle. The sensors can be used for maintenance prediction and in case of component failure, to help the driver to navigate safely. For example, the vehicle can monitor brake pad wear and adjusting how hard the brake needs to be applied in light of other vehicles and how fast does the vehicle need to come to a complete stop. In addition to changing the way the vehicle brake, the vehicle may change the way it maneuvers in other ways as well, such as accelerating differently or changing directions. For instance, the vehicle may accelerate more slowly if the measured oil pressure is excessively high. The vehicle may also turn more or less tightly in order to mitigate wear. The vehicle may also use other systems and methods to determine the state of a vehicle component. For example, the vehicle may monitor how far it takes the car to stop compared to expected braking distance. If the distance is longer than expected, such as taking longer than it has in the past, the computer system may determine that the brakes are worn and start braking earlier. The system and method may also estimate the state of a component based on its repair service record. In that regard, the processor may query data 134 or an external database (e.g., a server with which the vehicle is in wireless communication) for repair records and estimate the wear on a component based on the length of time since the last repair.

The system and method may rely on other information to change the way the vehicle is maneuvered. For instance, the vehicle may sense weight distribution and adjust maneuvering in response to the changes in the loading and/or weight distributions on the vehicle. The vehicle may further move differently when there is only one user in the vehicle than four passengers on board, or differently with light loads than with hauling a trailer behind. The vehicle may also adapt the driving to the observed environmental changes such as weather or roadway conditions.

Modeling of the patterns of changes in the vehicle's performance and conditions, as well as modeling of the patterns of changes in the driving environment, may be performed by the autonomous driving computer system. Alternatively, predetermined models may be stored in the autonomous driving system. The computer system may process the observed data, fit them into the 3D models in FIGS. 7A-7I, and issue compensation signals accordingly.

The vehicle may take the steps necessary to repair a component. By way of example, when the vehicle is not being used by anyone, the vehicle may autonomously and without direct human assistance navigate to a repair facility, notify the facility of the component that requires repair and return to its original location when the repair is finished.

Control of Vehicle Using Cameras on AR Unit

Exemplary control of the car using eye control with the AR unit is detailed next. The eye control can work stand alone, but also can work together with voice control and/or hand control of a smart vehicle for added authentication. First, a Left Hand Gesture, voice and eye based Car Control process is disclosed. In an exemplary left arm gesture, voice and eye based window glass control process, the process checks for the focus point of the eye, optionally confirmed by a raised arm (1002). If the arm is raised (1004) it checks for the number of fingers raised (1006). The controls for windows are activated if first four fingers are raised (1008). The process allows controlling only the driver seat glass control and also all the window glass control. This decision is based on the number of fingers raised. A single finger chooses only driver glass. Movements of the glass is than controlled by the angular movement of the arm (1020), a right movement slides the glass up (1028) and a left movement slides it down (1026). The process is concluded (1030) after the windows are at the required position. At any moment the driver can choose to exit the process by forming a first of his left arm. Voice can be used to confirm the command.

A seat control process is capable of controlling both the driver seat and the front passenger seat as well. The process starts with checking for eye looking at a desired seat, and then which arm is raised (1036). After the arm the process scans for the fingers (1038), first 2 fingers initiate the seat actuators (1040). Now, the driver can choose to adjust his own seat or maybe the seat of the passenger. This decision is dependent whether one or two fingers are raised (1044). The seats can be moved forth or back as per the arms angular movement (1052) (1050). As per the convenience, the seats can be adjusted. After the adjustment is done, the process concludes (1062). At any point the process can be ended if the driver forms a first on left hand.

A left hand based gesture, voice and eye based mechanism for unlocking the 'Hood' and the 'Trunk' of the car is next. As it is left arm based control, the mechanism uses a camera to check which object is being looked at, and also the arm raised. A raised left arm initiates the process which unlocks the hood and trunk (1068). The camera than checks for the fingers that are raised (1070), the first finger is used to activate the hood & trunk control (1072). To open the trunk the driver has to make a right angular movement (1076) and an opposite movement for unlocking the hood (1078). As soon as either of the two is unlocked the process ends (1082). If the process is started by mistake or confusion, the driver can choose to exit by forming a first on his left arm.

An exemplary process for controlling temperature of the driver and front passenger seats is next. After checking for left raised arm (1088) the camera scans for the fingers raised (1090). The first three fingers are to be used by the driver to activate seat temperature controls (1092). The driver can choose to control his seat temperature or the passenger's seat temperature by raising the appropriate number of fingers (1096). The angular movements of the left arm can be used to increase or decrease the temperature of the selected seat (1104) (1102). The process can be ended after adjusting the temperature or at any other point by forming a first (1114).

An left arm gesture, voice and eye based navigation (GPS) control for a car is next. The process initializes when the driver raises his/her left arm (1120). The GPS system is activated if the all the fingers are raised i.e. an open palm (1124). Now the arm motion in the vertical and horizontal axis can be used to move the GPS pointer (1128). To select a particular destination, the pointer must be kept at the same location for a pre-defined duration of time (1144). Once the destination is set, the GPS starts routing (1146) and then exits the process (1148). The process can be ended abruptly if needed by forming a first on left hand.

An exemplary gesture, voice and eye based control of drivers mirror using left arm is next. The driver initiates the process by raising the left arm (1154). The thumb is used as a trigger for activating the mirror actuators (1158). To adjust the mirror angle, the driver can move his/her arm along the vertical or horizontal axis (1162). The driver can form a first (1170) (1168) or wait for a predefined time interval to set the mirror angle (1182). This process has an option which enables the driver to exit anytime by forming a first on left hand.

An exemplary music control in the car using gestures of right hand is next. The process is activated if the camera scans a vertically standing right arm (1190). The car music system is initiated if the driver has an open right palm (1194). Depending upon the fingers raised after the music system is initiated either radio or just the MP3 player is started (1204). The angular movements of the arm can be used to switch between stations or songs (1206) (1202). Once the desired station or song is selected the driver can exit the process by forming a closed first (1216). A closed first formed anytime can be used to exit the process anytime.

An exemplary car temperature control using gestures from the right arm follows. The driver is expected to raise the first two fingers of the right arm to activate the temperature controls (1246). The temperature controlling element is the angular motion of the right arm (1250). A left motion causes decrease in temperature and vice versa (1256) (1254). Once the desire temperature is achieved, the driver can stop the process by forming a fist. A first basically exits the process at any given point.

An exemplary control the car volume using arm gestures is next. The camera initiates the process whenever the driver raises his/her right arm (1222). The process expects the driver to raise three fingers to initiate volume control (1226). Using the right or left angular motion the volume can be increased and decreased (1230).

An exemplary technique for sliding the sun roof by the means of hand gesture can be as follows. The sun roof control process starts when the driver raises his/her right arm (1264) and first four fingers of the same (1268). The camera now scans for the angular motion of the arm (1272). A left motion pulls the roof back (1276) whereas a right motion pushes it forward so that it can be closed (1274). The process ends once the roof is entirely opened or closed and it can also be concluded by forming a first on the right arm.

An exemplary arm gesture, voice and eye based technique for controlling the car wind shield wipers is next. The wiper motors are activated when the right arm along with first finger is raised (1284) (1288). The speed of the wiper motors can be controlled using the right arm angular motion (1292). The left motion decreases the speed (1298), the right motion increases the wiper speed (1296) and in order to stop the wiper a still right arm with a closed first should be scanned by the camera (1294).

An exemplary right arm gesture, voice and eye based control of the rear view mirror is next. The camera scans for the right arm, if it is up the process is initiated (1306). The rear view mirror control is activated if the camera scans only a thumb on right arm (1310). Now, the rear view mirror can be adjusted vertically and horizontally, this is achieved by moving the arm with only raised thumb along the desired axis (1314). To lock the position of the mirror, the same position is to be maintained for a pre-defined interval of time. Once done the process locks the mirror and concludes (1332). The process can be ended anytime by the driver by forming a first on his right arm.

In other embodiments, by cupping the hand on an object such as a steering wheel, the user can use voice to make calls, receive and respond to texts, launch apps, get turn-by-turn directions, find the nearest Chinese restaurant and other local businesses, or say "Play me some Barry Manilow." You can also ask Siri or Google Now to search the Internet as you roll down the Interstate. The apps will be able to pull contacts directly from the phone's address book, access favorites and bookmarks, and have user location history close at hand.

A gesture is used to control an air conditioning system in an example vehicle, in accordance with an embodiment. The vehicle may maintain a correlation between a plurality of predetermined gestures, in combination with a plurality of predetermined regions of the vehicle, and a plurality of functions, such that each gesture in the plurality of predetermined gestures, in combination with a particular region of the plurality of predetermined regions, is associated with a particular function in the plurality of functions, as described above. For example, the correlation may include a downward swiping gesture in a region that includes an air-conditioning vent associated with the function of decreasing a fan speed of an air conditioning system. Other examples are possible as well.

As shown, a fan speed indicator on the display indicates that a fan speed of the air conditioning system in the vehicle is high. At some point, the user may wish to lower the fan speed of the air conditioning system. To this end, the user may make a downward swiping gesture in a region that includes an air-conditioning vent. The camera 304 may record three-dimensional images of the downward swiping gesture in the region that includes an air-conditioning vent. Based on the three-dimensional images, the vehicle may detect the downward swiping gesture in the region that includes the air-conditioning vent.

The vehicle may then select, based on the correlation, a function associated with the downward swiping gesture in the region that includes the air-conditioning vent. For example, the downward swiping gesture in the region that includes the air-conditioning vent may be associated with the function of decreasing a fan speed of the air conditioning system, as described above. Other examples are possible as well. Once the vehicle has selected the function from the correlation, the vehicle may initiate the function in the vehicle. That is, the vehicle may decrease the fan speed in the vehicle.

In some embodiments, the vehicle may additionally determine an extent determining an extent of the downward swiping gesture and may decrease the fan speed by an amount that is, for example, proportional to the extent.

In some embodiments, in addition to initiating the function, the vehicle may trigger a feedback to the user, such as an audible feedback, a visual feedback, and/or a haptic feedback. Such feedback may be particularly useful when the function is not immediately detectable by the user, such as a small decrease in the fan speed of the climate control system or a slight repositioning of a seat.

Further, in some embodiments, the vehicle may determine an extent of the given gesture. For example, if the given gesture is a swipe gesture, the vehicle may determine an extent of the swipe (e.g., how long the swipe is in space and/or time). The vehicle may then determine an operational parameter based on the extent. For example, for a greater extent, the vehicle may determine a greater operational parameter than for a lesser extent. The operational parameter may be, for example, proportional to, or approximately proportional to, the extent. In these embodiments, when the vehicle initiates the function the vehicle may initiate the function with the determined operational parameter.

For example, if the swipe gesture is in a region that includes a window, and the swipe gesture in the region that includes the window is associated with opening the window, the vehicle may determine an extent of the swipe and further may determine how far to open the window based on the extent of the swipe. For instance, the vehicle may open the window further for a longer swipe than for a shorter swipe.

As another example, if the swipe gesture is in a region that includes an air-conditioning vent, and the swipe gesture in the region that includes the air-conditioning vent is associated with lowering a temperature in the vehicle, the vehicle may determine an extent of the swipe and further may determine how much to lower the temperature in the vehicle based on the extent of the swipe. For instance, the vehicle may lower the temperature further for a longer swipe than for a shorter swipe.

Such an extent could be determined for gestures other than a swipe gesture as well. For example, if a tap gesture is in a region that includes a speaker, and the tap gesture in the region that includes the speaker is associated with lowering a volume of an audio system, the vehicle may determine an extent of the tap (e.g., how many taps, how long the tap is held, etc.) and further may determine how much to lower the volume of the audio system based on the extent of the tap. For instance, the vehicle may lower the volume more for more taps (or a longer tap) than for fewer taps (or a shorter tap).

In some embodiments, rather than determining the extent of the gesture and the corresponding operational parameter and then initiating the function with the determined operational parameter, the vehicle may instead continuously determine the extent of the gesture and update the corresponding operational parameter, and may continuously initiate the function with the updated operational parameter. For example, the vehicle may detect a cover gesture in a region that includes an air-conditioning vent (e.g., such that the air-conditioning vent is covered), and the cover gesture in the region that includes the air-conditioning vent may be associated with lowering a fan speed of the air conditioning system. Once the vehicle detects the cover gesture in the region that includes the air-conditioning vent, the vehicle may lower the fan speed (e.g., by a predetermined amount). As the vehicle continues to detect the cover gesture, the vehicle may continue to lower the fan speed (e.g., in increments of, for example, the predetermined amount, growing amounts, etc.). Once the vehicle detects that the cover gesture has ended, the vehicle may cease to lower the fan speed. As a result, during the cover gesture the vehicle may lower the fan speed by an amount that is based on the extent of the cover gesture.

In some embodiments, the vehicle may have difficulty detecting the given gesture and/or the given region. For example, the vehicle may determine that a confidence level of one or both of the given gesture and the given region is below a predetermined threshold. In these embodiments, the vehicle may request an occupant to repeat the given gesture in the given region. When the occupant repeats the given gesture in the given region, the vehicle may record additional three-dimensional images and may detect the given gesture and the given region based on the additional three-dimensional images (and, in some cases, the three-dimensional images previously recorded).

Flock Navigation

Next a flock control behavior is detailed. In one embodiment, the eye gaze of the driver is detected using the AR camera pointing at the eye. The user can look at a particular to lock in the vehicle as a leader car. In other embodiments, a plurality of cars follow a leader car, who in turn is following a target vehicle or a target driving plan. The leader, or the first car in the group would automatically or manually take evasive actions to avoid an obstacle, and the information is transmitted via vehicle to vehicle communication such as DSRC to following vehicles, and the driving path of the entire flock is adjusted according to the obstacle. "Flocking" is the collective motion of a large number of self-propelled entities and is a collective animal behavior exhibited by many living beings such as birds, fish, bacteria, and insects. It is considered an emergent behavior arising from simple rules that are followed by individuals and does not involve any central coordination. The vehicle communications would identify vehicles traveling as a flock, and the vehicles perform distributed flocking operation by communication over the wireless network.

The vehicles can be organized into a V formation (sometimes called a skein) is the symmetric V-shaped formation for Drag Reduction and Fuel Saving where all the cars except the first drive in the upwash from the wingtip vortices of the car ahead. The upwash assists each car in supporting its own weight in flight, in the same way a glider can climb or maintain height indefinitely in rising air.

A flock of automatically driven motor vehicles is detailed next, each having the flock behavior. The motor vehicles of the flock establishes a target motor vehicle which will be used as a reference for flocking. The leading motor vehicle of the flock is established as the target motor vehicle by the motor vehicles of the flock. The target motor vehicle may be established before the motor vehicle start miming in flock. In another embodiment, the first motor vehicle of the flock detects a preceding motor vehicle with the information from the radar or the CCD camera on the leading motor vehicle or flock leader, and automatically establishes the detected preceding motor vehicle as a new target motor vehicle. By successively changing new target motor vehicles in this manner, new motor vehicles may automatically be added to the flock. Even if a motor vehicle is incapable of communication between motor vehicles, that motor vehicle may be established as a target motor vehicle according to an algorithm described later on.

In one embodiment, the leading motor vehicle of the flock establishes a hypothetical target motor vehicle, and transmits items of information of the hypothetical target motor vehicle to the other motor vehicles of the flock which follow the flock leader through the inter-vehicular communications such as DSRC.

Each vehicle in the flock is responsible for generating a speed plan which governs the relationship between the position in which the motor vehicle runs and the speed at which the motor vehicle runs. The vehicles perform determining, based on the speed plan, a planned position to be reached from the present position of the motor vehicle after a predetermined time t, e.g., 1.5 seconds, and a planned speed of the motor vehicle at the planned position in the flock. According to this function, if the speed plan from the present position of the motor vehicle is generated such that the motor vehicle is to maintain the speed of 80 km/h, i.e., 22.2 m/sec., then the planned position to be reached after the predetermined time t, e.g., 1.5 seconds, is 33.3 m spaced from the present position down the running path B, and the planned speed at the planned position to be reached is 80 km/h.

The function as the predicted value calculating means serves to determine a predicted position and a predicted speed to be reached by the motor vehicle after the predetermined time t. The predicted position is calculated from the present position, i.e., the traveled distance, the present speed, and the present acceleration of the motor vehicle which are given from the communication module 1, and the predicted speed is calculated from the present speed and the present acceleration of the motor vehicle.

The speed/acceleration of the vehicle, based on which the predicted position and the predicted speed will be determined, is basically determined from the speedometer. The predicted position and the predicted speed are determined using the speed and the acceleration of the motor vehicle and GPS position.

A distance deviation, i.e., a position error, between a planned position to be reached by the motor vehicle after the predetermined time t based on the speed plan and the predicted position, described above, to be reached by the motor vehicle, and a speed deviation, i.e., a speed error, between a planned speed to be reached by the motor vehicle after the predetermined time t based on the speed plan and the predicted speed, described above, to be reached by the motor vehicle are determined. These deviations are calculated by subtractions. The target motor vehicle may be a flock leader. If, however, the target motor vehicle is not a flock leader, then the flock leader calculates a position, a speed, and an acceleration of the target motor vehicle using the laser radar, GPS, or triangulation of RF signals, for example. Based on the above control algorithm, the engine throttle valve opening, the transmission, and the brake of each of plural following motor vehicles are controlled to control the motor vehicles in a flock. The system detects the positional data of the preceding motor vehicle through inter-vehicular communications or the laser radar, and controls the following motor vehicle in the event that the preceding motor vehicle drops out of a normal control range of the vehicle flock control. Even when a motor vehicle drops out of the normal range of the vehicle flock control, the control algorithm controls a following motor vehicle to increase its inter-vehicular distance up to such a motor vehicle. Therefore, the vehicle platoon control will not be interrupted even when one or more motor vehicles drops out of the platoon. If it is known that a group of motor vehicles will travel in platoon or motor vehicles are counted at a tollgate or the like and the incremental count is indicated to each motor vehicle to let it recognize its position in the platoon, then it is possible to establish the position i for each of the motor vehicles before they travel in platoon. However, in order to handle a situation where another motor vehicle pulls in between motor vehicles running in platoon or another motor vehicle is added to a front or rear end of a platoon of motor vehicles, the process according to the present invention makes it possible for each of the motor vehicles running in flock to recognize its position relative to a target motor vehicle through inter-vehicular communications. There are two procedures available for each of the motor vehicles running in flock to recognize its position relative to a target motor vehicle. The first procedure is applicable to local inter-vehicular communications by which each of the motor vehicles of the flock can communicate with only those motor vehicles which run immediately in front of and behind the motor vehicle. If the flock leader of a flock is selected as a target motor vehicle, then the target motor vehicle transmits its own positional information i=0 to a next motor vehicle which immediately follows the target motor vehicle. The following motor vehicle adds 1 to i, producing its own positional information i=1, recognizes that it is the second motor vehicle from the target motor vehicle, and transmits its own positional information i=1 to a next motor vehicle which immediately follows the second motor vehicle. Having received the positional information i=1, the next immediately following motor vehicle adds 1 to i, producing its own positional information i=2, recognizes that it is the third motor vehicle from the target motor vehicle, and transmits its own positional information i=2 to a next motor vehicle which immediately follows the third motor vehicle. In this manner, each of the motor vehicles is able to recognize its position relative to the target motor vehicle with a means for counting its position and local inter-vehicular communications.

If a target motor vehicle is not the flock leader of a flock and the target motor vehicle and the flock leader cannot communicate with each other through inter-vehicular communications, then the flock leader sets its own positional information to i=1, and transmits the own positional information i=1 to a next motor vehicle which immediately follows the target motor vehicle.

According to the present invention, as described above, a longitudinal acceleration correcting quantity of each of the motor vehicles of a flock is determined on the basis of predicted deviations of a position and a speed that are predicted after a predetermined time, from a speed plan, and the speed of the motor vehicle is controlled on the basis of the determined longitudinal acceleration correcting quantity. Therefore, the motor vehicles can smoothly be controlled to run in flock along a running path on a road.

A longitudinal acceleration correcting quantity of a motor vehicle following a target motor vehicle is determined on the basis of an inter-vehicular distance between the following motor vehicle and the target motor vehicle and a speed difference there-between after a predetermined time, and the speed of the following motor vehicle is controlled on the basis of the determined longitudinal acceleration correcting quantity. Consequently, the following motor vehicle can automatically be driven smoothly along a running path on a road while reliably keeping a proper inter-vehicular distance between the following motor vehicle and the target motor vehicle.

Since the system arrangements on a flock leader and a following motor vehicle of a flock are identical to each other, the flock leader and the following motor vehicle can automatically be driven in a manner to match them using slightly different software or program adaptations made therefor. Therefore, any one of the motor vehicles of the flock may become a flock reader or a following motor vehicle.

Each of following motor vehicles of a flock is not only controlled with respect to a flock leader, but also always monitors an inter-vehicular distance between itself and a preceding motor vehicle, so that it can increase the inter-vehicular distance even when a motor vehicle drops out of the flock. Therefore, it is not necessary to stop controlling the vehicle flock control when a motor vehicle drops out of the flock. Even when a motor vehicle drops out of a flock, the vehicle flock control system does not stop controlling the other motor vehicles to run in flock, and when the motor vehicle that has dropped out returns to the flock, the vehicle flock control system can continuously control the motor vehicles to run in flock. The vehicle flock control system allows different types of motor vehicles, such as trucks of different lengths, smaller automobiles, larger automobiles, etc., to be mixed in a flock, and can control those motor vehicles to run in flock. Accordingly, the vehicle flock control system according to the present invention is capable of stably controlling motor vehicles to run in flock on a road designed for motor vehicles to run automatically, and particularly of controlling the speeds of such motor vehicles smoothly.

It will be understood that the present invention may be used for both fleets of vehicles and for individual drivers. For example, the driver monitoring system described herein may be used by insurance providers to monitor, recommend, provide feedback, and adjust insurance rates based on the driving. A private vehicle owner may also use the present invention to monitor the driver behavior and user of the vehicle. For example, a parent may use the system described herein to monitor a new driver or a teenage driver behavior.

An embodiment of the invention provides real-time recommendations, training, or other feedback to a driver while operating the vehicle. The recommendations are based upon observed operation of the vehicle and are intended to change and improve driver behavior by identifying improper or illegal operation of the vehicle. The driver monitoring system may identify aggressive driving violations. For example, based upon the inputs from an acceleration or CDR, aggressive driving behavior can be detected, such as exceeding acceleration thresholds in a lateral, longitudinal, or vertical direction, hard turns, hard acceleration or jackrabbit starts, hard braking, and/or hard vertical movement of the vehicle.

Further, in an embodiment, the sensor and camera described herein can be configured to communicate with the vehicle entertainment system. Typically, this functionality includes pre-installed software or a user-downloadable application from a network source (such as Apple's iTunes or Google's Android Market). The system functionality may include mapping functions, directions, landmark location, voice-control, and many other desirable features. When such mobile computing device is placed within the vehicle then a convenient vehicle entertainment system associated with the vehicle can be provided. In an embodiment, a remote switch can be used to initiate the vehicle entertainment software application by communicating with the cameras/sensors located in the vehicle and/or software residing on the mobile computing device. Remote switch described herein can include one of a number of well-known remote switches that uses wireless or wired technology to communicate with mobile computing device. For example, remote switch may include for example, but not limited to, a Bluetooth, RF, infrared, or other well-known wireless communication technology, or it may be connected via one or more wires to mobile computing device. The switch may be located on any vehicle interior surface, such as on a steering wheel, visor, dashboard, or any other convenient location.

In an embodiment, the cameras or sensors may be placed at any place in the vehicle, such as for example at four corners of the front windshield, in a way that it can directly capture the behavior parameters of the driver. For example, based on the driver gestures, the cameras can detect finger position to detect that driver is pointing at a particular object or vehicle and searches the internet for the vehicle. Further, in an embodiment, a flexible display film adhesively secured on the front windshield. The display can be used controlled by a computer to display info in a discrete way that may not take driver's eyes off the road and opposing vehicles. In an embodiment, at 4404, the driver monitoring unit 4102 can be configured to transmit the behavior parameters of the driver to the server 4106. In an embodiment, the driver behavior parameters described herein can include for example, but not limited to, vehicle speed, vehicle accelerations, driver location, seatbelt use, wireless device use, turn signal use, driver aggression, detection of $CO_2$ vapor, detection of alcohol, driver seating position, time, and the like. In an embodiment, at 4406, the server 4106 can be configured to transmit the driver behavior parameters to one or more insurance providers. In an embodiment, at 4408, the server 4106 can be configured to analyze the driver behavior parameters and adjust the insurance rates for the driver. For example, if the driver is driving roughly by drinking alcohol then the insurance rate may get decreased. In an embodiment, at 4410, the server 4106 can be configured to match the driver behavior preferences with similar or substantially similar preferences of other drivers. The server 4104 can be configured to generate action recommendations best matching the behavior of the driver. In an embodiment, at 4412, the server 4106 can be configured to provide the generated recommendations to the driver. Based on the driver behavior parameters the sever 4106 provides feedback and recommendations to the driver, such as to improve the driving skills. Further, in an embodiment, a flexible display film adhesively secured on the front windshield. The display can be used controlled by a computer to display info in a discrete way that may not take driver's eyes off the road and opposing vehicles. In an embodiment, at 4414, the server 4106 can be configured to frequently monitor the behavior parameters associated with the driver. Any changes in the behavior parameters can affect the overall system performance and the driver experience. The server 4106 can be configured to frequently monitor and dynamically update the insurance rate and action recommendations, which in turn helps the driver for effectively improving the driving skills.

In an embodiment, the driver behavior parameters can be used to provide customized recommendations to drivers by comparing the driver behavior parameters with other drivers who has similar or substantially similar behavior parameters. Unlike conventional system, the server 106 can be configured to adaptively generate action recommendations for the driver based on the behavior parameters. The server 106 can be configured to match the behavior parameters of the drivers to similar behavior parameters of the one or more drivers, such as to provide personalized action recommendations to the driver. In an embodiment, the recommendations can be filtered in advance of display. In an embodiment, filtered recommendations may be derived from the sources such as for example, but not limited to, those sources that have added the data within a specified time, from those sources that share specific similarities with the sources, those sources that have been preselected by the driver as relevant, those sources that are selected as friends or friends of friends, and the like, those sources that are determined to provide valuable reviews/ratings or are specifically declared to be experts within the system or by the driver, or those users that have entered at least a minimum amount of data into the system.

The system can monitor the driver behavior and uses the behavior data to match with the behavior data of other sources and provide action recommendations to the driver. For example, if the driver behavior parameter indicates that the user is driving very fast (such as 70 kmph) in school zone where the speed limits should be more than 30 kmph then the system can be configured to execute one or more rules and provide suggestions to the driver to slow down the speed. Rules can be derived from, for example, but not limited to, automatic generation machine learning, automatic generation using a generic algorithm, automatic generation using a neutral network, automatic generation using a rule inference system, data mining, generation using a preset list of recommendations, and/or a driver behavior. In an embodiment, the sever 106 can be configured to receive the recommendation rules such as unidirectional rules, bidirectional rules, generalized rules including multi-way rules, rules among items, rules among sets, rules among collections, rules with weight factors, rules with priorities, unweighted and un-prioritized rules, and the like.

A method 4700 is used for selectively providing insurance information to a service provider, according to embodiments as disclosed herein. At step 4702, the driver behavior is monitored. The behavior data can include external parameters and/or internal parameters. In an embodiment, the driver behavior data/parameters described herein can include for example, but not limited to, vehicle speed, vehicle accelerations, driver location, seatbelt use, wireless device use, turn signal use, driver aggression, detection of ethanol vapor, driver seating position, time, and the like. In an embodiment, the behavior data can be over a period of hours, days, weeks, and so forth. In an embodiment, the behavior data gathering can be continuous, at predefined intervals, or at random intervals. In accordance with some aspects, data can be gathered while a vehicle is in operation and at other times (e.g., at two a.m. to determine where the vehicle is parked overnight). In an embodiment, a change to an insurance premium and/or an insurance coverage is prepared, at 4704. The change is based on one or more of the driver behavior data, wherein each item of driver behavior data can have a different weight assigned. For example, data gathered related to weather conditions might be given less weight than data gathered related to user distractions (e.g., passengers, use of a mobile device while vehicle is in operation, and so forth). In another example, excessive speed might be assigned a higher weight than data related to safety performance of the vehicle. As such, data with a higher weight can be given more consideration than data with a lower weight (e.g., data assigned a higher weight can have a greater impact on the cost of insurance). Thus, if the user is traveling at (or below) the speed limit and speed is assigned a greater weight, then the safe speed will tend to decrease (or remain constant) the cost of insurance.

In an embodiment, the driver is notified of the change, at 4706. The notification can be in any perceivable format. In an example, the notification is provided as a dashboard-mounted display. In another example, presenting the change can include displaying the modified cost of the insurance policy in a dashboard-mounted display and/or a heads-up display. In an embodiment, a service provider is notified of the change, at 708. At substantially the same time as notifying the service provider (or trusted third party) of the change, parameters taken into consideration (and associated weight) can also be provided. In such a manner, the service provider (or third party) can selectively further modify the cost of insurance, which can be communicated to the user though the vehicle display or through other means.

The service provider (or third party) might be provided the change information less often than the insurance cost change information is provided to the user. For example, the user can be provided the insurance cost change information dynamically and almost instantaneously with detection of one or more parameters that can influence the insurance cost. However, the insurance provider (or third party) might only be notified of the change after a specified interval (or based on other intervals). For example, insurance cost changes might be accumulated over a period of time (e.g., two weeks) and an average of the insurance cost changes might be supplied to insurance provider. In such a manner, the user has time to adjust parameters that tend to increase (or decrease) the cost of insurance, which allows the user to have more control over the cost of insurance.

In an embodiment, Vertical market specialization for insurance is provided where markets are defined based on granular aspects of coverage and presented to one or more insurance subsystems to obtain quotes for a coverage premium. Such specialization allows insurance companies to compete in more specific areas of insurance coverage, which allows for more accurate premium rates focused on the specific areas or one or more related scenarios. In addition, the granular aspects of coverage can be provided to one or more advertising systems in exchange for further lowered rates, if desired.

According to an example, an insurance market can be defined based on granular information received regarding an item, a related person, use of the item, etc. Based on the market, premium quotes can be obtained from one or more insurance subsystems related to one or more insurance brokers. In addition, rates can be decreased where the granular information can be provided to an advertising system, in one example. In this regard, targeted advertisements can additionally be presented to system related to requesting the insurance coverage. Policies can be automatically selected based on preferences, manually selected using an interface, and/or the like.

An exemplary system customizes insurance rates to correspond to behavior driver, according to embodiments as disclosed herein. In an embodiment, the server 4106 can be configured to maintain a database component 4802 including data related to different driver behaviors. Such leveraging from data banks enables insurance providers to bid in real time, and hence an owner and/or user of a vehicle can benefit from competition among various insurance providers, to obtain optimum rates. The server includes a rate adjustment component 4804 that in real time can determine the various rates from a plurality of insurance providers 4110 (1 to N, where N is an integer). In one particular aspect, a retrieval agent (not shown) associated with the rate adjustment component 4804 can pull insurance data from the insurance providers based on the contextual data supplied thereto. For example, such contextual data can be data records related to driver behavior, the vehicle 4102 (such as auto shop service records, current service status for the car, and the like), data related to the individual driver (such as health records, criminal records, shopping habits, and the like), data related to the environment (road condition, humidity, temperature, and the like) and data related to real time driving (frequency of braking, accelerating, intensity of such actions, and the like).

The retrieval agent (not shown) can pull data from the insurance providers 4110 and further publish such data to enable a rich interaction between the users on a display or a within a written communication environment. The retrieval agent can further generate an instance for a connection with the insurance providers. Accordingly, a connection instance can be employed by the rate adjustment component 4804 to store connection information such as the state of data conveyance, the data being conveyed, connection ID and the like. Such information can additionally be employed to monitor progress of data transfer to the written communication environment or display, for example. Accordingly, drivers/owners of motor vehicles can pull or receive data from the insurance providers 4110, wherein received data can be posted (e.g., displayed on a monitor) and the connection instance can be concurrently updated to reflect any successful and/or failed data retrievals. Thus, at any given moment the connection instance can include the most up-to-date version of data transferred between the motor vehicle and the insurance providers. In an embodiment, a switching component 4806 can be configured to automatically switch user/driver to an insurance provider/company that bids the best rate. Such switching component 4806 can employ interrupts both in hardware and/or software to conclude the switching from one insurance provider to another insurance provider. For example, the interrupt can convey receipt of a more optimal insurance rate or completion of a pull request to the insurance providers 4110 or that a configuration has changed. In one particular aspect, once an interrupt occurs, an operating system analyzes the state of the system and performs an action in accordance with the interrupt, such as a change of insurance provider, for example Cameras can be used to capture traffic information, according to embodiments as disclosed herein. In an embodiment, at 5402, the method 5400 includes mounting cameras on the car to monitor the traffic information. For example, the car may include cameras mounted to capture views in the rearward, downward, and the like directions, on the upper surface at the leading end of the front portion thereof. The position for mounting the cameras is not limited to the left side, right side, upper surface, front side, back side, and the like. For example, if the car has a left side steering wheel, the camera may be mounted on a right upper surface at a leading end of the front portion of the car. The cameras may have an angle of view of about 60, 90, 180, and 360 degree. With the construction, since the camera is mounted for a view in the rearward and downward directions on the front portion of the car, it can capture a wide area of the surface of the road in the vicinity of the driver's car, and an area in the vicinity of the left front wheel. Furthermore, the camera can also capture a part of the body of the car in the vicinity of the front wheel. Thereby, the relation between the car and the surface of the road can be recorded. In an example, the cameras can be configured to capture images of the road views including potential collision events such as how close car is following car in front, how often brake is used in period of time, hard brakes count more to reduce driver rating, how frequently does car come close to objects and obstructions (such as trees, cars on the other direction and cars in same direction) while moving. In an embodiment, at 5404, the method 5400 includes receiving the recorded information from the camera and use image processing techniques to process the information. For example, the system uses image processing techniques to determine potential collision events such as how close car is following car in front, how often brake is used in period of time, hard brakes count more to reduce driver rating, how frequently does car come close to objects and obstructions (such as trees, cars on the other direction and cars in same direction) while moving. In an embodiment, at 5502, the method 5500 includes mounting cameras on the car to monitor the driver behavior. The position for mounting the cameras is not limited to the left side, right side, upper surface, front side, back side, and the like. The cameras may have an angle of view of about 60, 90, 180, and 360 degree. For example, the camera can capture driver behavior such as for example, but not limited to, images of texting and use of phone while driving, speech of driver shouting or cursing at other drivers or other occupants, indications of intoxication, sleepiness, alcohol level, mood, aggressiveness, and the like. In an embodiment, at 5504, the method 5500 includes receiving the recorded information from the camera and use image processing techniques and voice reorganization techniques to process the information. For example, the system uses image processing techniques to determine the driver activity such as whether the driver is using mobile phone while driving. In another example, the system uses voice recognition techniques to determine the use voice, text, aggressiveness, and the like. In an embodiment, the item-centric approach determines that many drivers having similar behavior and the driver who performs activity-A will also perform activity-B. This has proven to be fairly effective. On the other hand, many insurance providers interact with drivers online/offline. Such interaction can produce a stream of contextual information that recommendation engines can use. Early systems were batch oriented and computed recommendations in advance for each driver. Thus, they could not always react to a driver's most recent behavior. Recommendation engines work by trying to establish a statistical relationship between drivers and activities associated with there behavior. The system establishes these relationships via information about driver's behavior from vehicle owner, monitoring devices, sensors, and the like. In an embodiment, the recommender systems collect data via APIs, insurance application, insurance databases, and the like sources. The insurance sources can be available through social networks, ad hoc and marketing networks, and other external sources. For example, data can be obtained from insurance sites, insurance providers, driver insurance history, and search engines. All this enables recommendation engines to take a more holistic view of the driver. The recommendation engine can recommend different insurance products that save money for the driver, or alternatively can even recommend different insurance companies to save money. Using greater amounts of data lets the engines find connections that might otherwise go unnoticed, which yields better suggestions. This also sometimes requires recommendation systems to use complex big-data analysis techniques. Online public profiles and preference listings on social networking sites such as Facebook add useful data.

Most recommendation engines use complex algorithms to analyze driver behavior and suggest recommended activities that employ personalized collaborative filtering, which use multiple agents or data sources to identify behavior patterns and draw conclusions. This approach helps determine that numerous drivers who have same or similar type of behavior in the past may have to perform one or more similar activities in the future. Many systems use expert adaptive approaches. These techniques create new sets of suggestions, analyze their performance, and adjust the recommendation pattern for similar behavior of drivers. This lets systems adapt quickly to new trends and behaviors. Rules-based systems enable businesses to establish rules that optimize recommendation performance.

FIG. 14 is a diagram 5600 illustrates generally, a first vehicle program communicating with a second vehicle program through an Inter-Vehicle networking, according to embodiments as disclosed herein. In an embodiment, the system develops inter-vehicular networking, computing, transceivers, and sensing technologies in the vehicles. Such vehicles have embedded computers, GPS receivers, short-range wireless network interfaces, and potentially access to in-car sensors and the Internet. Furthermore, they can interact with road-side wireless sensor networks and sensors embedded in other vehicles. These capabilities can be leveraged into distributed computing and sensing applications over vehicular networks for safer driving, dynamic route planning, mobile sensing, or in-vehicle entertainment. The system can include vehicular-specific network protocols, middleware platforms, and security mechanisms to process the data. As shown in FIG. 14, a first driver operating a vehicle observes a second driver operating a vehicle within his visual range and wants to send a message to the second driver. The vehicle can include identifying information that is visually ascertainable such as the model, vehicle color, number of doors, license plate number and state. The vehicle may include additional information that is only ascertainable from up close or at certain angles, or via certain technologies, such as a roof top identification number, vehicle identification number, taxi badge number, Bluetooth, or RFID code, and the like. In an embodiment, a sender having access to the vehicle monitoring device and viewing a second vehicle desires to contact the driver of the second vehicle. In one embodiment, in case of an accident as detected by an accelerometer or airbag deployment, both vehicles automatically exchange insurance information and the drivers simply confirm and signs to accept. In another embodiment, in case of a hit-and-run, the vehicle computer would automatically capture insurance information from the other vehicle and store all parameters arising from the accident for accident investigator's review. In another embodiment, if one vehicle detects that the other vehicle has a low insurance rating, the vehicle automatically enters a defensive driving mode around that vehicle. As best shown in FIG. 16, the sender initiates communication via a telephone or handheld computer or vehicle monitoring device and accesses the interface to the inter-vehicle networking service and database. The sender can select "send message" from the graphical or audio menu to send message or directly communicate with the driver of the second vehicle.

For example, the sender can directly communicate with the driver using the inter-vehicle networking or the sender can choose from a table of messages that can be sent to the driver using the inter-vehicle networking. For example, the message can take the form of voice, audio, video, or other data which can be converted to a digital signal and sent to any communications terminal. The inter-vehicle networking database receives the message or encrypted message and reconstructs the message, including the address information. The inter-vehicle networking then separates out the address information including such as for example, but not limited to, license plate number, vehicle identification number, and the like.

In an embodiment, the message may include a return address for the sender, so that a reply can be returned merely by hitting the "reply to" or "call back" button on the message. One skilled in the art would also recognize that the message could be sent anonymously or by a non-returnable address. Alternatively, the message could be a general broadcast sent by a police officer or other official sending a warning message to speeders or an informational message such as "road closed ahead" or other message.

Because these cars are networked—the car in front of one vehicle is connected to the car in front it and so forth—in a distributed mesh, an intelligent vehicle can know if cars miles down the road are slamming on their brakes, alerting the driver to potential traffic jams. Given enough vehicles with the technology, individual cars become nodes in a constantly changing, self-aware network that can not only monitor what's going on in the immediate vicinity, but across a citywide traffic grid.

In one embodiment, the processor receives travel routes and sensor data from adjacent vehicles, such information is then used for preparing vehicular brakes for a detected turn or an anticipated turn from adjacent vehicles. The travel routes can be transmitted over a vehicular Wi-Fi system that sends protected information to nearby vehicles equipped with Wi-Fi or Bluetooth or ZigBee nodes. In one embodiment, a mesh-network is formed with Wi-Fi transceivers, wherein each vehicle is given a temporary ID in each vehicular block, similar to a cellular block where vehicles can join or leave the vehicular block. Once the vehicle joins a group, travel routes and sensor data is transferred among vehicles in a group. Once travel routes are shared, the processor can determine potential or desired actions from the adjacent vehicles and adjust appropriately. For example, if the car in front of the vehicle is about to make a turn, the system prepares the brakes and gently tugs the driver's seat belt to give the drive notice that the car in front is about to slow down. In another example, if the processor detects that the driver is about to make a lane change to the left based on sensor data and acceleration pedal actuation, but if the processor detects that the vehicle behind in the desired lane is also speeding up, the system can warn the driver and disengage the lane change to avoid the accident. Thus, the processor receives travel routes and sensor data from adjacent vehicles and notifying the driver of a detected turn or an anticipated turn from adjacent vehicles. The processor receives travel routes and sensor data from adjacent vehicles and optimizes group vehicular speed to improve fuel efficiency. The processor receives travel routes and sensor data from adjacent vehicles and sequences red light(s) to optimize fuel efficiency. The processor notifies the driver of driving behaviors from other drivers at a predetermined location. The processor switches turn signals and brakes using a predetermined protocol to reduce insurance premium for the driver. The processor warns the driver to avoid driving in a predetermined pattern, driving during a predetermined time, driving in a predetermined area, or parking in a predetermined area to reduce insurance premium for the driver. The processor sends driver behavior data to an insurer, including at least one of: vehicle speed, vehicle accelerations, vehicle location, seatbelt use, wireless device use, turn signal use, detection of ethanol vapor, driver seating position, and time.

The various systems described above may be used by the computer to operate the vehicle and maneuver from one location to another. For example, a user may enter destination information into the navigation system, either manually or audibly. The vehicle may determine its location to a few inches based on a combination of the GPS receiver data, the sensor data, as well as the detailed map information. In response, the navigation system may generate a route between the present location of the vehicle and the destination.

When the driver is ready to relinquish some level of control to the autonomous driving computer, the user may activate the computer. The computer may be activated, for example, by pressing a button or by manipulating a lever such as gear shifter. Rather than taking control immediately, the computer may scan the surroundings and determine whether there are any obstacles or objects in the immediate vicinity which may prohibit or reduce the ability of the vehicle to avoid a collision. In this regard, the computer may require that the driver continue controlling the vehicle manually or with some level of control (such as the steering or acceleration) before entering into a fully autonomous mode.

Once the vehicle is able to maneuver safely without the assistance of the driver, the vehicle may become fully autonomous and continue to the destination. The driver may continue to assist the vehicle by controlling, for example, steering or whether the vehicle changes lanes, or the driver may take control of the vehicle immediately in the event of an emergency.

The vehicle may continuously use the sensor data to identify objects, such as traffic signals, people, other vehicles, and other objects, in order to maneuver the vehicle to the destination and reduce the likelihood of a collision. The vehicle may use the map data to determine where traffic signals or other objects should appear and take actions, for example, by signaling turns or changing lanes. Once the vehicle has arrived at the destination, the vehicle may provide audible or visual cues to the driver. For example, by displaying "You have arrived" on one or more of the electronic displays.

The vehicle may be only partially autonomous. For example, the driver may select to control one or more of the following: steering, acceleration, braking, and emergency braking.

The vehicle may also have one or more user interfaces that allow the driver to reflect the driver's driving a style. For example, the vehicle may include a dial which controls the level of risk or aggressiveness with which a driver would like the computer to use when controlling the vehicle. For example, a more aggressive driver may want to change lanes more often to pass cars, drive in the left lane on a highway, maneuver the vehicle closer to the surrounding vehicles, and drive faster than less aggressive drivers. A less aggressive driver may prefer for the vehicle to take more conservative actions, such as somewhat at or below the speed limit, avoiding congested highways, or avoiding populated areas in order to increase the level of safety. By manipulating the dial, the thresholds used by the computer to calculate whether to pass another car, drive closer to other vehicles, increase speed and the like may change. In other words, changing the dial may affect a number of different settings used by the computer during its decision making processes. A driver may also be permitted, via the user interface, to change individual settings that relate to the driver's preferences. In one embodiment, insurance rates for the driver or vehicle may be based on the style of the driving selected by the driver.

Aggressiveness settings may also be modified to reflect the type of vehicle and its passengers and cargo. For example, if an autonomous truck is transporting dangerous cargo (e.g., chemicals or flammable liquids), its aggressiveness settings may be less aggressive than a car carrying a single driver—even if the aggressive dials of both such a truck and car are set to "high." Moreover, trucks traveling across long distances over narrow, unpaved, rugged or icy terrain or vehicles may be placed in a more conservative mode in order reduce the likelihood of a collision or other incident.

In another example, the vehicle may include sport and non-sport modes which the user may select or deselect in order to change the aggressiveness of the ride. By way of example, while in "sport mode", the vehicle may navigate through turns at the maximum speed that is safe, whereas in "non-sport mode", the vehicle may navigate through turns at the maximum speed which results in g-forces that are relatively imperceptible by the passengers in the car.

The vehicle's characteristics may also be adjusted based on whether the driver or the computer is in control of the vehicle. For example, when a person is driving manually the suspension may be made fairly stiff so that the person may "feel" the road and thus drive more responsively or comfortably, while, when the computer is driving, the suspension may be made such softer so as to save energy and make for a more comfortable ride for passengers. The adjustment can be done by hand as in the following:

1. A method to control the car using eye.
2. The method of claim 1, further comprising detecting an eye gaze and eye blink and thoughts captured through EMG signal in a predetermined sequence to control the vehicle.
3. The method of claim 1, further comprising controlling a car window position using an arm gesture and finger gesture and exiting by forming a fist.
4. The method of claim 1, further comprising controlling a seat position using an arm gesture and a figure gesture, comprising moving the seat as specified by an arm angular movement.
5. The method of claim 1, further comprising unlocking a hood or a trunk using an arm gesture and a figure gesture, wherein to open the trunk a driver makes a right angular movement and an opposite movement for unlocking the hood.
6. The method of claim 1, further comprising controlling temperature of a driver and front passenger seats using an arm gesture and a finger gesture, wherein the number of fingers affect a seat temperature.
7. The method of claim 1, further comprising performing a left arm gesture, voice and eye based navigation control for a car.
8. The method of claim 1, further comprising activating a positioning system and selecting start and destination using gestures.
9. The method of claim 1, further comprising controlling a mirror position with gesture, voice and eye based control.
10. The method of claim 1, further comprising controlling music using hand gesture.
11. The method of claim 1, further comprising controlling vehicle temperature with a hand gesture.
12. The method of claim 1, further comprising controlling sound volume using a gesture.
13. The method of claim 1, further comprising controlling sun roof opening and closure using a gesture.
14. The method of claim 1, further comprising controlling wind shield wipers with a gesture.
15. The method of claim 1, further comprising controlling operation of a rear view mirror.
16. The method of claim 1, further comprising gesturing on a steering wheel to make calls, receive and respond to texts, launch apps, get turn-by-turn directions, find the nearest other local businesses, play music, or search the Internet while driving.
17. The method of claim 1, further comprising controlling an air conditioning system.
18. The method of claim 1, further comprising recognizing a combination of gestures to create a custom gesture control.
19. The method of claim 1, further comprising ultrasonic sensors to detect gestures.
20. The method of claim 1, further comprising rendering a display or sound or tactile feedback for a detected gesture.

Augmented Reality/Virtual Reality Sports Gaming

Figure 15:
FIG. 15 shows an exemplary virtual reality camera mounted on a gear.

FIG. 15 shows an exemplary 360 degree camera on a helmet, for example, for augmenting reality of games. Using augmented reality, various ways may exist for a user to "participate" in a live event. Generally, augmented reality refers to a presentation of a real world environment augmented with computer-generated data (such as sound, video, graphics or other data). In some embodiments, augmented reality, implemented in conjunction with a live event, may allow a user to control a virtual object that appears to compete or otherwise interact with the participants of the live event. For example, an end user device, such as a mobile phone, tablet computer, laptop computer, or gaming console may be used to present a live video feed of an event to a user. This live video feed may be video of an event that is occurring in real-time, meaning the live event is substantially concurrently with the presentation to the user (for example, buffering, processing, and transmission of the video feed may result in a delay anywhere from less than a second to several minutes). The presentation of the live event may be augmented to contain one or more virtual objects that can be at least partially controlled by the user. For instance, if the live event is a stock car race, the user may be able to drive a virtual car displayed on the end user device to simulate driving in the live event among the actual racers. As such, the user may be able to virtually "compete" against the other drivers in the race. The virtual object, in this example a car, may be of a similar size and shape to the real cars of the video feed. The user may be able to control the virtual car to race against the real cars present in the video feed. The real cars appearing in the video feed may affect the virtual object. For example, the virtual object may not be allowed to virtually move through a real car on the augmented display, rather the user may need to drive the virtual object around the real cars. Besides racing, similar principles may be applied to other forms of live events; for example, track and field events (e.g., discus, running events, the hammer toss, pole vaulting), triathlons, motorbike events, monster truck racing, or any other form of event that a user could virtually participate in against the actual participants in the live event. In some embodiments, a user may be able to virtually replay and participate in past portions of a live event. A user that is observing a live event may desire to attempt to retry an occurrence that happened during the live event. While viewing the live event, the user may be presented with or permitted to select an occurrence that happened in the course of the live event and replay it such that the user's input affects the outcome of at least that portion of the virtualized live event. Using a baseball game as an example, with runners on first and third, two outs, and the count being two balls and two strikes, the pitcher may throw a splitter, successfully striking out the batter with a pitch in the dirt. The inning may end and the game may continue. The user may desire to replay this unsuccessful at-bat with himself controlling the batter during the commercial break. As such, via an end user device, the user may be able to indicate the portion of the game he wishes to replay (e.g., the last at-bat). Game facts from the live event may be used to virtually recreate this at-bat for the user. For instance, the virtual game loaded by the user may use game facts leading up to the at-bat the user has selected. For instance, the opposing team, the stadium, the score, the time of day, the batter, the pitcher, and the sequence of pitches thrown by the pitcher may be used to provide the user with a virtual replay of at least that portion of the baseball game that the user can affect via input (e.g., swinging and aiming the virtual bat). In replaying the selected portion of the live event, the entire event may be virtualized. As such, referring to the baseball example, the pitcher, stadium, field, fielders, batter, and ball may all be replaced by virtual objects, with one (or more) of the virtual objects, such as the batter, being controlled by the user. As such, this may resemble a video game instantiated with data from the live event. In some embodiments, a portion of the live event may involve a playback of a video feed of the live event with a virtual object that is controlled by the user being augmented. Referring again to the example of the baseball game, the pitcher, stadium, fielders, and field may be replayed from the video feed; the batter and/or ball may be virtualized. As such, the user may control the batter and swing at a virtual ball that has taken the place of the real ball present in the video feed. Besides baseball, such reenactment of a portion of a live event may be applied to various forms of sporting events, such as football, soccer, tennis, golf, hockey, basketball, cricket, racing, skiing, gymnastics, and track and field events. Other forms of live events, besides sports, may also be reenacted using such techniques.

A multi-headed camera array may be at least part of a modular camera system, with each camera forming a module of the modular camera system. The camera array has a flexible structure so that it is easy to remove a particular camera module from the camera array and to add new camera modules to the camera array. The camera modules in the camera array may be configured in different geometries. For example, the camera array includes multiple camera modules arranged in a line, a cylinder, a sphere, or another geometry. Each camera module may be configured to point to a different direction so that the camera array may capture an object or a scene from multiple directions at the same time.

The camera system described herein may additionally include a set of algorithms for processing the video data captured by the camera array. The set of algorithms are stored on a non-transitory memory for converting the input across multiple camera modules into a single stream of 3D video (e.g., a single compressed stream of 3D video data). The set of algorithms may be implemented in one or more "modules". For example, the set of algorithms includes color correction algorithms for smoothing and correcting colors in the video data. In another example, the set of algorithms may be implemented in software that stitches the video data from multiple cameras into two large-format, panoramic video streams for left and right eye viewing, and encodes and compresses the video using a standard MPEG format or other suitable encoding/compression format.

One embodiment allows combined augmented reality and virtual reality on the display. The method may include selectively allowing a transmission of light from a local environment of the user based on a visualization mode of the display object. The visualization mode may be one of an augmented reality mode, a virtual reality mode, and a combination of augmented and virtual reality modes.

In another embodiment, sensors may be placed to track eye movement as well as hand gestures and verbal commands. The method may further comprise capturing a field-of-view image of each of the user's eyes. The captured field of view image may be used to estimate a head pose of the user. The captured field-of-view image may be used to convert at least one physical object to a physically rendered virtual object, and to display the physically rendered virtual object to the user. In another embodiment, sensors may be placed to track eye movement as well as hand gestures and verbal commands. Then, a method comprises tracking a movement of a user's eyes, estimating a depth of focus of the user's eyes based on the tracked eye movement, modifying a light beam associated with a display object based on the estimated depth of focus such that the display object appears in focus, and projecting the modified light beam into the user's eyes. The diameter of the projected light beam projected to the user's eyes may be less than 0.7 mm.

For the athlete/participant who wish to enhance their gaming via augmented or virtual reality, features may include the following:

1. A method for using augmented reality, the method comprising: receiving, by a computerized device, a data stream with a 360 degree view of a live event on each participant, wherein the data stream comprises live video augmented with positions of team mates and opposing players and recommends a play routine based on live field condition and positions of other players, wherein the user can select a point of view from a selected participant.

2. The method for using augmented reality of claim 1, wherein the user plays in a virtual reality version of the live event.

3. The method for using augmented reality of claim 1, wherein the live event is a sporting event.

4. The method of claim 7, wherein the live event comprises: soccer, football, basketball, tennis, boxing, car racing, golf, ice hockey, badminton, volleyball, cycling, swimming, snooker, martial arts, rugby, motorbike, hockey, table tennis, horse racing, gymnastics, handball, figure skating, wrestling, skiing, diving, skating, archery, sailing, wrestling, fencing, equestrian, rowing, surfing, Beach Volleyball, Pool/

Billiards, Lacrosse, Windsurfing, Polo, Tenpin Bowling, Racquetball, Competitive Climbing, Mountain Biking.

For viewers who wish to participate via augmented or virtual reality, features may include the following:

1. A method for using augmented reality, the method comprising: receiving, by a computerized device, a data stream with a 360 degree view of a live event on each participant, wherein the data stream comprises live video, wherein: the live video comprises a live object; receiving, by the computerized device, input from a user, wherein the input from the user affects behavior of a virtual object; and presenting, by the computerized device, the live event augmented by the virtual object, wherein a behavior of the live object of the live event affects the behavior of the virtual object and each participant, wherein the user can select a point of view from a selected participant.

2. The method for using augmented reality of claim 1, wherein: the virtual object is presented such that the virtual object appears to compete with the live object.

3. The method for using augmented reality of claim 1, wherein the live event is a sporting event.

4. The method for using augmented reality of claim 1, further comprising: receiving, by the computerized device, data corresponding to a second virtual object from a remote computerized device; and displaying, by the computerized device, the live event augmented by the virtual object further augmented with the second virtual object.

5. The method for using augmented reality of claim 4, wherein the behavior of the second virtual object is affected by a second user.

6. The method for using augmented reality of claim 4, further comprising: modifying, by the computerized device, behavior of the virtual object in response to the second virtual object.

7. A method for using augmented reality, the method comprising: receiving, by a computerized device, data corresponding to a live event; presenting, by the computerized device, the live event up to a point in time; presenting, by the computerized device, a virtual event at least partially based on an event that occurred during the live event earlier than the point in time; receiving, by the computerized device, input linked with the virtual event, wherein the input is received from a user; and presenting, by the computerized device, an outcome of the virtual event, wherein the outcome is at least partially based on the input received from the user.

8. The method for using augmented reality of claim 7, wherein: the virtual event is presented at least starting when the live event is stopped.

9. The method of claim 7, wherein the live event is a sporting event.

10. The method of claim 7, wherein the live event comprises: soccer, football, basketball, tennis, boxing, car racing, golf, ice hockey, badminton, volleyball, cycling, swimming, snooker, martial arts, rugby, motorbike, hockey, table tennis, horse racing, gymnastics, handball, figure skating, wrestling, skiing, diving, skating, archery, sailing, wrestling, fencing, equestrian, rowing, surfing, Beach Volleyball, Pool/Billiards, Lacrosse, Windsurfing, Polo, Tenpin Bowling, Racquetball, Competitive Climbing, Mountain Biking.

11. A method for using virtual reality, the method comprising: receiving, by a computerized device, a data stream with a 360 degree view of a computer generated event on each participant, wherein the data stream comprises live video, wherein: the live video comprises a live object; receiving, by the computerized device, input from a user, wherein the input from the user affects behavior of a virtual object; and presenting, by the computerized device, the live event augmented by the virtual object, wherein a behavior of the live object of the live event affects the behavior of the virtual object and each participant.

12. A method for using augmented reality and virtual reality, the method comprising:

receiving, by a computerized device, a data stream with a 360 degree view of a live event on each participant, wherein the data stream comprises live video, wherein: the live video comprises a live object; receiving, by the computerized device, input from a user, wherein the input from the user affects behavior of a virtual object; and presenting, by the computerized device, the live event augmented by the virtual object, wherein a behavior of the live object of the live event affects the behavior of the virtual object and each participant, and wherein the virtual reality is rendered by switching the display from an augmented view to a virtual reality view by fading out the augmented view on the display to show only the virtual reality view and switching back when augmented reality view is desired.

Moreover, the viewers can collaboratively read the situation and recommend a strategy in real-time to improve viewer participation. In this manner, 1. A method for participating in a game, the method comprising: collecting from viewers of a game one or more state change events during a game; determining whether a series of the collected state change events are a known pattern; requesting, when the series of the collected state change events is an unknown pattern, viewers of the game to identify what caused the collected state change events; and judging, by the viewers, a best reason among the identified causes of the collected state change events.

2. The method of claim 1, comprising running a lottery to decide which recommendation is used for the next play in the game.

3. The method of claim 1, further comprising: compensating at least one viewer who is judged to have the best reason among the identified causes of the collected state change events.

4. The method of claim 1, further comprising: storing as the known pattern, the best reason among the identified causes of the collected state change events when one of the pattern is repeated greater than a threshold number of repeats, and the number of the viewers who agree with the corresponding best reason is greater than a threshold number of users.

5. The method of claim 4, further comprising: associating with the stored best reason a corrective action to be taken in response to a future corresponding the collected state change events.

6. The method of claim 4, further comprising: displaying to the other viewers and players, when the stored best reason is known, the occurrence of the stored best reason.

7. The method of claim 5, further comprising: transmitting the stored best reason to other viewers.

8. The method of claim 1, wherein the series of the collected state change events are at least two state change events that occur within a threshold period of time from each other.

Recognition of Exercise Pattern and Tracking of Calorie Consumption

FIG. 16A illustrates the positions of a ski 126' and skier 128' during a lofting maneuver on the slope 132'. The ski 126' and skier 128' speed down the slope 132' and launch into the air 136 at position "a," and later land at position "b" in accord with the well-known Newtonian laws of physics.

With an airtime sensor, described above, the unit 10 calculates and stores the total airtime that the ski 126' (and hence the skier 128') experiences between the positions "a" and "b" so that the skier 128' can access and assess the "air" time information. Airtime sensors such as the sensor 14 may be constructed with known components. Preferably, the sensor 14 incorporates either an accelerometer or a microphone. Alternatively, the sensor 14 may be constructed as a mechanical switch that detects the presence and absence of weight onto the switch. Other airtime sensors 14 will become apparent in the description which follows. The accelerometer senses vibration—particularly the vibration of a vehicle such as a ski or mountain bike—moving along a surface, e.g., a ski slope or mountain bike trail. This voltage output provides an acceleration spectrum over time; and information about airtime can be ascertained by performing calculations on that spectrum. Based on the information, the system can reconstruct the movement path, the height, the speed, among others and such movement data is used to identify the exercise pattern. For example, the skier may be interested in practicing mogul runs, and the system can identify foot movement and speed and height information and present the information post exercises as feedback. Alternatively, the system can make live recommendations to improve performance to the athlete.

FIG. 16B illustrates a sensing unit 10" mounted onto a mountain bike 138. FIG. 16B also shows the mountain bike 138 in various positions during movement along a mountain bike race course 140 (for illustrative purposes, the bike 138 is shown without a rider). At one location "c" on the race course 140, the bike 138 hits a dirt mound 142 and catapults into the air 144. The bike 138 thereafter lands at location "d". As above, with speed and airtime sensors, the unit 10 provides information to a rider of the bike 138 about the speed attained during the ride around the race course 140; as well as information about the airtime between location "c" and "d". In this case, the system can recommend a cadence to be reached by the rider, strengthen of abdominals, back and arms, for example.

For golf exercise, It is beneficial to require the golfer to swing the golf club a plurality of times at each swing position to account for variations in each swing. The swing position at which the golf club is swung can be determined by analysis of the measured acceleration provided by the accelerometer, e.g., the time at which the acceleration changes. Data obtained during the training stage may be entered into a virtual table of swing positions and estimated carrying distances for a plurality of different swing positions and a plurality of different swings. A sample format for such a table is as follows, and includes the averaged carrying distance for each of four different swing positions. The swing analyzer provides a golfer with an excellent estimation of the carrying distance of a golf ball for a golf club swing at a specific swing position because it has been trained on actual swings by the golfer of the same club and conversion of information about these swings into estimated carrying distances. The golfer can improve their golf game since they can better select a club to use to hit a golf club for different situations during a round of golf. Also, the swing pattern is used to identify each club path responsible for the curve of any shot and this information is used to improve the golfer. The direction of the club path relative to the target, out-to-in (fade pattern) or in-to-out (draw pattern), is what I refer to as a players swing pattern. Players that swing from in-to-out will tend to hit draws and players that swing from out-to-in will tend to hit fades. Where the ball is struck on the face of the driver (strike point) can drastically alter the effect of a players swing pattern on ball flight. Thus, the camera detects where the ball is struck, and a computer physics model of ball behavior is presented to the golfer to improve the score. Shots struck off the heel will tend to fade more or draw less and shots struck off the toe will tend to draw more or fade less. Thus, camera images of the shots struck of heel or toe can also be used to provide pattern recognition/prediction and for training purposes.

For tennis, examples of motions determined for improvement are detailed next. The system can detect if the continental grip is achieved. Throwing Action pattern is also detected, as the tennis serve is an upwards throwing action that would deliver the ball into the air if it were a baseball pitch. Ball Toss improvements can be determined when the player lines the straight arm up with the net post and release the ball when your hand reaches eye level. The system checks the forward direction so the player can drive weight (and built up momentum) forward into the ball and into the direction of the serve.

The sensors can work with a soccer training module with kinematics of ball control, dribbling, passing, crossing, shooting, heading, volleying, taking throw-ins, penalties, corner kicks and free kicks, tackling, marking, juggling, receiving, shielding, clearing, and goalkeeping. The sensors can work with a basketball training module with kinematics of crossover dribble, behind back, pull back dribble, low dribble, basic dribble, between legs dribble, Overhead Pass, Chest Pass, Push Pass, Baseball Pass, Off-the-Dribble Pass, Bounce Pass, Jump Shot, Dunk, Free throw, Layup, Three-Point Shot, Hook Shot.

The sensors can work with a baseball training module with kinematics of Hitting, Bunting, Base Running and Stealing, Sliding, Throwing, Fielding Ground Balls, Fielding Fly Balls, Double Plays and Relays, Pitching and Catching, Changing Speeds, Holding Runners, Pitching and Pitcher Fielding Plays, Catching and Catcher Fielding Plays.

Figure 16D:
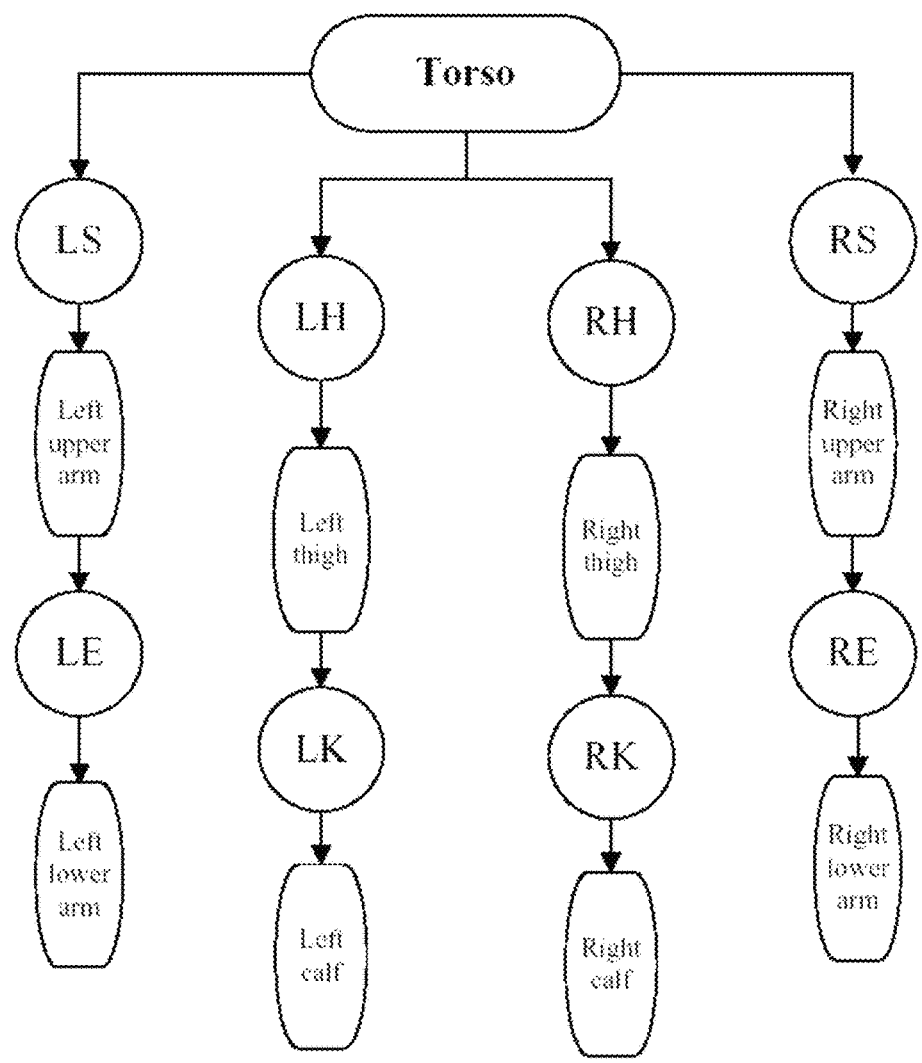
FIG. 16D shows a kinematic modeling for detecting exercise motion which in turn allows precision coaching suggestions.

For weight training, the sensor can be in gloves as detailed above, or can be embedded inside the weight itself, or can be in a smart watch, for example. The user would enter an app indicating that the user is doing weight exercises and the weight is identified as a dumbbell, a curl bar, and a bar bell. Based on the arm or leg motion, the system automatically detects the type of weight exercise being done. In one embodiment shown in FIG. 15C, with motion patterns captured by glove and sock sensors, the system can automatically detect the following exemplary exercise:

Upper Body:
  Chest: Barbell Bench Presses, Barbell Incline Presses, Dumbbell Bench Presses, Dumbbell Incline Presses, Dumbbell Flyes, Cable Crossovers
  Back: Pull-Ups, Wide-Grip Lat Pulldowns, One-Arm Dumbbell Rows, Seated Cable Rows, Back Extensions, Straight Arm Pulldowns
  Shoulders: Seated Dumbbell Presses, Front Raises, Lateral Raises, Reverse Flyes, Upright Cable Rows, Upright Barbell Rows
  Biceps: Alternate Dumbbell Curls, Barbell Curls, Preacher Curls, Concentration Curls, Cable Curls, Hammer Curls
  Triceps: Seated Triceps Presses, Lying Triceps Presses, Triceps Kickbacks, Triceps Pushdowns, Cable Extensions, Bench Dips
Lower Body
  Quadriceps: Barbell Squats, Leg Presses, Leg Extensions
  Hamstrings: Dumbbell Lunges, Straight-Leg Deadlifts, Lying Leg Curls
  Calves: Seated Calf Raises, Standing Heel Raises Abs: Floor Crunches, Oblique Floor Crunches, Decline Crunches, Decline Oblique, Hanging Knee Raises, Reverse Crunches, Cable Crunches, Cable Oblique Crunches In one implementation in FIG. 16D, an HMM is used to track weightlifting motor skills or enthusiast movement patterns. Human movement involves a periodic motion of the legs. Regular walking involves the coordination of motion at the hip, knee and ankle, which consist of complex joints. The muscular groups attached at various locations along the skeletal structure often have multiple functions. The majority of energy expended during walking is for vertical motion of the body. When a body is in contact with the ground, the downward force due to gravity is reflected back to the body as a reaction to the force. When a person stands still, this ground reaction force is equal to the person's weight multiplied by gravitational acceleration. Forces can act in other directions. For example, when we walk, we also produce friction forces on the ground. When the foot hits the ground at a heel strike, the friction between the heel and the ground causes a friction force in the horizontal plane to act backwards against the foot. This force therefore causes a breaking action on the body and slows it down. Not only do people accelerate and brake while walking, they also climb and dive. Since reaction force is mass times acceleration, any such acceleration of the body will be reflected in a reaction when at least one foot is on the ground. An upwards acceleration will be reflected in an increase in the vertical load recorded, while a downwards acceleration will be reduce the effective body weight. Zigbee wireless sensors with tri-axial accelerometers are mounted to the enthusiast on different body locations for recording, for example the tree structure as shown in FIG. 16D. As shown therein, sensors can be placed on the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others.

The sequence of human motions can be classified into several groups of similar postures and represented by mathematical models called model-states. A model-state contains the extracted features of body signatures and other associated characteristics of body signatures. Moreover, a posture graph is used to depict the inter-relationships among all the model-states, defined as PG(ND,LK), where ND is a finite set of nodes and LK is a set of directional connections between every two nodes. The directional connection links are called posture links. Each node represents one model-state, and each link indicates a transition between two model-states. In the posture graph, each node may have posture links pointing to itself or the other nodes.

In the pre-processing phase, the system obtains the human body profile and the body signatures to produce feature vectors. In the model construction phase, the system generate a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and if differences for the motion parameters and curves over time is detected, the system then runs the enthusiast through additional tests to confirm the detected motion.

In one exemplary process for determining exercise in the left or right half of the body, the process compares historical left shoulder (LS) strength against current LS strength (3200). The process also compares historical right shoulder (RS) strength against current RS strength (3202). The process can compare historical left hip (LH) strength against current LH strength (3204). The process can also compare historical right hip (RH) strength against current RH strength (3206). If the variance between historical and current strength exceeds threshold, the process generates warnings (3208). Furthermore, similar comparisons can be made for sensors attached to the left elbow (LE), right elbow (RE), left knee (LK), and right knee (RK) connect the upper and the lower extremities, among others.

The system can ask the enthusiast to squeeze a strength gauge, piezoelectric sensor, or force sensor to determine force applied during squeeze. The user holds the sensor or otherwise engages the sensor. The user then applies and holds a force (e.g., compression, torque, etc.) to the sensor, which starts a timer clock and triggers a sampling start indicator to notify the user to continue to apply (maximum) force to the sensor. Strength measurements are then sampled periodically during the sampling period until the expiration of time. From the sampled strength data, certain strength measurement values are selected, such as the maximum value, average value(s), or values obtained during the sampling period. The user can test both hands at the same time, or alternatively he may test one hand at a time. A similar approach is used to sense leg strength, except that the user is asked to pushed down on a scale to determine the foot force generated by the user.

In one embodiment, exercise motion data acquired by the accelerometer or multi-axis force sensor is analyzed, as will be discussed below, in order to determine the motion of each exercise stroke during the exercise session (i.e., horizontal vertical or circular). In another embodiment for detecting exercise motion using accelerometer, the first minimum discovered during the scanning is noted as the first xmin and considered to be the start of the first brushstroke. The first maximum x value following the first minimum x value is located and construed to be the middle of the first exercise stroke (where exercise motion changes from one direction to the other). The next xmin value indicates the end of the first brushstroke and the beginning of the next brushstroke. The computer records the data for each brushstroke and continues on through the data to find the next brushstroke, recording each successive motion in memory. For the first brushstroke, the maximum and minimum values of the x coordinate (xmax and xmin) are determined. The Y-direction lengths, Ly1 and Ly2, between the data points just before and just after each of xmax and xmin (xmax+1, xmax−1, and Xmin+1, xmin−1) are then determined. The length Lx along the x axis, between xmax and xmin, is also determined. Next, if Lx is less than 2 and either Ly1 or Ly2 is greater than one, then the motion is construed to be vertical. If Ly1 and Ly2 are both less than one, then the motion is construed to be horizontal. Otherwise, the motion is construed to be circular.

Data obtained from the gyroscope, if one is used, typically does not require a complex analysis. To determine which side of the mouth is being brushed at a particular time, the gyroscope data is scanned to determine when the rotational orientation is greater than 180 degrees, indicating the left side, and when it is less than 180 degrees, indicating the right side. As explained above, top and bottom and gum brushing information can also be obtained, without any calculations, simply by examining the data. The time sequence of data that is acquired during exercise and analyzed as discussed above can be used in a wide variety of ways.

In one embodiment, the accelerometers distinguish between lying down and each upright position of sitting and standing based on the continuous output of the 3D accelerometer. The system can detect (a) extended time in a single position; (b) extended time sitting in a slouching posture (kyphosis) as opposed to sitting in an erect posture (lordosis); and (c) repetitive stressful movements, such as may be found on some manufacturing lines, while typing for an extended period of time without proper wrist support, or while working all day at a weight lifting exercise, among others. In one alternative embodiment, angular position sensors, one on each side of the hip joint, can be used to distinguish lying down, sitting, and standing positions. In another embodiment, the system repeatedly records position and/or posture data over time. In one embodiment, magnetometers can be attached to a thigh and the torso to provide absolute rotational position about an axis coincident with Earth's gravity vector (compass heading, or yaw). In another embodiment, the rotational position can be determined through the in-door positioning system as discussed above.

To improve a golf swing, the complex motion of the body first starts with the stance. The system checks that the golfer has a low center of gravity to remain balanced throughout the swing path. The swing starts with the arms moving back in a straight line. When the club head reaches the level of the hip, two things happen: there is a stern wrist cock that acts as a hinge along with the left knee (for a right handed swing), building up its torque by moving into the same line as the belly button before the start of the upswing. As the swing continues to the top of the backswing (again for right handed golf swing), the golfer's left arm should be perfectly straight and his right arm should be hinged at the elbow. The downswing begins with the hips and the lower body rather than the arms and upper body, with emphasis on the wrist cock. As the golfer's hips turn into the shot, the right elbow will drop straight down, hugging the right side of the golfer's torso. As the right elbow drops, the wrists begin to snap through from the wrist cock in the backswing. A solid extension of the arms and good transfer of body should put the golfer leaning up on his right toe, balanced, with the golf club resting on the back of the golfers neck. Importantly, all of the movements occur with precise timing, while the head remains completely still with eyes focused on the ball throughout the entire swing.

The system can identify illnesses and prevent overexertion leading to illnesses such as a stroke. Depending on the severity of the stroke, enthusiasts can experience a loss of consciousness, cognitive deficits, speech dysfunction, limb weakness, hemiplegia, vertigo, diplopia, lower cranial nerve dysfunction, gaze deviation, ataxia, hemianopia, and aphasia, among others. Four classic syndromes that are characteristically caused by lacunar-type stroke are: pure motor hemiparesis, pure sensory syndrome, ataxic hemiparesis syndrome, and clumsy-hand dysarthria syndrome. enthusiasts with pure motor hemiparesis present with face, arm, and leg weakness. This condition usually affects the extremities equally, but in some cases it affects one extremity more than the other. The most common stroke location in affected enthusiasts is the posterior limb of the internal capsule, which carries the descending corticospinal and corticobulbar fibers. Other stroke locations include the pons, midbrain, and medulla. Pure sensory syndrome is characterized by hemibody sensory symptoms that involve the face, arm, leg, and trunk. It is usually the result of an infarct in the thalamus. Ataxic hemiparesis syndrome features a combination of cerebellar and motor symptoms on the same side of the body. The leg is typically more affected than the arm. This syndrome can occur as a result of a stroke in the pons, the internal capsule, or the midbrain, or in the anterior cerebral artery distribution. enthusiasts with clumsy-hand dysarthria syndrome experience unilateral hand weakness and dysarthria. The dysarthria is often severe, whereas the hand involvement is more subtle, and enthusiasts may describe their hand movements as "awkward." This syndrome is usually caused by an infarct in the pons. Different patterns of signs can provide clues as to both the location and the mechanism of a particular stroke. The system can detect symptoms suggestive of a brainstem stroke include vertigo, diplopia, bilateral abnormalities, lower cranial nerve dysfunction, gaze deviation (toward the side of weakness), and ataxia. Indications of higher cortical dysfunction-such as neglect, hemianopsia, aphasia, and gaze preference (opposite the side of weakness)-suggest hemispheric dysfunction with involvement of a superficial territory from an atherothrombotic or embolic occlusion of a mainstem vessel or peripheral branch.

To detect muscle weakness or numbness, in one embodiment, the system applies a pattern recognizer such as a neural network or a Hidden Markov Model (HMM) to analyze accelerometer output. In another embodiment, electromyography (EMG) is used to detect muscle weakness. In another embodiment, EMG and a pattern analyzer is used to detect muscle weakness. In yet another embodiment, a pattern analyzer analyzes both accelerometer and EMG data to determine muscle weakness. In a further embodiment, historical ambulatory information (time and place) is used to further detect changes in muscle strength. In yet other embodiments, accelerometer data is used to confirm that the enthusiast is at rest so that EMG data can be accurately captured or to compensate for motion artifacts in the EMG data in accordance with a linear or non-linear compensation table. In yet another embodiment, the EMG data is used to detect muscle fatigue and to generate a warning to the enthusiast to get to a resting place or a notification to a nurse or caregiver to render timely assistance. The amplitude of the EMG signal is stochastic (random) in nature and can be reasonably represented by a Gaussian distribution function. The amplitude of the signal can range from 0 to 10 mV (peak-to-peak) or 0 to 1.5 mV (rms). The usable energy of the signal is limited to the 0 to 500 Hz frequency range, with the dominant energy being in the 50-150 Hz range. Usable signals are those with energy above the electrical noise level. The dominant concern for the ambient noise arises from the 60 Hz (or 50 Hz) radiation from power sources. The ambient noise signal may have an amplitude that is one to three orders of magnitude greater than the EMG signal. There are two main sources of motion artifact: one from the interface between the detection surface of the electrode and the skin, the other from movement of the cable connecting the electrode to the amplifier. The electrical signals of both noise sources have most of their energy in the frequency range from 0 to 20 Hz and can be reduced.

In one embodiment, the camera captures facial expression and a code such as the Microsoft Emotion API takes a facial expression in an image as an input, and returns the confidence across a set of emotions for each face in the image, as well as bounding box for the face, using the Face API. The emotions detected are anger, contempt, disgust, fear, happiness, neutral, sadness, and surprise. These emotions are understood to be cross-culturally and universally communicated with particular facial expressions. Alternatively, a marker for emotional arousal is galvanic skin response (GSR), also referred to as skin conductance (SC) or electrodermal activity (EDA). EDA modulates the amount of sweat secretion from sweat glands. The amount of sweat glands varies across the human body, being highest in hand and foot regions (200-600 sweat glands per cm2). While sweat secretion plays a major role for thermoregulation and sensory discrimination, changes in skin conductance in hand and foot regions are also triggered quite impressively by emotional stimulation: the higher the arousal, the higher the skin conductance. It is noteworthy to mention that both positive ("happy" or "joyful") and negative ("threatening" or "saddening") stimuli can result in an increase in arousal—and in an increase in skin conductance. Skin conductance is not under conscious control. Instead, it is modulated autonomously by sympathetic activity which drives human behavior, cognitive and emotional states on a subconscious level. Skin conductance therefore offers direct insights into autonomous emotional regulation. It can be used as alternative to self-reflective test procedures, or—even better—as additional source of insight to validate verbal self-reports or interviews of a respondent. Based on the detected emotion, the exercise can be increased, decreased, or stopped altogether.

Data from multiple exercise sessions may be collected and used to compile a history of the user's habits over an extended period of time, enabling the user's trainer to better understand user compliance issues. The trainer can review the data with the user and view the animations of the user's exercise sessions during an office visit, allowing the trainer to better instruct the user in proper brushing technique. The trainer can also review the patient's brushing history over time, to determine whether the patient's exercise technique is improving.

The sensor 14 can be integrated into objects already associated with the sporting activity. In one aspect, the sensing unit is integrated into the ski boot or other boot. In another aspect, the sensing unit is integrated into the binding for a ski boot or snowboarder boot. In still another aspect, the sensing unit is integrated into a ski, snowboard, mountain bike, windsurfer, windsurfer mast, roller blade boot, skate-board, kayak, or other vehicle. Collectively, the objects such as the ski boot and the variety of vehicles are denoted as "implements". Accordingly, when the sensing unit is not "stand alone", the housing which integrates the controller subsystem with one or more sensors and battery can be made from the material of the associated implement, in whole or in part, such that the sensing unit becomes integral with the implement. The universal interface is therefore not desired in this aspect.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The embodiments described herein may include the use of a special purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general purpose or special purpose computer. By way of example, and not limitation, such computer-readable media may include tangible computer-readable storage media including RAM, ROM, EEPROM, CD-ROM or other optical disk storage, magnetic disk storage or other magnetic storage devices, or any other storage medium which may be used to carry or store desired program code in the form of computer-executable instructions or data structures and which may be accessed by a general purpose or special purpose computer. Combinations of the above may also be included within the scope of computer-readable media. Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. As used herein, the term "module" or "component" may refer to software objects or routines that execute on the computing system. The different components, modules, engines, and services described herein may be implemented as objects or processes that execute on the computing system (e.g., as separate threads). While the system and methods described herein may be preferably implemented in software, implementations in hardware or a combination of software and hardware are also possible and contemplated. In this description, a "computing entity" may be any computing system as previously defined herein, or any module or combination of modulates running on a computing system. All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A device, comprising:
    a processor coupled to a wireless transceiver;
    a camera to determine a distance, shape, or dimension of an object proximal to the device;
    an accelerometer to detect acceleration of the device; and
    a module to record the motion of the device, to compare and to render video responsive to a third-party or another device based on camera and accelerometer outputs.

2. The device of claim 1, comprising a pressure sensor, a motion sensor, a finger sensor, a digit motion sensor, an EKG sensor, a bio sensor, a medical sensor, or a temperature sensor.

3. The device of claim 1, comprising a module to follow other third parties or other devices in a flock.

4. The device of claim 1, comprising a road-contacting surface, air-contacting surface or water-contacting surface.

5. The device of claim 1, comprising a gesture identifying component configured to identify hand or finger gesture to the device.

6. The device of claim 1, comprising an optical positioning system or a laser positioning system.

7. The device of claim 1, comprising phone display, an augmented reality display, or a virtual reality display.

8. The device of claim 1, comprising a sensor to detect an imminent impact and activate crash protection for a user.

9. The device of claim 1, comprising a hidden markov model (HMM) or a deep learning machine to detect patterns from the camera and the accelerometer.

10. The device of claim 1, comprising an emotion detector to detect a user condition.

11. A system, comprising:
   an accelerometer disposed in the system for measuring a force on the system;
   a radio frequency transmitter disposed in the system and coupled to the accelerometer for transmitting measurements;
   a camera in the system to determine a distance, shape, or dimension of an object near the system;
   a radio frequency receiver for receiving the measurements; and
   a module to compare a third party or device motion with a user motion and to render video responsive to the motion.

12. The system of claim 11, comprising a pressure sensor, a motion sensor, a finger sensor, a digit motion sensor, an EKG sensor, a bio sensor, a medical sensor, a temperature sensor, a hand gesture sensor.

13. The system of claim 11, comprising a module to follow other third parties or other devices in a flock.

14. The system of claim 11, comprising a positioning system.

15. The system of claim 11, comprising a cloud computer coupled to the receiver to predict the impact and to protect a user for the potential impact.

16. The system of claim 11, comprising a phone display, an augmented reality display, or a virtual reality display controlled by the processor.

17. The system of claim 11, comprising vibrator coupled to the processor.

18. The system of claim 17, comprising a phone display, an augmented reality display, or a virtual reality display to render images to stimulate or excite a user.

19. The system of claim 11, comprising phone display, an augmented reality display, or a virtual reality display to render images to stimulate or excite a user.

20. The system of claim 19, comprising an object, a vibrator or a toy operating in conjunction with the phone display, the augmented reality display, or the virtual reality display to render images to stimulate or excite a user.

* * * * *